US011746162B2

(12) United States Patent
Chen et al.

(10) Patent No.: US 11,746,162 B2
(45) Date of Patent: *Sep. 5, 2023

(54) COMPOSITIONS AND METHODS FOR T-CELL RECEPTOR GENE ASSEMBLY

(71) Applicant: RootPath Genomics, Inc., Watertown, MA (US)

(72) Inventors: Xi Chen, Newton, MA (US); Ely Porter, Medford, MA (US)

(73) Assignee: ROOTPATH GENOMICS, INC., Watertown, MA (US)

(*) Notice: Subject to any disclaimer, the term of this patent is extended or adjusted under 35 U.S.C. 154(b) by 38 days.

This patent is subject to a terminal disclaimer.

(21) Appl. No.: 17/554,013

(22) Filed: Dec. 17, 2021

(65) Prior Publication Data

US 2022/0106377 A1 Apr. 7, 2022

Related U.S. Application Data

(63) Continuation of application No. 17/493,469, filed on Oct. 4, 2021, which is a continuation of application No. PCT/US2020/026558, filed on Apr. 3, 2020.

(60) Provisional application No. 62/972,231, filed on Feb. 10, 2020, provisional application No. 62/898,053, filed on Sep. 10, 2019, provisional application No. 62/838,465, filed on Apr. 25, 2019, provisional application No. 62/829,813, filed on Apr. 5, 2019.

(51) Int. Cl.
*C12Q 1/68* (2018.01)
*C07K 16/44* (2006.01)
*C07K 14/725* (2006.01)

(52) U.S. Cl.
CPC .......... *C07K 16/44* (2013.01); *C07K 14/7051* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,858,358 A | 1/1999 | June et al. |
| 5,883,223 A | 3/1999 | Gray |
| 6,120,766 A | 9/2000 | Hale et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,749,697 B2 | 7/2010 | Oleksiewicz et al. |
| 9,738,699 B2 | 8/2017 | Johnson et al. |
| 9,926,555 B2 | 3/2018 | Johnson et al. |
| 10,221,437 B2 | 3/2019 | Weitz et al. |
| 11,208,457 B2 | 12/2021 | Chen et al. |
| 2003/0049712 A1 | 3/2003 | Haugwitz |
| 2003/0050453 A1 | 3/2003 | Sorge |
| 2006/0121005 A1 | 6/2006 | Berenson et al. |
| 2007/0065912 A1 | 3/2007 | Carson et al. |
| 2007/0141048 A1 | 6/2007 | Oleksiewicz et al. |
| 2010/0285975 A1 | 11/2010 | Mathies et al. |
| 2010/0310558 A1 | 12/2010 | Oleksiewicz et al. |
| 2012/0015822 A1 | 1/2012 | Weitz et al. |
| 2014/0378345 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0225778 A1 | 8/2015 | Hindson et al. |
| 2015/0298091 A1 | 10/2015 | Weitz et al. |
| 2016/0122817 A1 | 5/2016 | Jarosz et al. |
| 2017/0335391 A1 | 11/2017 | Emerson et al. |
| 2018/0080078 A1 | 3/2018 | Robins et al. |
| 2018/0282808 A1 | 10/2018 | Milla et al. |
| 2019/0008899 A1 | 1/2019 | Moriarity et al. |
| 2019/0025299 A1 | 1/2019 | Vigneault et al. |
| 2019/0040381 A1 | 2/2019 | Thomas et al. |
| 2020/0109195 A1 | 4/2020 | Watkins et al. |
| 2020/0231974 A1* | 7/2020 | Jarvis ..................... C12N 15/64 |
| 2022/0089785 A1 | 3/2022 | Chen et al. |
| 2022/0135641 A1 | 5/2022 | Chen et al. |
| 2022/0389406 A1 | 12/2022 | Chen et al. |

FOREIGN PATENT DOCUMENTS

| | | |
|---|---|---|
| CN | 106103711 A | 11/2016 |
| CN | 106459178 A | 2/2017 |
| CN | 107002076 A | 8/2017 |

(Continued)

OTHER PUBLICATIONS

Hu et al. (Blood, 2018, vol. 132, No. 18, pp. 1911-1921). (Year: 2018).*
Supplemental data of Hu et al. (Year: 2018).*
"Abate, et al., "Corrections and Editorial Expression of Concern", PNAS vol. 104, No. 14 (2010)".
"Abatemarco, et al., "RNA-aptamers-in-droplets (RAPID) high-throughput screening for secretory phenotypes" Nature Communications, 8:332 (2017)".
"Sahin, et al., "Personalized RNA mutanome vaccines mobilize poly-specific therapeutic immunity against cancer" (2017) Nature, p. 1-19".
"Sandberg, et al., "Rapid flow-sorting to simultaneously resolve multiplex massively parallel sequencing products" Scientific Reports (2011)".

(Continued)

*Primary Examiner* — Celine X Qian
(74) *Attorney, Agent, or Firm* — Wilson Sonsini Goodrich & Rosati

(57) ABSTRACT

Provided herein are compositions and methods for assembling nucleic acid sequences encoding T-cell receptors.

30 Claims, 23 Drawing Sheets

Specification includes a Sequence Listing.

(56) References Cited

FOREIGN PATENT DOCUMENTS

| | | |
|---|---|---|
| CN | 107849560 A | 3/2018 |
| EP | 1516929 A2 | 3/2005 |
| EP | 1670912 B1 | 3/2008 |
| EP | 1921144 A2 | 5/2008 |
| EP | 3095879 A1 | 11/2016 |
| WO | WO-2013126712 A1 | 8/2013 |
| WO | WO-2017046201 A1 | 3/2017 |
| WO | WO-2017046205 A1 | 3/2017 |
| WO | WO-2017053902 A1 | 3/2017 |
| WO | WO-2017171631 A1 | 10/2017 |
| WO | WO-2017177217 A2 | 10/2017 |
| WO | WO-2017216324 A1 | 12/2017 |
| WO | WO-2018099402 A1 | 6/2018 |
| WO | WO-2018132739 A2 | 7/2018 |
| WO | WO-2019126466 A1 | 6/2019 |
| WO | WO-2019196088 A1 | 10/2019 |
| WO | WO-2020036875 A1 | 2/2020 |
| WO | WO-2020206238 A2 | 10/2020 |
| WO | WO-2021101956 A1 | 5/2021 |

OTHER PUBLICATIONS

"Anna, et al., "Formation of dispersions using" flow focusing" in microchannels "Applied Physics Letters, vol. 82, No. 3, (2003)".
"Sant, et al., "The Production of 3D Tumor Spheroids for Cancer Drug Discovery" (2017) Drug Discov Today Technology p. 27-36".
"Ayub et al., Advanced Materials Research 1125(2015):84.".
"Battista, et al., "Bioengineering Microgels and Hydrogel Microparticles for Sensing Biomolecular Targets" Gels, 3, 20 (2017)".
"Bethune, et al., "Domain-swapped T cell receptors improve the safety of TCR gene therapy", eLIFE (2016) pp. 1-24".
"Betz K et al., Nat. Chem. Biol. Jul. 2012;8(7):612-4".
"Brenner (2000) Genome Biol.1:1".
"Brenner (2004) Genome Biol. 5:240".
"Brosseau, et al., "Microfluidic Dynamic Interfacial Tensiometry (uDIT)", Royal Societ of Chemistry, 10, 3066-3076 (2014)".
"Browne, et al. "Selection methods for high-procuding mammalian cells lines", TRENDS in Biotechnology vol. 25, No. 9 (2009)".
"Bunse, et al., "RNAi-mediated TCR Knockdown Prevents Auto-immunity in Mice Caused by Mixed TCR Dimers Following TCR Gene Transfer" Molecular Therapy (2014) vol. 22, No. 11, pp. 1983-1991".
"Butler, et al., "Human cell-based artificial antigen-presenting cells for cancer immunotherapy" (2014) Immunological Reviews, vol. 257: 191-209".
"Cao, et al., "Comprehensive single cell transcriptional profiling of a multicellular organism by combinatorial indexing", (2017) University of Washinton pp. 1-35".
"Chomczynski, et al., "Alkaline polyethylene glycol-based method for direct PCT from bacteria, eukaryotic tissue samples, and whole blood" BioTechniques 40: 454-458 (2016)".
"Cochran, et al., "A diverse set of oligomeric class II MHC-peptide complexes for probing T-cell receptor interactions" Chemistry & Biology (2000) vol. 7, No. 9".
"Cusanovich, et al., "Multiplex Single Cell Profiling of Chromatin Accessibility by Combinatorial Cellular Indexing" Science 348(6237) pp. 910-914 (2015)".
"De Simone, et al. "Single Cell T Cell Receptor Sequencing: Techniques and Future Challenges" (2018) Frontiers in Immunology, p. 1-7".
"DeJournette, et al., "Creating Biocompatible Oil-Water Interfaces without Synthesis: Direct Interactions bettween Primary Amines and Carboxylated Perfluorocarbon Surfactants" Anal Chem (2013) 85, 10556-10564".
"Eason et al. (2004) Proc. Natl. Acad. Sci. USA 101:11046;".
"Eyer, et al., "Single-cell deep phenotyping of IgG-secreting cells for high-resolution immune monitoring" Nature Biotechnology (2017)".
"Eyer, et al., "Supplementary Notes" Nature Biotechnology (2017), pp. 1-35".
"Geng, et al., "Single-Cell Forensic Short Tandem Repeat Typing within Microfluidic Droplets", Anal. Chem (2014)".
"Geng, et al., "Minimizing inhibition of PCT-STR typing using digital agarose droplet microfluidics" Forensic Scinece International: Genetics 14 (2015) 203-209".
"Giaever et al. (2004) Proc. Natl. Acad. Sci. USA 101:793;".
"Henikofff, et al., "Amino acid substitution matrices from protein blocks" (1992) Proc. Natl. Acad. Sci, vol. 89, p. 10915-10919".
"Hongkai Zhang et al., Chemistry & biology 20(5):734-741, May 2013".
"International Search Report and Written Opinion for corresponding PCT Application No. PCT/US2018/066748 dated Mar. 18, 2019".
"International Search Report and Written Opinion for corresponding PCT Application No. PCT/US/2019/046170 dated Dec. 3, 2019".
"International Search Report and Written Opinion for corresponding PCT Application No. PCT/US/2020/026558 dated Oct. 1, 2020".
"International Search Report and Written Opinion for corresponding PCT Application No. PCT/US2020/060998 dated Mar. 11, 2021".
"International Search Report and Written opinion for PCT Application No. PCT/US2020/060998 dated Mar. 11, 2021".
International Search Report and Written Opinion for PCT Application No. PCT/US2020/06558 dated Oct. 1, 2020.
"Ismagilov, et al., "Reactions in Droplets in Microfluidic channels" Angew. Chem. Ed. 45, p. 7336-7356 (2006)".
"Jelena Skuljec et al., Front Immunol. 2017; 8:1125".
"Skhiri, et al., "Dynamics of molecular trnasport by surfactants in emulsions", Soft Matter (2012)".
"Kim, et al., "Single-cell RT-PCT in microfluidic droplets with integrated chemical lysis" Anal. Chem (2017)".
"Klein, et al., "Droplet Barcoding for Single-Cell Transcriptomics Applied to Embryonic Stem Cells", Cell 161, 1187-1201 (2015)".
"Klein, et al., "Multiplex pairwise assembly of array-derived DNA oligonucleotides" Nucleic Acides Research, (2016), vol. 44, No. 5 pp. 1-10".
"Kojima et al., Chem Mater 10(1998):3429,".
"Kreiter, et al. "Increased Antigen Presentation Efficiency by Coupling Antigens to MHC Class I Trafficking Signals" (2008) J Immunol 180:309-318".
"Kuball, et al., "Facilitating matched pairing and expression of TCR chains introduced into human T cells" Blood, (2007) vol. 109, No. 6".
"Kumar et al. (2001) Nature Rev. 2:302;".
"Lagus, et al., "A review of the theory, methods and recent applications of high-throughput single-cell droplet microfluidics", J. Phys. D: Appl. Phys. 46 (2013)".
"Liau, et al., "Mixing Crowded Biological Solutions in Milliseconds" Ana. Chem., 77, 7618-7625 (2005)".
"Liu, et al., "Shape-controlled Production of Biodegradable Calcium Alginate Gel Microparticles Using a Novel Microfluidic Device" Langmuir (2006) 22, 9453-9457".
"Lorenz, FKM et al.) Unbiased Identification of T-Cell Receptors Targeting Immunodominant Peptide-MHC Complexes for T-Cell Receptor Immunotherapy. Human Gene Therapy. Sep. 26, 2017; vol. 28, No. 12;".
"Lu, et al., "An Efficient Single-Cell RNA-Seq Approach to Identify Neoantigen-Specific T Cell Receptors" (2018) Molecular Therapy, vol. 26, No. 2 p. 379-389".
"Mahal et al., (1997) Science 276:1125-1128)".
"Mazutis, et al., "Single-cell analysis and sorting using droplet-based microfluidics" Nature Protocols, vol. 8, No. 5 pp. 870-891 (2013)".
"Mazutis, et al., "Microfluidic Production of Alginate Hydrogel Particles for Antibody Encapsulation and Release" Macromolecular Bioscience, p. 1-6 (2015)".
"Nguyen, et al., "Bioactive factor delivery strategies from engineered polymer hydrogels for therapeutic medicine" Pro Polym Sci 39(7), pp. 1236-1265, (2014)".
"Novak, et al., "Single-Cell Multiplex Gtene Detection and Sequencing with Microfluidically Generated Agarose Emulsions" Angew. Chem. Int. Ed., 50, pp. 390-395 (2011)".

(56) References Cited

OTHER PUBLICATIONS

"Song, et al., "A Microfluidic System for Controlling Reaction Networks in Time", Angew. Chem. Int. 42, No. 7 pp. 767-772 (2003)".
"Ottino, et al., "Designing Optimal Micromixers" Science vol. 305 pp. 485-486 (2004)".
"Pasetto, et al., "Tumor-an Neoantigen-Reactive T-cell Receptors Can be Identified Based on Their Frequency in Fresh Tumor" (2016) Cancer Immunology Research 4(9) p. 734-744".
"Pawer and Edgar, Biomaterials 33(2012), 3279".
"Provasi, et al., "Editing T cell specificity towwards leukemia by zinc finger nucleases and lentiviral gene transfer" Nature Medicine (2012) vol. 18, No. 5".
"Redmond, et al., "Singe-cell TCRseq: paired recovery of entire T-cell alpha and beta chain transcripts in T-cell receptors from single-cell RNAseq" Genome Medicine (2016) pp. 1-12".
"Rosskopf, et al., "A Jurkat 76 based triple parameter reporter system to evaluate TCR funcations and adoptive T cells strategies" (2018) Oncotarget, vol. 9 (No. 25) pp. 17608-17619".
"Tice, et al., "Formation of Droplets and Mixing in Multiphase Microfluidics at Low values of the Reynolds and the Capillary Numbers", Langmuir 19, pp. 9127-9133 (2003)".
"Uckert, et al., "TCR transgenes and transgene cassettes for TCR gene therapy: status in 2008" Cancer Immunol Immunother (2009) 58: 809-822".
"U.S. Appl. No. 62/609,756, filed Dec. 17, 2017".
"U.S. Appl. No. 62/674,214, filed May 26, 2018".
"Walseng, et al., "A TCR-based Chimeric Antigen Receptor" Scientific Reports (2017) 7:10713".
"Ward, et al., "Microfluidic flow focusing: Drop size and scalling in pressure versus flow-rate-driven pumping" Electrophoresis, 26, pp. 3716-3724 (2005)".
"Wetmur, et al., "Molecular haplotyping by linking emulsion PCT: analysis of paraoxonase 1 haplotypes and phenotypes", Nucleic Acids Research (2005) vol. 33, No. 8 pp. 2615-2619".
"Winzeler et al. (1999) Science 285:901;".
"Yang, et al., "Fluid mixing in droplet-based microfluidics with T junction and convergent-divergent sinusoidal microchannels" Electrophoresis, 39, pp. 512-520 (2018)".
"Zhang, et al., "Lab on a Chip", Manuscript, Royal Society of Chemistry, (2016)".
Zilionis et al. Single-cell barcoding and sequencing using droplet microfluidics, Nature Protocols, 12(1) 2017: 44.
"Zucca, Agarose and Its Derivatives as Supports for Enzyme Immobilization, Molecules 2016, 21, 1577".
Aug. 16, 2021 Non-Final Office Action U.S. Appl. No. 17/173,705.
EP Application No. 19849196.1 Extended European Search Report dated Jun. 3, 2022.
International Preliminary Report on Patentability dated May 17, 2022 for International Application No. PCT/US2020/060998.
Patten et al.: Transfer of putative complementarity-determining region loops of T cell receptor V domains confers toxin reactivity but not peptide/MHC specificity. J Immunol. 150(6):2281-2294 (1993).
Song, I. et al., "Broad TCR repertoire and diverse structural solutions for recognition of an immunodominant CD8+ T cell epitope", Nature Structural & Molecular Biology, 2017, vol. 24, No. 4, pp. 395-409.
Laydon, D. et al, "Estimating T-cell repertoire diversity: limitations of classical estimators and a new approach", Philosophical Transactions Royal Society of London B:Biological Sciences, 2015, vol. 370, No. 20140291, pp. 1-16.
Marrack, P. et al., "The somatically generated portion of T cell receptor CDR3a contributes to the MHC allele specificity of the T cell receptor", eLife, 2017, vol. 6, No. e30918, pp. 1-27.
Rosati et al, "Overview of methodologies for T-cell receptor repertoire analysis", BMC Biotechnology, 2017, vol. 17, No. 61, pp. 1-16.
European Patent Application No. 20782656.1 Extended European Search Report dated Nov. 25, 2022.

\* cited by examiner

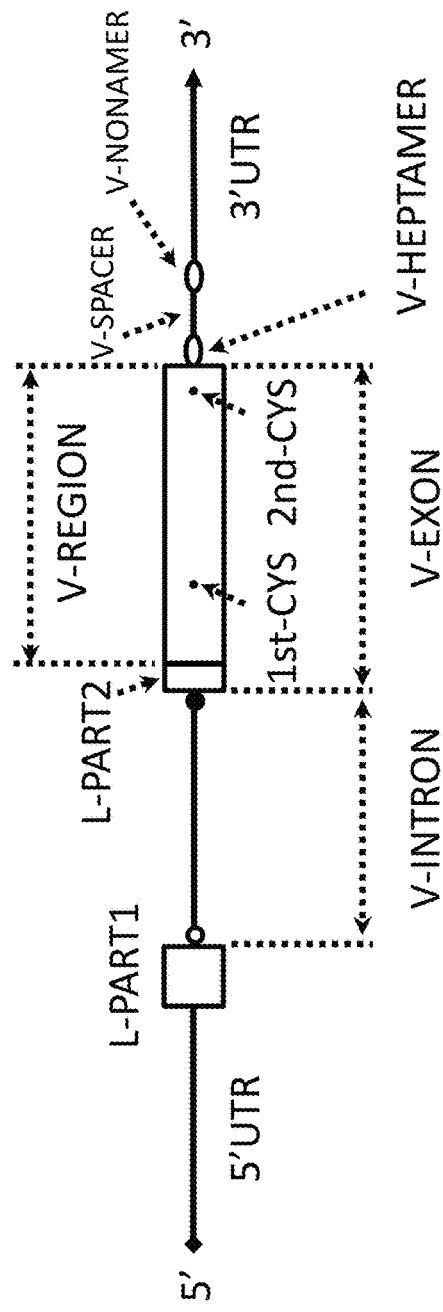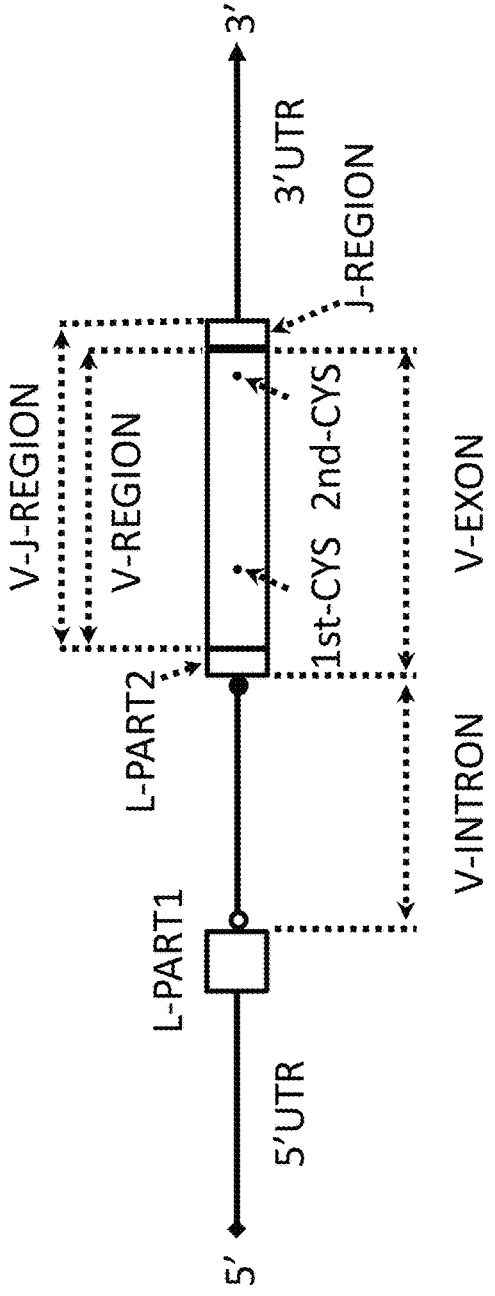
FIG. 4A
FIG. 4B

COMPOSITIONS AND METHODS FOR T-CELL RECEPTOR GENE ASSEMBLY

CROSS-REFERENCE

This application is a continuation of U.S. patent application Ser. No. 17/493,469, filed Oct. 4, 2021, which is a continuation of International Application No. PCT/US20/26558, filed Apr. 3, 2020, which claims the benefit of U.S. Provisional Patent Application No. 62/829,813, filed Apr. 5, 2019, U.S. Provisional Patent Application No. 62/838,465, filed Apr. 25, 2019, U.S. Provisional Patent Application No. 62/898,053, filed Sep. 10, 2019, and U.S. Provisional Patent Application No. 62/972,231, filed Feb. 10, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 16, 2021, is named 53563_705_302 SL.txt and is 69,258 bytes in size.

BACKGROUND OF THE INVENTION

The T-cell receptor (TCR) can be responsible for the recognition of the antigen-major histocompatibility complex, leading to the initiation of an inflammatory response. Many T cell subsets exist, including cytotoxic T cells and helper T cells. Cytotoxic T cells (also known as CD8+ T cells) kill abnormal cells, for example virus-infected or tumor cells. Helper T cells (also known as CD4+ T cells) aid in the activation and maturation of other immune cells. Both cytotoxic and helper T cells carry out their function subsequent to the recognition of specific target antigens which triggers their respective responses. The antigen specificity of a T cell can be defined by the TCR expressed on the surface of the T cell. T-cell receptors are heterodimer proteins composed of two polypeptide chains, most commonly an alpha chain and a beta chain, but a minority of T cells can express a gamma and delta chain. The specific amino acid sequence of the TCR and the resultant three-dimensional structure defines the TCR antigen specificity and affinity. The amino acid and coding DNA sequences of the TCR chains for any individual T cell are almost always unique or at very low abundance in an organism's entire TCR repertoire, since there are a vast number of possible TCR sequences. This large sequence diversity can be achieved during T cell development through a number of cellular mechanisms and may be a critical aspect of the immune system's ability to respond to a huge variety of potential antigens.

Analyzing the TCR repertoire may help to gain a better understanding of the immune system features and of the aetiology and progression of diseases, in particular those with unknown antigenic triggers. The extreme diversity of the TCR repertoire and the bipartite nature of TCRs can represent a major analytical challenge. High-throughput sequencing can allow greater sequencing depth and significantly more accurate quantification of TCR clonotype abundance, albeit at a greater expense than spectratyping.

SUMMARY OF THE INVENTION

Provided herein are compositions and methods to assemble nucleic acid sequences encoding natively paired T-cell receptors (TCRs) (or cognate TCR pairs). For example, a TCR can comprise a TCR alpha chain and a TCR beta chain or a TCR can comprise a TCR gamma chain and a TCR delta chain. Sequences encoding natively paired TCRs can be identified using various methods, including but not limited to using single cell barcoding and sequencing technologies. After obtaining the sequences encoding natively paired TCRs, compositions and methods described herein can be used to construct or assemble one or more nucleic acid sequences to express the natively paired TCRs in any given host cell(s) in a quick, high-throughput and cost-effective manner. The one or more nucleic acid sequences can comprise greater than or equal to about 1, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences encoding different TCRs.

In an aspect, the present disclosure provides a method for generating a nucleic acid molecule encoding a T-cell receptor (TCR) chain or portion thereof, comprising: (a) providing at least one nucleic acid molecule comprising a sequence encoding a CDR3 of a TCR chain; (b) providing a plurality of nucleic acid molecules, each nucleic acid molecule of the plurality comprising a sequence derived from a TCR V gene, wherein the plurality of nucleic acid molecules comprises at least two different sequences derived from at least two different TCR V genes; and (c) contacting the at least one nucleic acid molecule of (a) to the plurality of nucleic acid molecules of (b) in a same compartment, wherein the at least one nucleic acid molecule of (a) is capable of linking to a nucleic acid molecule of the plurality of nucleic acid molecules to generate a third nucleic acid molecule comprising the sequence encoding the CDR3 and a sequence derived from one of the at least two different TCR V genes, thereby generating the nucleic acid molecule encoding the TCR chain or portion thereof. In some embodiments, the at least one nucleic acid molecule comprises at least about 2, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences. In some embodiments, the plurality of nucleic acid molecules, each nucleic acid molecule of the plurality comprising a sequence derived from a TCR V gene, comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more different sequences derived from different TCR V genes.

In some embodiments, the at least one nucleic acid molecule comprises a first plurality of nucleic acid molecules, wherein each nucleic acid molecule of the first plurality of nucleic acid molecules comprises a sequence encoding a CDR3 of a TCR chain. In some embodiments, the at least one nucleic acid molecule of (a) is capable of specifically linking to a nucleic acid molecule of the plurality of nucleic acid molecules that comprises a sequence derived from any single given TCR V gene of the at least two different TCR V genes. In some embodiments, the at least one nucleic acid molecule further comprises a J region of the TCR chain. In some embodiments, each nucleic acid molecule of the first plurality of nucleic acid molecules further comprises a J region of a TCR chain. In some embodiments, the at least two TCR V genes are human TCR V genes or mouse TCR V genes. In some embodiments, the at least two TCR V genes are selected from the group consisting of a human TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, and TRAV41. In some embodiments, the at least two TCR V genes are selected from the group consisting of a human TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, and TRBV30. In some embodiments, each sequence of the plurality of sequences derived from the at least two different TCR V genes comprises a sequence encoding L-PART1, L-PART2, FR1, CDR1, FR2, CDR2, and/or FR3. In some embodiments, the TCR chain is a TCR alpha chain, a TCR beta chain, a TCR gamma chain, or a TCR delta chain. In some embodiments, the at least one nucleic acid molecule further comprises an additional sequence encoding an additional CDR3 of an additional TCR chain. In some embodiments, the at least one nucleic acid molecule comprises an additional J region of the additional TCR chain. In some embodiments, the sequence encoding the CDR3 and the additional sequence encoding the additional CDR3 are separated by at most 100 nucleotides. In some embodiments, the TCR chain and the additional TCR chain are a cognate pair of TCR chains. In some embodiments, the at least one nucleic acid molecule comprises a connector sequence, which connector sequence is capable of linking the at least one nucleic acid molecule to the nucleic acid molecule of the plurality of nucleic acid molecules to generate the third nucleic acid molecule. In some embodiments, the at least one nucleic acid molecule and the nucleic acid molecule of the plurality of nucleic acid molecules encodes a functional TCR chain or portion thereof. In some embodiments, the nucleic acid molecule of the plurality of nucleic acid molecules comprises an anti-connector sequence, which anti-connector sequence is complementary to the connector sequence of the at least one nucleic acid molecule of (a). In some embodiments, the method further comprises linking the at least one nucleic acid molecule of (a) and the nucleic acid molecule of the plurality of nucleic acid molecules of (b). In some embodiments, linking comprises hybridizing the at least one nucleic acid molecule of (a) and the nucleic acid molecule of the plurality of nucleic acid molecules of (b). In some embodiments, hybridizing comprises hybridizing the connector sequence of the at least one nucleic acid molecule of (a) with the anti-connector sequence of the nucleic acid molecule of the plurality of nucleic acid molecules of (b). In some embodiments, the method further comprises (i) extending a free 3' end of the nucleic acid molecule of the plurality of nucleic acid molecules using the at least one nucleic acid molecule of (a) as a template, and/or (ii) extending a free 3' end of the at least one nucleic acid molecule of (a) using the nucleic acid molecule of the plurality of nucleic acid molecules as a template, to generate the third nucleic acid molecule. In some embodiments, the method further comprises ligating the at least one nucleic acid molecule of (a) and the nucleic acid molecule of the plurality of nucleic acid molecules (b). In some embodiments, the method further comprises contacting the third nucleic acid molecule with a restriction enzyme to generate a sticky end. In some embodiments, the method further comprises contacting the third nucleic acid molecule with an additional nucleic acid molecule. In some embodiments, the additional nucleic acid molecule encodes a constant region or portion thereof of a TCR chain. In some embodiments, the method further comprises ligating the third nucleic acid molecule and the additional nucleic acid molecule. In some embodiments, a plurality of nucleic acid molecules, each encoding a different TCR chain or portion thereof, are generated in the same compartment. In some embodiments, at least five different nucleic acid molecules of the plurality of nucleic acid molecules are generated in the same compartment. In some embodiments, at least ten different nucleic acid molecules of the plurality of nucleic acid molecules are generated in the same compartment. In some embodiments, at least 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different nucleic acid molecules of the plurality of nucleic acid molecules are generated in the same compartment. In some embodiments, the same compartment is a well, a tube, or a droplet. In some embodiments, the at least one nucleic acid molecule comprises a unique barcode. In some embodiments, the unique barcode is a primer binding site. In some embodiments, the connector sequence comprises a unique barcode. In some embodiments, the unique barcode is a primer binding site.

In another aspect, the present disclosure provides a composition comprising (a) a plurality of nucleic acid molecules, wherein each nucleic acid molecule of the plurality of nucleic acid molecules comprises a sequence derived from a T-cell receptor (TCR) V gene and does not comprise a CDR3 sequence, wherein a first nucleic acid molecule of the plurality comprises a first anti-connector sequence and a second nucleic acid molecule of the plurality comprises a second anti-connector sequence, wherein the first anti-connector sequence is different from the second anti-connector sequence, and wherein the sequence derived from a TCR V gene of the first nucleic acid molecule and the second nucleic acid molecule are derived from a different TCR V gene; and (b) at least one nucleic acid molecule comprising a sequence encoding a CDR3 of a TCR chain, wherein the at least one nucleic acid molecule further comprises a first connector sequence complementary to the first anti-connector sequence.

In some embodiments, the composition is a liquid composition. In some embodiments, the plurality of nucleic acid molecules of (a) and the at least one nucleic acid molecule of (b) are in a same compartment. In some embodiments, the sequence derived from the TCR V gene comprises at least ten nucleotides of the TCR V gene. In some embodiments, the TCR V gene is a TRAV gene, a TRBV gene, a TRGV gene, or a TRDV gene. In some embodiments, the sequence derived from the TCR V gene comprises a sequence encoding L-PART1, L-PART2, FR1, CDR1, FR2, CDR2, and/or FR3. In some embodiments, the at least one nucleic acid molecule further comprises a J region of the TCR chain. In some embodiments, the at least one nucleic acid molecule further comprises an additional sequence encoding an additional CDR3 of an additional TCR chain. In some embodiments, the at least one nucleic acid molecule further comprises an additional J region of the additional TCR chain. In some embodiments, the sequence encoding the CDR3 and the additional sequence encoding the CDR3 are separated by at most 100 nucleotides. In some embodiments, the TCR chain and the additional TCR chain are a cognate pair of TCR chains. In some embodiments, the at least one nucleic acid molecule of (b) comprises a first plurality of nucleic acid molecules, and wherein each nucleic acid molecule of the first plurality of nucleic acid molecules comprises a sequence encoding a CDR3 of a TCR chain. In some embodiments, each nucleic acid molecule of the first plurality of nucleic acid molecules encodes a different CDR3 of a different TCR chain. In some embodiments, each nucleic acid molecule of the first plurality of nucleic acid molecules comprises a different connector sequence, which different connector sequence is capable of specifically linking to a nucleic acid molecule of the plurality of nucleic acid molecules that comprises a sequence derived from any single given TCR V gene. In some embodiments, the first anti-connector sequence or the second anti-connector sequence comprises a TCR V gene sequence. In some embodiments, the TCR V gene sequence comprises at least three nucleotides of the TCR V gene adjacent to a sequence encoding a CDR3 in a rearranged gene. In some embodiments, the first anti-connector sequence or the second anti-connector sequence comprises a pre-determined sequence. In some embodiments, the first connector sequence hybridizes to the first anti-connector sequence. In some embodiments, the at least one nucleic acid molecule of (b) comprises a unique barcode. In some embodiments, the unique barcode is a primer binding site. In some embodiments, the first connector sequence of the at least one nucleic acid molecule comprises a unique barcode. In some embodiments, the unique barcode is a primer binding site.

In another aspect, the present disclosure provides a method for generating a plurality of nucleic acid molecules, comprising: providing a first plurality of nucleic acid molecules, wherein a nucleic acid molecule of the first plurality of nucleic acid molecules comprises a sequence encoding a first CDR3 of a first T-cell receptor (TCR) chain and a second CDR3 of a second TCR chain, wherein the first CDR3 and the second CDR3 are from a cognate pair of TCR chains; providing a second plurality of nucleic acid molecules, wherein a nucleic acid molecule of the second plurality of nucleic acid molecules comprises a sequence derived from a TCR V gene, wherein the nucleic acid molecule does not comprise a sequence encoding a constant domain; and contacting the first plurality of nucleic acid molecules and the second plurality of nucleic acid molecules, wherein the nucleic acid molecule of the first plurality of nucleic acid molecules links with the nucleic acid molecule of the second plurality of nucleic acid molecules to form a nucleic acid molecule comprising the sequence encoding the first CDR3 and the second CDR3 and the sequence derived from the TCR V gene, wherein the sequence encoding the first CDR3 and the second CDR3 and the TCR V gene are derived from the cognate pair of TCR chains.

In some embodiments, each nucleic acid molecule of the first plurality of nucleic acid molecules comprises a sequence encoding a different first CDR3 of a first TCR chain and/or a different CDR3 of a second TCR chain. In some embodiments, the first plurality of nucleic acid molecules comprises at least about 2, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences. In some embodiments, each nucleic acid molecule of the second plurality of nucleic acid molecules comprises a sequence derived from a different TCR V gene. In some embodiments, the second plurality of nucleic acid molecules comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more different TCR V genes. In some embodiments, the first plurality of nucleic acid molecules and the second plurality of nucleic acid molecules are contacted in a same compartment. In some embodiments, the nucleic acid molecule of the first plurality of nucleic acid molecules further comprises a connector sequence, wherein the connector sequence links the nucleic acid molecule of the first plurality of nucleic acid molecules and the nucleic acid molecule of the second plurality of nucleic acid molecules. In some embodiments, the nucleic acid molecule of the second plurality of nucleic acid molecules further comprises an anti-connector sequence, which anti-connector sequence is complementary to the connector sequence. In some embodiments, the connector sequence hybridizes to the anti-connector sequence to link the nucleic acid molecule of the first plurality of nucleic acid molecules and the nucleic acid molecule of the second plurality of nucleic acid molecules. In some embodiments, the connector sequence is codon-diversified such that the connector sequence of the nucleic acid molecule of the first plurality of nucleic acid molecules is different from other connector sequences of other nucleic acid molecules of the first plurality of nucleic acid molecules. In some embodiments, the nucleic acid molecule of the first plurality of nucleic acid molecules further comprises a first J region of the first TCR chain and/or a second J region of the second TCR chain. In some embodiments, (i) the first TCR chain is a TCR alpha chain and the second TCR chain is a TCR beta chain or (ii) the first TCR chain is a TCR gamma chain and the second TCR chain is a TCR delta chain. In some embodiments, the TCR V gene is a TRAV gene, a TRBV gene, a TRGV gene, or a TRDV gene. In some embodiments, the nucleic acid molecule of the second plurality of nucleic acid molecules is a double-stranded nucleic acid molecule. In some embodiments, the nucleic acid molecule of the second plurality of nucleic acid molecules further comprises a sequence encoding a portion of a self-cleaving peptide. In some embodiments, the anti-connector sequence is an overhang of the nucleic acid molecule of the second plurality of nucleic acid molecules. In some embodiments, the connector sequence or the anti-connector sequence is at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, or more nucleotides in length. In some embodiments, the method further comprises (i) extending a 3' end of the nucleic acid molecule of the first plurality of nucleic acid molecules hybridized thereto with the nucleic acid molecule of the second plurality of nucleic acid molecules and/or (ii) extending a 3' end of the nucleic acid molecule of the second plurality of nucleic acid molecules hybridized thereto with the nucleic acid molecule of the first plurality of nucleic acid molecules. In some embodiments, the method further comprises ligating the nucleic acid molecule of the first plurality of nucleic acid molecules with the nucleic acid molecule of the second plurality of nucleic acid molecule.

In some embodiments, the method further comprises contacting the nucleic acid molecule comprising the sequence encoding the first CDR3 and the second CDR3 and the sequence derived from the TCR V gene with a restriction enzyme to generate a sticky end. In some embodiments, the method further comprises contacting the nucleic acid molecule comprising the sequence encoding the first CDR3 and the second CDR3 and the sequence derived from the TCR V gene with an additional nucleic acid molecule comprising a sequence encoding a constant region or portion thereof. In some embodiments, the method further comprises ligating the nucleic acid molecule comprising the sequence encoding the first CDR3 and the second CDR3 and the sequence derived from the TCR V gene with the additional nucleic acid molecule through the sticky end. In some embodiments, the sequence encoding the first CDR3 and the second encoding the second CDR3 are separated by at most about 100, 90, 80, 70, 60, 50, 40, 30, 20, 10, or 5 nucleotides. In some embodiments, the sequence derived from the TCR V gene comprises a sequence encoding FR1, CDR1, FR2, CDR2, and FR3. In some embodiments, the sequence derived from the TCR V gene comprises a sequence encoding L-PART1, L-PART2, FR1, CDR1, FR2, CDR2, and FR3.

In another aspect, the present disclosure provides a composition comprising: a first plurality of nucleic acid molecules, wherein each nucleic acid molecule of the first plurality of nucleic acid molecules comprises a sequence encoding a first CDR3 of a first T-cell receptor (TCR) chain and a second CDR3 of a second TCR chain, wherein the first CDR3 and the second CDR3 are from a cognate pair of TCR chains; and a second plurality of nucleic acid molecules, wherein each nucleic acid molecule of the second plurality of nucleic acid molecules comprises a sequence derived from a TCR V gene, and wherein each nucleic acid molecule of the second plurality of nucleic acid molecules does not comprise a sequence encoding the first CDR3 and the second CDR3; wherein (i) each nucleic acid molecule of the first plurality of nucleic acid molecules comprises a sequence encoding a different first CDR3 and/or second CDR3, and/or (ii) each nucleic acid molecule of the second plurality of nucleic acid molecules comprises a sequence derived from a different TCR V gene. In some embodiments, the first plurality of nucleic acid molecules comprises at least about 2, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100, 000, 1,000,000, 10,000,000, or more different sequences. In some embodiments, the second plurality of nucleic acid molecules comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more different TCR V genes.

In some embodiments, each nucleic acid molecule of the first plurality of nucleic acid molecules further comprises a connector sequence, wherein a given connector sequence is usable to link a given nucleic acid molecule of the first plurality of nucleic acid molecules and a given nucleic acid molecule of the second plurality of nucleic acid molecules. In some embodiments, each nucleic acid molecule of the second plurality of nucleic acid molecules further comprises an anti-connector sequence, which anti-connector sequence is complementary to the connector sequence. In some embodiments, the connector sequence is codon-diversified such that the given connector sequence of the given nucleic acid molecule of the first plurality of nucleic acid molecules is different from other connector sequences of other nucleic acid molecules of the first plurality of nucleic acid molecules. In some embodiments, the connector sequence encodes an amino acid sequence. In some embodiments, the connector sequence is in frame with the sequence encoding the first CDR3 of the first TCR chain and the second CDR3 of the second TCR chain. In some embodiments, the connector sequence comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, or more nucleotides. In some embodiments, the connector sequence comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, or more nucleotides of the TCR V gene adjacent to the sequence encoding the first CDR3 of the first TCR chain or the second CDR3 of the second TCR chain. In some embodiments, a given amino acid sequence encoded by the given connector sequence is the same or substantially the same as at least one other amino acid sequence encoded by at least one other connector sequence. In some embodiments, a given amino acid sequence encoded by the given connector sequence is different from other amino acid sequences encoded by other connector sequences. In some embodiments, each nucleic acid molecule of the first plurality of nucleic acid molecules further comprises a first J region of the first TCR chain and/or a second J region of the second TCR chain. In some embodiments, the composition is a liquid composition. In some embodiments, the first plurality of nucleic acid molecules and the second plurality of nucleic acid molecules are within a same compartment. In some embodiments, the given nucleic acid molecule of the first plurality of nucleic acid molecules is linked to the given nucleic acid molecule of the second plurality of nucleic acid molecules through the given connector sequence. In some embodiments, the given nucleic acid molecule of the first plurality of nucleic acid molecules hybridizes to the given nucleic acid molecule of the second plurality of nucleic acid molecules through the given connector sequence hybridized to a given anti-connector sequence. In some embodiments, the sequence encoding the first CDR3 and the sequence encoding the second CDR3 are separated by at most 100 nucleotides. In some embodiments, the sequence derived from the TCR V gene comprises a sequence encoding FR1, CDR1, FR2, CDR2, and FR3. In some embodiments, the sequence derived from the TCR V gene comprises a sequence encoding L-PART1, L-PART2, FR1, CDR1, FR2, CDR2, and FR3. In some embodiments, each nucleic acid molecule of the first plurality of nucleic acid molecules or the second plurality of molecules is chemically synthesized. In some embodiments, each nucleic acid molecule of the first plurality of nucleic acid molecules is at most about 250, 240, 230, 220, 210, 200, 190, 180, 170, 160, 150, 140, 130, 120, 110, 100, or 50 nucleotides long.

In another aspect, the present disclosure provides a composition comprising a plurality of nucleic acid molecules, each nucleic acid molecule of the plurality of nucleic acid molecules comprising a sequence derived from a T-cell receptor (TCR) V gene sequence, wherein the plurality of nucleic acid molecules comprises a first nucleic acid molecule having a first connector sequence and a second nucleic acid molecule having a second connector sequence, wherein the first connector sequence is different from the second connector sequence.

In some embodiments, each nucleic acid molecule of the plurality of nucleic acid molecules comprises a sequence derived from a different TCR V gene. In some embodiments, each nucleic acid molecule of the plurality of nucleic acid molecules comprises a different connector sequence. In some embodiments, each nucleic acid molecule of the plurality of nucleic acid molecules does not comprise a sequence encoding a CDR3 of a TCR chain. In some embodiments, each nucleic acid molecule of the plurality of nucleic acid molecules does not comprise a sequence encoding a constant domain of a TCR chain. In some embodiments, the sequence derived from the TCR V gene comprises at least 10, 20, 30, 50, 60, 70, 80, 90, 100, 200, 300, 400, 500, 600, 700, 800, 900, 1000, or more nucleotides of the TCR V gene. In some embodiments, the TCR V gene is a TRAV gene, a TRBV gene, a TRGV gene, or a TRDV gene.

In another aspect, the present disclosure provides a composition comprising a plurality of nucleic acid molecules, each nucleic acid molecule of the plurality of nucleic acid molecules encoding a CDR3 or a portion thereof of a T-cell receptor (TCR) chain, wherein the plurality of nucleic acid molecules comprises a first nucleic acid molecule having a first connector sequence and a second nucleic acid molecule having a second connector sequence, wherein the first connector sequence is different from the second connector sequence.

In some embodiments, each nucleic acid molecule of the plurality of nucleic acid molecules further comprises a J region of a TCR chain. In some embodiments, each nucleic acid molecule of the plurality of nucleic acid molecules encodes a first CDR3 or a portion thereof of a first TCR chain and a second CDR3 or a portion thereof of a second TCR chain. In some embodiments, each nucleic acid molecule of the plurality of nucleic acid molecules further comprises a first J region of a first TCR chain and a second J region of a second TCR chain. In some embodiments, each nucleic acid molecule of the plurality of nucleic acid molecules encodes a different CDR3 or a portion thereof of a different TCR chain. In some embodiments, each nucleic acid molecule of the plurality of nucleic acid molecules comprises a different connector sequence. In some embodiments, each nucleic acid molecule of the plurality of nucleic acid molecules does not comprise greater than 200, 150, 100, 80, 50, 40, 30, 20, or 10 nucleotides TCR V gene. In some embodiments, each nucleic acid molecule of the plurality of nucleic acid molecules does not comprise a sequence encoding a constant domain of a TCR chain. In some embodiments, the first connector sequence or the second connector sequence comprises a sequence derived from a TCR V gene. In some embodiments, the sequence derived from the TCR V gene comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, or more nucleotides of the TCR V gene adjacent to a sequence encoding a CDR3 in a rearranged gene. In some embodiments, the first connector sequence or the second connector sequence comprises a pre-determined sequence. In some embodiments, the first connector sequence or the second connector sequence comprises a sequence complementary to a TCR V gene sequence. In some embodiments, the composition further comprises a second plurality of nucleic acid molecules, each nucleic acid molecule of the second plurality of nucleic acid molecules comprising a sequence derived from a TCR V gene. In some embodiments, a first nucleic acid molecule of the second plurality comprises a first anti-connector sequence, which first anti-connector sequence is complementary to the first connector sequence. In some embodiments, a second nucleic acid molecule of the second plurality comprises a second anti-connector sequence, which second anti-connector sequence is complementary to the second connector sequence. In some embodiments, the first anti-connector sequence of the first nucleic acid molecule of the second plurality is linked to the first connector sequence of the first nucleic acid molecule of the first plurality. In some embodiments, the second anti-connector sequence of the second nucleic acid molecule of the second plurality is linked to the second connector sequence of the second nucleic acid molecule of the first plurality.

In another aspect, the present disclosure provides a composition comprising a plurality of nucleic acid molecules, each comprising a sequence encoding at least ten amino acids (e.g., in some cases, encoding at least about 10, 15, 20, 25, 30, 35, 40, 45, 50, 100, 200, or more amino acids) of a T-cell receptor (TCR) chain, wherein the plurality of nucleic acid molecules comprises a first nucleic acid molecule having a first connector sequence and a second nucleic acid molecule having a second connector sequence, wherein the first connector sequence is different from the second connector sequence, wherein the first connector sequence or the second connector sequence encodes a portion of a TCR chain and wherein the first connector sequence or the second connector sequence is in frame with the sequence encoding at least ten (e.g., in some cases, encoding at least about 10, 15, 20, 25, 30, 35, 40, 45, 50, 100, 200, or more amino acids) amino acids of a TCR chain.

In some embodiments, the first connector sequence or the second connector sequence comprises at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, or more contiguous nucleotides of a TCR chain gene and is in frame with the sequence encoding at least ten amino acids of a TCR chain. In some embodiments, the first connector sequence and the second connector sequence encodes at least two contiguous amino acids of a TCR chain. In some embodiments, the TCR chain of the portion of the TCR chain and the TCR chain encoded by the sequence encoding at least ten amino acids is the same. In some embodiments, each nucleic acid molecule of the plurality of nucleic acid molecules comprises a sequence derived from a TCR V gene. In some embodiments, each nucleic acid molecule of the plurality of nucleic acid molecules encodes a CDR3 or portion thereof of the TCR chain. In some embodiments, each nucleic acid molecule of the plurality of nucleic acid molecules further comprises a J region of the TCR chain. In some embodiments, each nucleic acid molecule of the plurality of nucleic acid molecules encodes a first CDR3 or portion thereof of a first TCR chain and a second CDR3 or portion thereof of a second TCR chain. In some embodiments, each nucleic acid molecule of the plurality of nucleic acid molecules further comprises a first J region of a first TCR chain and a second J region of a second TCR chain. In some embodiments, a sequence encoding the first CDR3 or portion thereof and a sequence encoding the second CDR3 or portion thereof are separated by at most 100, 90, 80, 70, 60, 50, 40, 30, 20, 10, or 5 nucleotides. In some embodiments, the first connector sequence or the second connector sequence comprises a sequence derived from a TCR V gene. In some embodiments, the first connector sequence or the second connector sequence comprises a pre-determined sequence. In some embodiments, the first connector sequence comprises at least one nucleotide that is different from a nucleotide of the second connector sequence. In some embodiments, the first connector sequence encodes a same amino acid sequence as the second connector sequence. In some embodiments, the first connector sequence encodes a different amino acid sequence from the second connector sequence.

In another aspect, the present disclosure provides a method for generating a plurality of nucleic acid molecules, each nucleic acid molecule of the plurality encoding a T-cell receptor (TCR) chain or region thereof, the method comprising: contacting a first plurality of nucleic acid molecules and a second plurality of nucleic acid molecules to generate a third plurality of nucleic acid molecules comprising at least two (e.g., at least about 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more) different nucleic acid molecules, wherein each of the at least two different nucleic acid molecules has a different sequence encoding a different TCR chain or region thereof, and wherein the at least two different nucleic acid molecules are generated in a same compartment.

In some embodiments, each nucleic acid molecule of the first plurality of nucleic acid molecules comprises a sequence encoding a CDR3 of the TCR chain. In some embodiments, each nucleic acid molecule of the first plurality of nucleic acid molecules comprises a J region of the TCR chain. In some embodiments, each nucleic acid molecule of the second plurality of nucleic acid molecules comprises a sequence derived from a TCR V gene of the TCR chain. In some embodiments, the TCR V gene is a human TCR V gene. In some embodiments, the TCR V gene is a human TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, or TRAV41. In some embodiments, the TCR V gene is a human TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, or TRBV30. In some embodiments, the sequence derived from the TCR V gene comprises a sequence encoding FR1, CDR1, FR2, CDR2, and FR3. In some embodiments, the sequence derived from the TCR V gene comprises a sequence encoding L-PART1, L-PART2, FR1, CDR1, FR2, CDR2, and FR3. In some embodiments, the TCR chain is a TCR alpha chain, a TCR beta chain, a TCR gamma chain, or a TCR delta chain. In some embodiments, each nucleic acid molecule of the first plurality of nucleic acid molecules further comprises an additional sequence encoding an additional CDR3 of an additional TCR chain. In some embodiments, each nucleic acid molecule of the first plurality of nucleic acid molecules comprises an additional J region of the additional TCR chain. In some embodiments, the TCR chain and the additional TCR chain are a cognate pair of TCR chains. In some embodiments, a nucleic acid molecule of the plurality of nucleic acid molecules encodes a different TCR or portion thereof. In some embodiments, a given nucleic acid molecule of the first plurality of nucleic acid molecules comprises a connector sequence, which connector sequence is usable for linking the given nucleic acid molecule of the first plurality of nucleic acid molecules to a given nucleic acid molecule of the second plurality of nucleic acid molecules. In some embodiments, the given nucleic acid molecule of the first plurality of nucleic acid molecules and the given nucleic acid molecule of the second plurality of nucleic acid molecules encodes a functional TCR chain or portion thereof. In some embodiments, the given nucleic acid molecule of the second plurality of nucleic acid molecules comprises an anti-connector sequence, which anti-connector sequence is complementary to the connector sequence of the given nucleic acid molecule of the first plurality of nucleic acid molecules. In some embodiments, the method further comprises linking the given nucleic acid molecule of the first plurality of nucleic acid molecules and the given nucleic acid molecule of the second plurality of nucleic acid molecules. In some embodiments, linking comprises hybridizing the given nucleic acid molecule of the first plurality of nucleic acid molecules and the given nucleic acid molecule of the second plurality of nucleic acid molecules. In some embodiments, hybridizing comprises hybridizing the connector sequence of the given nucleic acid molecule of the first plurality of nucleic acid molecules with the anti-connector sequence of the given nucleic acid molecule of the second plurality of nucleic acid molecules. In some embodiments, the method further comprises (i) extending a free 3' end of the given nucleic acid molecule of the second plurality of nucleic acid molecules using the given nucleic acid molecule of the first plurality of nucleic acid molecules as a template, and/or (ii) extending a free 3' end of the nucleic acid molecule of the first plurality of nucleic acid molecules using the given nucleic acid molecule of the second plurality of nucleic acid molecules as a template, to generate a nucleic acid molecule of the third plurality of nucleic acid molecules. In some embodiments, the method further comprises ligating the given nucleic acid molecule of the first plurality of nucleic acid molecules and the given nucleic acid molecule of the second plurality of nucleic acid molecules. In some embodiments, the method further comprises contacting the nucleic acid molecule of the third plurality of nucleic acid molecules with a restriction enzyme to generate a sticky end. In some embodiments, the method further comprises contacting the nucleic acid molecule of the third plurality of nucleic acid molecules with an additional nucleic acid molecule. In some embodiments, the additional nucleic acid molecule encodes a constant region or a portion thereof of a TCR chain. In some embodiments, the method further comprises ligating the nucleic acid molecule of the third plurality of nucleic acid molecules and the additional nucleic acid molecule. In some embodiments, at least five (e.g., in some cases, at least about 6, 7, 8, 9, 10, 20, 30, 40, 50, 60, 70, 80, 90, 100, 200, 300, 400, 500, 1,000, 2,000, 3,000, 4,000, 5,000, 10,000, 20,000, 30,000, 40,000, or more) different nucleic acid molecules of the third plurality of nucleic acid molecules are generated in the same compartment. In some embodiments, at least ten different nucleic acid molecules of the third plurality of nucleic acid molecules are generated in the same compartment. In some embodiments, the same compartment is a well, a tube, or a droplet.

In another aspect, the present disclosure provides a method for generating a plurality of nucleic acid molecules, comprising: (a) providing a first plurality of nucleic acid molecules, wherein a nucleic acid molecule of the first plurality of nucleic acid molecules comprises a sequence encoding a first CDR3 of a first T-cell receptor (TCR) chain and a second CDR3 of a second TCR chain, wherein the first CDR3 and the second CDR3 are from a cognate pair of TCR chains; (b) providing a second plurality of nucleic acid molecules, wherein a nucleic acid molecule of the second plurality of nucleic acid molecules comprises a sequence derived from a TCR V gene; and (c) contacting the first plurality of nucleic acid molecules and the second plurality of nucleic acid molecules, wherein the nucleic acid molecule of the first plurality of nucleic acid molecules links with the nucleic acid molecule of the second plurality of nucleic acid molecules to form a linear nucleic acid molecule comprising the sequence encoding the first CDR3 and the second CDR3 and the sequence derived from the TCR V gene, wherein the sequence encoding the first CDR3 and the second CDR3 and the TCR V gene are derived from the cognate pair of TCR chains. In some embodiments, the first plurality of nucleic acid molecules comprises at least about 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences. In some embodiments, the second plurality of nucleic acid molecules comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more different TCR V genes.

In another aspect, the present disclosure provides a method for generating a plurality of nucleic acid molecules, comprising: (a) providing a first plurality of nucleic acid molecules, wherein a nucleic acid molecule of the first plurality of nucleic acid molecules comprises (i) a synthetic sequence encoding a first CDR3 of a first T-cell receptor (TCR) chain and a second CDR3 of a second TCR chain and (ii) a synthetic sequence encoding a third CDR3 of a third T-cell receptor (TCR) chain and a fourth CDR3 of a fourth TCR chain, wherein the first CDR3 and the second CDR3 are from a first cognate pair of TCR chains and wherein the third CDR3 and the fourth CDR3 are from a second cognate pair of TCR chains; (b) providing a second plurality of nucleic acid molecules, wherein a nucleic acid molecule of the second plurality of nucleic acid molecules comprises a sequence derived from a TCR V gene; and (c) contacting the first plurality of nucleic acid molecules and the second plurality of nucleic acid molecules, wherein the nucleic acid molecule of the first plurality of nucleic acid molecules links with the nucleic acid molecule of the second plurality of nucleic acid molecules to form a nucleic acid molecule comprising the sequence encoding the first CDR3 and the second CDR3 and the sequence derived from the TCR V gene, wherein the sequence encoding the first CDR3 and the second CDR3 and the TCR V gene are derived from the cognate pair of TCR chains. In some embodiments, the first plurality of nucleic acid molecules comprises at least about 2, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences. In some embodiments, the second plurality of nucleic acid molecules comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more different TCR V genes.

In another aspect, the present disclosure provides a method of identifying a sequence of a natively paired T-cell receptor (TCR) in a tissue sample from a subject, comprising: (a) identifying one or more paired sequences of one or more natively paired TCRs in a sample containing a plurality of peripheral T cells obtained from the subject, wherein each of the one or more paired sequences comprises a CDR3 sequence; and (b) identifying a tissue CDR3 sequence of a TCR chain of a TCR in the tissue sample for which the other TCR chain to which it is natively paired is unknown, wherein the tissue CDR3 sequence matches a CDR3 sequence of at least one paired sequence of the one or more paired sequences of the one or more natively paired TCRs, thereby identifying the at least one paired sequence as the sequence of the natively paired TCR in the tissue sample. In some embodiments, identifying in (a) comprises sequencing the one or more natively paired TCRs in the sample containing the plurality of peripheral T cells. In some embodiments, the sequencing comprises single cell sequencing. In some embodiments, the single cell sequencing comprises partitioning the plurality of peripheral T cells into a plurality of compartments, each compartment comprising an individual peripheral T cell of the plurality of peripheral T cells. In some embodiments, the tissue sample is not a bodily fluid sample. In some embodiments, the tissue sample is a solid tumor sample. In some embodiments, the tissue sample is a fixed or frozen sample. In some embodiments, the sample containing the plurality of peripheral T cells is a peripheral blood mononuclear cell (PBMC) sample. In some embodiments, the method further comprises, prior to (a), obtaining a blood sample from the subject. In some embodiments, the method further comprises, prior to (a), isolating peripheral blood mononuclear cells from the blood sample. In some embodiments, the tissue sample comprises a tumor-infiltrating T cell.

In another aspect, the present disclosure provides a method of identifying a target-reactive T-cell receptor (TCR), comprising: (a) providing a cell comprising the TCR identified using the methods described herein; and (b) contacting the cell with a target antigen presented by an antigen-presenting cell (APC), wherein the cell binds to the target antigen presented by the APC via the TCR, thereby identifying the TCR as the target-reactive TCR. In some embodiments, the target antigen is a tumor antigen (e.g., tumor-associated antigens or tumor-specific antigens). In some embodiments, the method further comprises delivering a sequence encoding the target-reactive TCR into a host cell. In some embodiments, the method further comprises administering the host cell into the subject. In some embodiments, the host cell is a T cell. In some embodiments, the T cell is an autologous T cell. In some embodiments, the T cell is an allogeneic T cell. In some embodiments, the cell is a reporter cell line, which reporter cell line comprises a reporter gene that is expressed upon the cell binding to the target antigen presented by the APC.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure", "Fig.", and "FIGURE" herein) of which:

FIG. 4A depicts a schematic of germline genomic DNA of a TCR V gene.

FIG. 4B depicts a schematic of rearranged genomic DNA of a TCR V-J gene.

DETAILED DESCRIPTION OF THE INVENTION

Figure 1A:
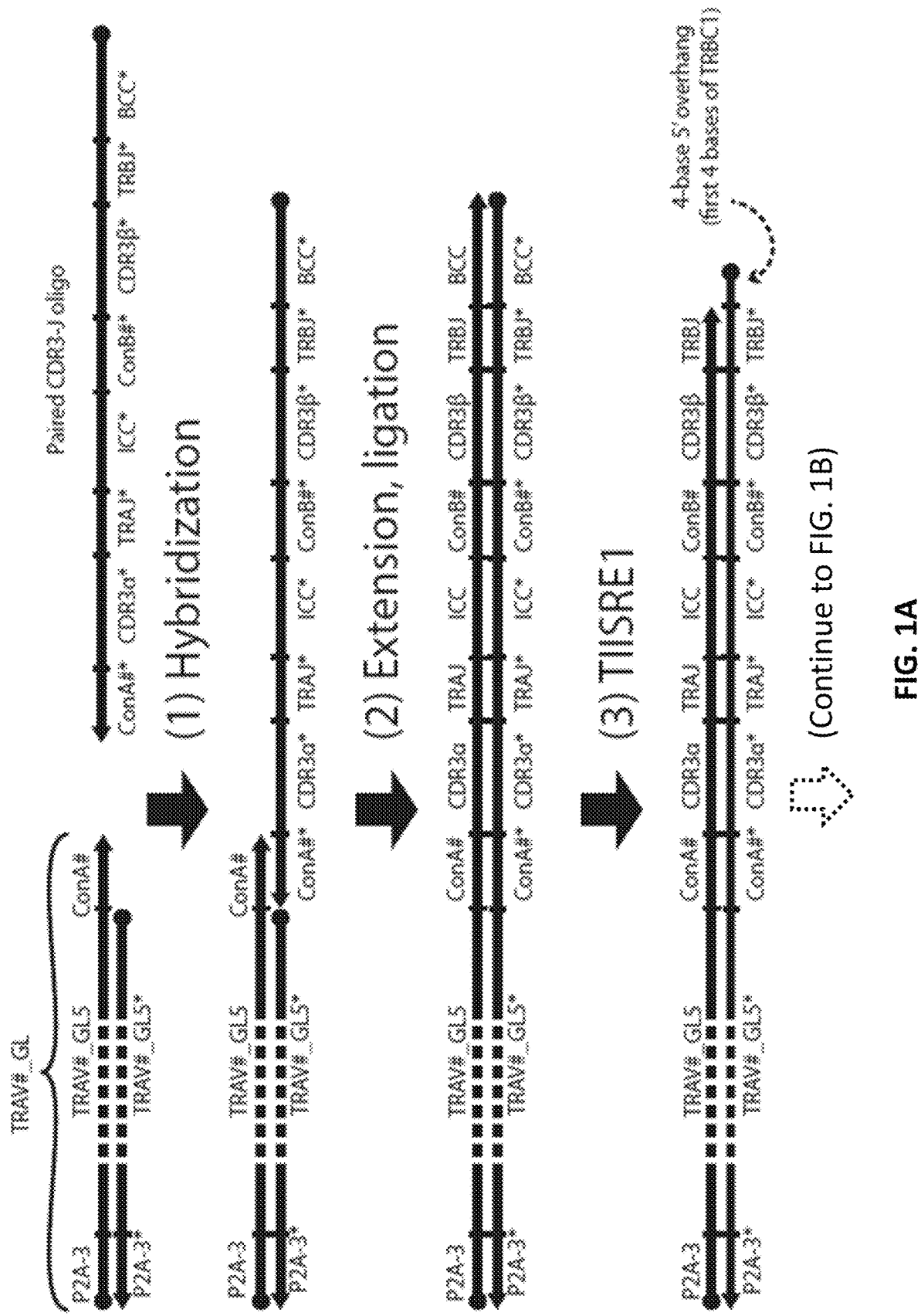
FIGS. 1A-1C depict an example scheme of generating a nucleic acid construct encoding a T-cell receptor.

In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, e.g., within 5-fold, or within 2-fold, of a value. Where particular values are described in the application and claims, unless otherwise stated the term "about" meaning within an acceptable error range for the particular value should be assumed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values.

For example, less than or equal to 3, 2, or 1 is equivalent to less than or equal to 3, less than or equal to 2, or less than or equal to 1.

The terms "polynucleotide", "nucleic acid" and "oligonucleotide" are used interchangeably in the present disclosure. They can refer to a polymeric form of nucleotides of various length. They may comprise deoxyribonucleotides and/or ribonucleotides, or analogs thereof. A polynucleotide may include one or more nucleotides selected from adenosine (A), cytosine (C), guanine (G), thymine (T) and uracil (U), or variants thereof. A nucleotide can include a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. A polynucleotide may have any three-dimensional structure and may perform various functions. A polynucleotide can have various configurations, such as linear, circular, stem-loop, and branched. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), circular RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. Polynucleotides may include one or more nucleotide variants, including nonstandard nucleotide(s), non-natural nucleotide(s), nucleotide analog(s) and/or modified nucleotides.

The term "sequence," as used herein, refers to the order of nucleotides in a nucleic acid molecule, or the order of amino acid residues of a peptide. A nucleic acid sequence can be a deoxyribonucleic acid (DNA) sequence or ribonucleic acid (RNA) sequence; can be linear, circular or branched; and can be either single-stranded or double-stranded. A sequence can be mutated such that it is different from a reference sequence (e.g., wildtype sequence). A sequence can be of any length, for example, between 2 and 1,000,000 or more amino acids or nucleotides in length (or any integer value there between or there above), e.g., between about 100 and about 10,000 nucleotides or between about 200 and about 500 amino acids or nucleotides. In some cases, a given nucleic acid sequence can encompass the sequence information of the given nucleic acid sequence and a reverse complement sequence of the given nucleic acid sequence. In some cases, a DNA sequence can encompass the sequence information of the corresponding RNA sequence that is transcribed from the DNA. The sequence can be alphabetical representation of a polynucleotide or polypeptide molecule. The sequence can be a piece of information that can be used by a computer processor. In some cases, the nucleic acid sequence may be used to refer to the physical nucleic acid molecule itself.

The term "blunt end," as used herein, refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion having at least one nucleotide in length, referred to herein as an "overhang" or "sticky end."

The term "TCR V gene," as used herein, refers to a genomic nucleic acid sequence of a T-cell receptor variable (V) gene, in germline configuration, that comprises the sequence encoding the first part of the leader peptide (e.g., L-PART1 as defined in IMGT), an intron (e.g., V-INTRON as defined in IMGT) and an exon (e.g., V-EXON as defined in IMGT), with a 5'UTR and a 3'UTR (including recombination signal sequence). The recombination signal sequence can comprise a heptamer (e.g., V-HEPTAMER as defined in IMGT) and a nonamer (e.g., V-NONAMER as defined by IMGT), separated by a spacer element (e.g., V-SPACER as defined by IMGT). V-EXON encompasses the sequence encoding the second part of the leader peptide (L-PART2) and V-REGION. Examples of TCR V gene include TCR alpha variable (TRAV) gene, TCR beta variable (TRBV) gene, TCR gamma variable (TRGV) gene, and TCR delta variable (TRDV) gene. A nucleic acid described herein can comprise a sequence derived from the TCR V gene. By "derived from," it means a sequence having a sequence identity of at least about 40%, at least about 50%, at least about 60%, at least about 70%, at least about 80%, at least about 90%, at least about 95%, or 100% with a reference sequence. A sequence derived from a TCR V gene can be a full length sequence of the genomic nucleic acid sequence of a TCR V gene as described above. A sequence derived from a TCR V gene can be a portion of the TCR V gene comprising at least 10, 20, 30, 40, 50, 60, 70, 80, 90, 100, 200, 300, 400, 500, or more nucleotides of the TCR V gene. A sequence derived from a TCR V gene can be a codon-optimized (or codon-diversified) nucleic acid sequence. A codon-optimized sequence of a given nucleic acid sequence refers to a modified nucleic acid sequence whose protein-coding region encodes the same amino acid sequence as the protein-coding region of the given nucleic acid. The modified nucleic acid sequence may have a sequence different from the given nucleic acid sequence or can be derived from the given nucleic acid. Codon optimization may be implemented to remove restriction site, to remove unwanted secondary structure in the polynucleotide sequence, to promote correct linking of a CDR3-J polynucleotide and the designated pre-synthesized portion of a TCR V gene, or for other purposes. Codon optimization or codon diversification can be achieved by altering one or more nucleotides of a given nucleic acid sequence. For example, codon optimization or codon diversification can be achieved by computational methods. Codon optimization and codon diversification may be used interchangeably in the present disclosure.

The term "V-REGION," as used herein, refers to coding region of a TCR V gene (includes 1 or 2 nucleotides before the V-HEPTAMER, if present) in germline genomic DNA or cDNA, or variable (V) region usually trimmed in 3' by the V-(D)-J rearrangement in rearranged genomic DNA or cDNA.

The term "D-REGION," as used herein, refers to coding region of a TCR D gene (includes 1 or 2 nucleotide(s) after the 5' D-HEPTAMER and/or before the 3' D-HEPTAMER, if present) in germline genomic DNA or cDNA, or diversity (D) region usually trimmed in 5' and/or 3' by the D-J or V-D-J rearrangement in partially-rearranged or in rearranged genomic DNA or in cDNA.

The term "J-REGION," as used herein, refers to coding region of a TCR J gene (includes 1 or 2 nucleotide(s) after J-HEPTAMER, if present) in germline genomic DNA or cDNA, or joining (J) region usually trimmed in 5' by the V-(D)-J rearrangement in rearranged genomic DNA or cDNA.

The term "V-J-REGION," as used herein, refers to coding region of a TCR chain that comprises V-REGION and J-REGION, in rearranged genomic DNA or cDNA.

The term "V-D-J-REGION," as used herein, refers to coding region of a TCR chain that comprises V-REGION, D-REGION, and J-REGION, in rearranged genomic DNA or cDNA.

The terms "link" or "connect" are used interchangeably in the present disclosure. They refer to physically linking two or more nucleic acid molecules. The two or more nucleic acid molecules may be linked such that the two or more nucleic acid molecules form a continuous nucleic acid molecule. The two or more nucleic acid molecules can be covalently linked or non-covalently linked. Linking may be accomplished in a variety of manners, including formation of hydrogen bonds, ionic and covalent bonds, or van der Wals forces.

Percent (%) sequence identity with respect to a reference nucleic acid sequence (or peptide sequence) is the percentage of nucleotides (or amino acid residues in case of peptide sequence) in a candidate sequence that are identical with the nucleotides (or amino acid residues) in the reference nucleic acid sequence (or peptide sequence), after aligning the sequences and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software such as BLAST, BLAST-2, CLUSTALW, ALIGN or Megalign (DNASTAR) software. Those skilled in the art can determine appropriate parameters for aligning sequences, including any algorithms needed to achieve maximal alignment over the full length of the sequences being compared.

The term "substantially the same" and its grammatical equivalents as applied to nucleic acid or amino acid sequences mean that a nucleic acid or amino acid sequence comprises a sequence that has at least 90% sequence identity or more, at least 95%, at least 98% or at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)).

Overview

High-throughput, paired sequencing can be used to sequence T-cell receptor (TCR). For example, with the development of single-cell technologies, individual T cells can be partitioned in to insulated compartments where TCR alpha and beta chain mRNAs from the same T cell can be attached to the same, unique barcode. Some of these systems have been made commercially available (e.g., by 10× Genomics). Paired sequence information that records the T-cell receptor alpha variable (TRAV) gene identity, CDR3 alpha sequence, T-cell receptor alpha joining (TRAJ) gene identity, T-cell receptor beta variable (TRBV) gene identity, CDR3 beta sequence, and T-cell receptor beta joining (TRBJ) gene identity can allow reconstruction of the full-length, expressible TCR. However, the technologies to synthesize such TCR sequences in the form of DNA or RNA that can be introduced into cells for functional studies or screenings can be low-throughput. The current disclosure provides multiple methods and compositions that can allow ultrahigh-throughput construction of polynucleotides encoding TCR sequences (e.g., in some cases, paired, full-length, expressible TCR sequences).

T-Cell Receptor (TCR)

The TCR can be used to confer the ability of T cells to recognize antigens associated with various cancers or infectious organisms. The TCR is made up of two chains, e.g., an alpha (α) chain and a beta (β) chain or a gamma (γ) and a delta (δ) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC can be a central event in T-cell activation, which occurs at an immunological synapse at the point of contact between the T cell and the APC.

The TCR may recognize the T cell epitope in the context of an MHC class I molecule. MHC class I proteins can be expressed in all nucleated cells of higher vertebrates. The MHC class I molecule is a heterodimer composed of a 46-kDa heavy chain which is non-covalently associated with the 12-kDa light chain β-2 microglobulin. In humans, there are several MHC alleles, such as, for example, HLA-A2, HLA-A1, HLA-A3, HLA-A24, HLA-A28, HLA-A31, HLA-A33, HLA-A34, HLA-B7, HLA-B45 and HLA-Cw8. In some embodiments, the MHC class I allele is an HLA-A2 allele, which in some populations is expressed by approximately 50% of the population. In some embodiments, the HLA-A2 allele can be an HLA-A*0201, *0202, *0203, *0206, or *0207 gene product. In some cases, there can be differences in the frequency of subtypes between different populations. For example, in some embodiments, more than 95% of the HLA-A2 positive Caucasian population is HLA-A*0201, whereas in the Chinese population the frequency has been reported to be approximately 23% HLA-A*0201, 45% HLA-A*0207, 8% HLA-A*0206 and 23% HLA-A*0203.

In some embodiments, the TCR may recognize the T cell epitope in the context of an MHC class II molecule. MHC class II proteins can be expressed in a subset of APCs. In humans, there are several MHC class II alleles, such as, for example, DR1, DR3, DR4, DR7, DR52, DQ1, DQ2, DQ4, DQ8 and DPI. In some embodiments, the MHC class II allele is an HLA-DRB1*0101, an HLA-DRB*0301, an HLA-DRB*0701, an HLA-DRB*0401 or an HLA-DQB1*0201 gene product.

The TCR chain can comprise a variable domain (or variable region) and a constant domain (or constant region). The variable domain can be a V-DOMAIN as defined by IMGT unique numbering system. The variable domain can correspond to V-J-REGION or V-D-J-REGION of a TCR chain. The constant domain can be C-DOMAIN as defined by IMGT unique numbering system. In some cases, the constant domain can be a portion of the constant region. For example, a full-length constant region can comprise the constant domain (an extracellular region), a connecting region, a transmembrane region, and a cytoplasmic region.

The variable domain of TCRα or TCRδ chain can be encoded by a number of variable (V) and joining (J) gene segments in the germline, while variable domain of TCRβ or TCRγ chain is additionally encoded by diversity (D) gene segments. Each gene segment can be flanked by recombination signal sequences. The recombination signals can comprise a heptamer and a nonamer, separated by a spacer element. The spacer element can be 12 or 23 bp long. During V(D)J recombination, one random allele of each gene segment is recombined with the others to form a functional variable domain. Recombination of the variable domain with a constant (C) gene segment can result in a functional TCR chain transcript. Additionally, random nucleotides may be added and/or deleted at the junction sites between the gene segments. This process can lead to strong combinatorial (depending on which gene regions will recombine) and junctional diversity (depending on which and how many nucleotides will be added/deleted), resulting in a large and highly variable TCR repertoire, which can ensure the identification of a plethora of antigens. Additional diversity can be achieved by the pairing (also referred to as "assembly") of α and β or γ and δ chains to form a functional TCR. By recombination, random insertion, deletion and substitution, the small set of genes that encode the T cell receptor has the potential to create between $10^{15}$ and $10^{20}$ TCR clonotypes. As used herein, a "clonotype" refers to a population of immune cells that carry an identical immunoreceptor. For example, a clonotype refers to a population of T cells that carry an identical TCR, or a population of B-cells that carry an identical BCR (or antibody). "Diversity" in the context of immunoreceptor diversity refers to the number of immunoreceptor (e.g., TCR, BCR and antibody) clonotypes in a population. As used herein, a "cognate pair combination" refers to the native combination of the two chains (e.g., TCRα and TCRβ, or TCRγ and TCRδ) of a TCR from a T cell. The same cognate pair combination of the two chains can result in the same TCR. For example, the T cells having the same clonotype have the same cognate pair combinations of TCRα and TCRβ chains. The higher diversity in clonotype may indicate higher diversity in cognate pair combination.

Each TCR chain can contain three hypervariable loops in its structure, termed complementarity determining regions (CDR1-3). CDR1 and CDR2 can be encoded by V genes and may be required for interaction of the TCR with the MHC complex. CDR3, however, is encoded in part by the (1) junctional region between the V and J genes (in the case of TCRα or TCRγ), or (2) the junctional region between the V and D genes and the junctional region between the D and J genes (in the case of TCRβ or TCRδ), and therefore can be highly variable. CDR3 may be the region of the TCR in direct contact with the peptide antigen. CDR3 can be used as the region of interest to determine T cell clonotypes. The sum of all TCRs by the T cells of one individual is termed the TCR repertoire or TCR profile. The TCR repertoire can change with the onset and progression of diseases. Therefore, determining the immune repertoire status under different disease conditions, such as cancer, autoimmune, inflammatory and infectious diseases may be useful for disease diagnosis and prognosis.

TCR should be understood to encompass full-length TCRs as well as antigen-binding portions or antigen-binding fragments (also called MHC-peptide binding fragments) thereof. In some embodiments, the TCR is an intact or full-length TCR. In some embodiments, the TCR is an antigen-binding portion that is less than a full-length TCR but that binds to a specific antigenic peptide bound to an MHC molecule, e.g., an MHC-peptide complex. In some cases, an antigen-binding portion or fragment of a TCR can contain only a portion of the structural domains of a full-length or intact TCR, but yet is able to bind the epitope (e.g., MHC-peptide complex) to which the full TCR binds. In some cases, an antigen-binding portion or fragment of a TCR contains the variable domains of a TCR, such as variable α chain and variable β chain of a TCR, sufficient to form a binding site for binding to a specific MHC-peptide complex, such as generally where each chain contains three complementarity determining regions. Polypeptides or proteins having a binding domain which is an antigen-binding domain or is homologous to an antigen-binding domain are included.

A TCR molecule can be formed by an alpha chain (a chain or TCRα chain, encoded by TRA gene/sequence) and a beta chain (β chain or TCRβ chain, encoded by TRB gene/sequence), or a gamma chain (γ chain or TCRγ chain, encoded by TRG gene/sequence) and a delta chain (δ chain or TCRδ chain, encoded by TRD gene/sequence). These immunoreceptor chains can have variable domains (e.g., encoded by the rearranged VDJ or VJ regions). Parts of the variable domains can be hypervariable. The hypervariable regions can include complementarity determining regions (CDRs), for example, CDR1, CDR2 and CDR3. In some cases, within one T cell, only one functional α chain sequence and one functional β chain sequence may be expressed. In some cases, within one T cell, only one functional γ chain sequence and one functional δ chain sequence may be expressed.

Chip-Based Oligonucleotide Synthesis: Opportunities and Challenges

Figure 8:
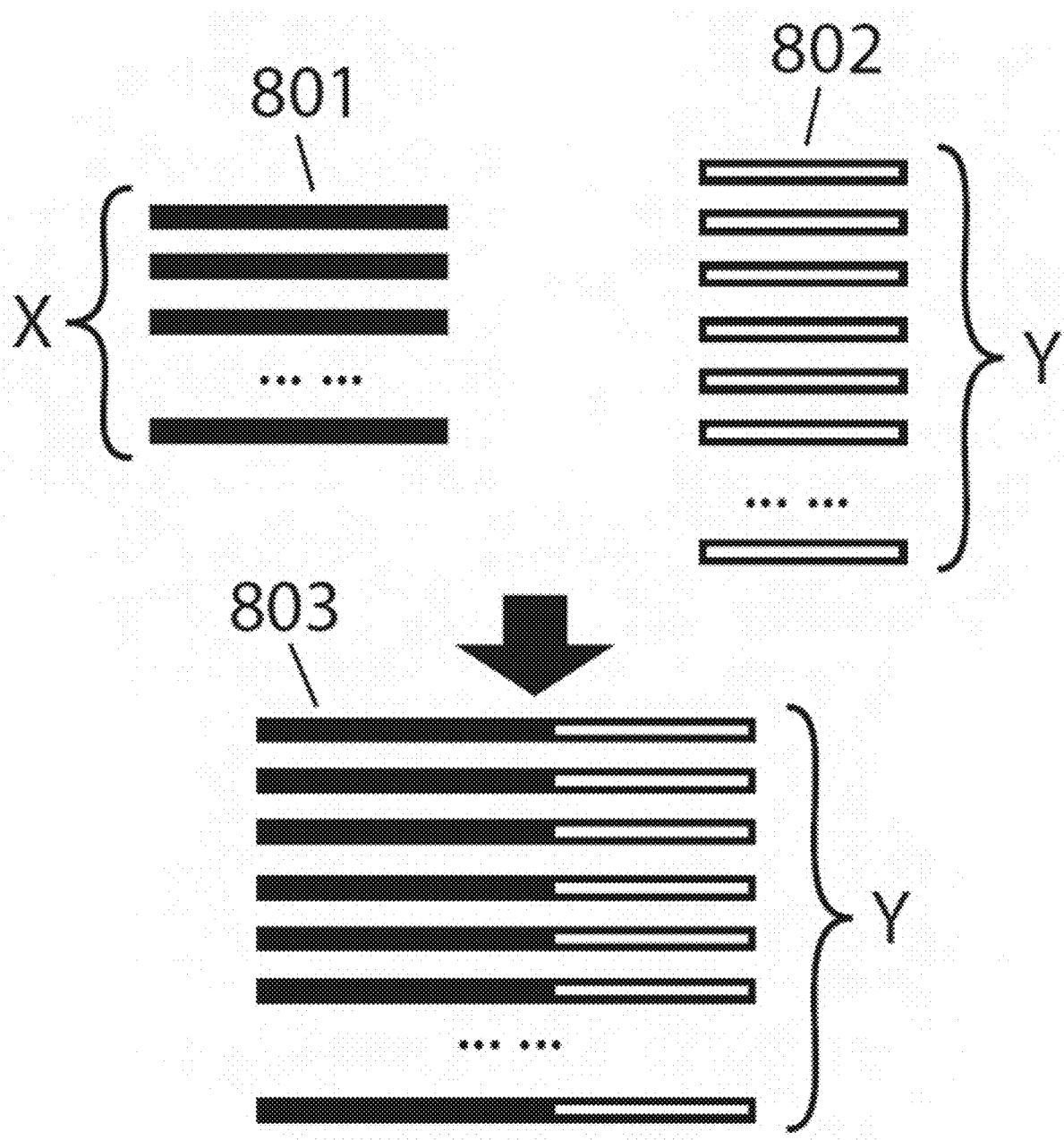
FIG. 8 depicts a general principle of TCR gene self-assembly. 801: a pre-synthesized V gene germline polynucleotide. 802: a polynucleotide comprising a CDR3-J sequence (e.g., a CDR3-J polynucleotide). 803: a nucleic acid sequence comprising a V gene germline polynucleotide sequence and a CDR3-J sequence. X is the number of polynucleotides each being a portion of a different V gene germline polynucleotide. Y is the number of CDR3-J polynucleotides. Y may be much larger than X. The arrow indicates a bulk reaction where each CDR3-J polynucleotide is linked to the designated, pre-synthesized V gene germline polynucleotide.

Although chip-based high-throughput oligonucleotide synthesis technologies may have been progressing, to the point that hundreds of thousands or even millions of oligonucleotides with arbitrary sequences can be synthesized at once, the lengths of the oligonucleotides synthesized in this manner may be limited to about 200 to 300 bases long. In contrast, a full-length TCR construct can be nearly two kilobases long. At first glance, chip-based synthesis may seem insufficient to solve the TCR gene synthesis problem. However, examination of the structure of TCR can reveal opportunities. First, the constant regions of TCR alpha chain and beta chain (e.g., TRAC and TRBC) can be constant. Thus, the polynucleotide sequences encoding constant regions of TCR chains can be appended to the rest of the TCR sequences. Second, unlike BCR/antibody sequences, TCRs may not undergo somatic hypermutation, which means the sequences outside of CDR3 regions can be of germline origin. Therefore, polynucleotides, each comprising a sequence derived from a TCR V gene or a portion thereof can be pre-synthesized. The sequence derived from a TCR V gene can be a portion of the TCR V gene. The sequence derived from a TCR V gene can be a codon-optimized sequence or comprise one or more modified nucleotides. For example, the sequence derived from the TCR V gene comprising coding sequences for L-PART1 (first part of the leader peptide), L-PART2 (second part of the leader peptide), FR1, CDR1, FR2, CDR2 and FR3, referred to as L-V-REGION, can be pre-synthesized. For another example, the sequence derived from the TCR V gene comprising coding sequences for FR1, CDR1, FR2, CDR2 and FR3, referred to as V-REGION, can be pre-synthesized. The nucleic acid sequence segment of L-PART1, L-PART2, FR1, CDR1, FR2, CDR2, or FR3, can be defined according to the IMGT unique numbering system (http://www.imgt.org). In some cases, the sequence derived from the TCR V gene can comprise a sequence starting from the sequence encoding L-PART1 and ending at the codon encoding the second conserved cysteine (e.g., 2nd-CYS, as defined by IMGT, corresponds to codon for the conserved cysteine at position 104 of the V-DOMAIN). Since there are about 80 or more TCR V genes (e.g., TRAV and TRBV genes) in human genome, synthesis of such "V gene germline polynucleotide library" (as shown in FIG. 8, 801 and bracket X) can be feasible. In some cases, a subset of TCR V genes of a species (e.g., a human or a mouse) are synthesized to generate the "V gene germline polynucleotide library." All identified or a subset of TCR V genes may be synthesized. For example, at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more TCR V genes of the species can be synthesized to generate the library. In some cases, all identified TCR V genes of a species are synthesized to generate the library. The TCR V gene can be TRAV, TRBV, TRGV, or TRDV. As described herein, in some cases, a "V gene germline polynucleotide" refers to a portion of the genomic or codon-optimized polynucleotide of a TCR V gene. The sequence derived from the TCR V gene can be the V gene germline polynucleotide. The sequence between FR3 and constant region (e.g., CDR3 plus the remaining of the J region, referred to as "CDR3-J" herein) can be at least about 10, 20, 30, 40, 50, 60, 70, 80, 90 or more nucleotides long, or in some cases, can be up to about 90 nucleotides long. The CDR3-J sequence of the alpha chain and beta chain of a TCR can be at least about 50, 60, 70, 80, 90, 100, 120, 150, 180 or more nucleotides long. The CDR3-J sequence of the alpha chain and beta chain of a TCR (in some cases, in total up to about 180 nucleotides long) can be included into an oligonucleotide (referred to as a "paired CDR3-J oligo", a "paired CDR3-J oligonucleotide" or a "paired CDR3-J polynucleotide", which can be used interchangeably) that can be amenable to chip-based synthesis (as shown in FIG. 8, 802 and bracket Y encompassing 802). In some cases, the paired CDR3-J polynucleotide can comprise a CDR3-J sequence of a TCR gamma chain and a CDR3-J polynucleotide of a TCR delta chain. As used herein, the terms "CDR3-J polynucleotide," "CDR3-J oligonucleotide," and "CDR3-J oligo" (which can be used interchangeably) refer to a polynucleotide sequence comprising one or more CDR3-J sequences. A CDR3-J polynucleotide may be a paired CDR3-J polynucleotide (e.g., comprising CDR3-J sequences from a paired TCR chains). The CDR3-J polynucleotide (e.g., non-paired) may contain only the CDR3-J sequence from one of the paired TCR chains. For example, the CDR3-J polynucleotide may contain only the CDR3-J sequence from a TCR alpha chain, a TCR beta chain, a TCR gamma chain, or a TCR delta chain. The remaining challenge can be to convert such paired CDR3-J oligonucleotide into expressible TCR construct in high throughput (e.g., constructing >1,000 TCRs in one batch). Using the methods described herein, the paired CDR3-J oligonucleotide can be linked to their corresponding V gene germline polynucleotides in a bulk reaction (e.g., FIG. 8, 803). In some cases, the CDR3-J polynucleotide pool (e.g., paired or non-paired) can comprise at least about 2, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences. The V gene germline polynucleotide library can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80 or more TCR V genes. When using the methods described herein, a plurality of at least 2, 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences encoding different natively paired TCRs can be generated. The natively paired TCRs can be generated in bulk in a single compartment.

Figure 4C:
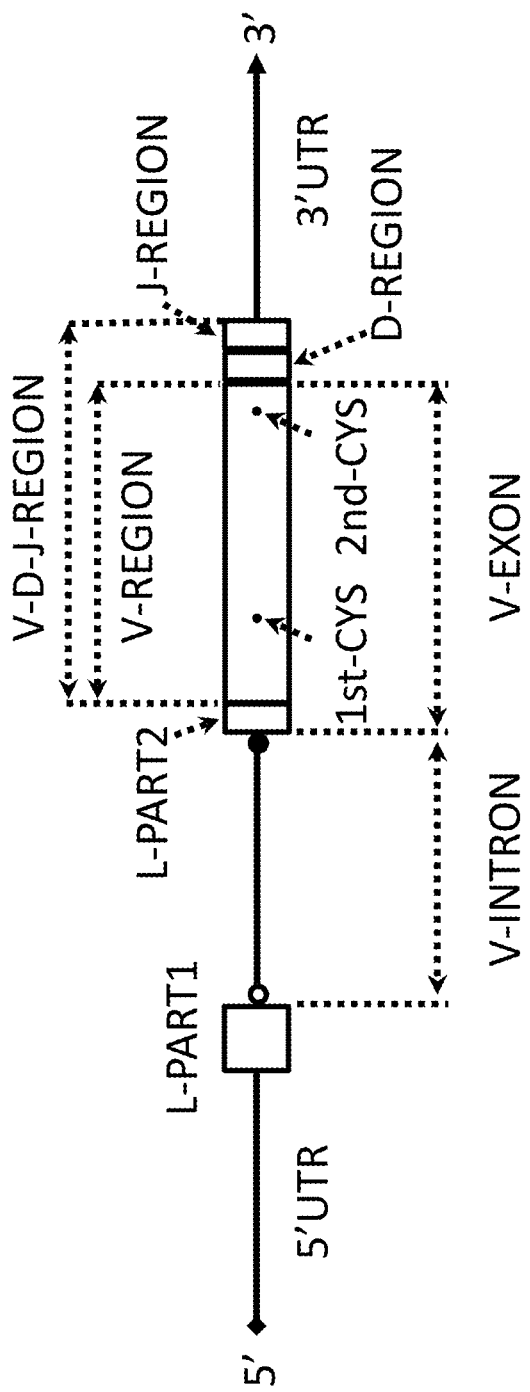
FIG. 4C depicts a schematic of rearranged genomic DNA of a TCR V-D-J gene.

Examples of germline or rearranged gene construct of a nucleic acid molecule comprising a TCR V gene sequence are shown in FIGS. 4A-4C. For example, FIG. 4A shows germline genomic DNA of a TCR V gene, comprising L-PART1, V-INTRON, V-EXON, and recombination signal sequences (V-HEPTAMER, V-SPACER, and V-NONAMER). The two conserved cysteines are also shown in FIG. 4A. After V-(D)-J recombination, an example construct of the rearranged genomic DNA is shown in FIG. 4B or FIG. 4C. The CDR3 can be encoded by (i) the junction (or junctional region) between V-REGION and J-REGION or (ii) the junction between V-REGION and D-REGION and the junction between D-REGION and J-REGION.

The TCR V genes can be very diverse. In human, more than 40 functional V genes for TRA have been identified, including, for example, TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, and TRAV41. Among these V genes, some of them can be classified into a same subgroup and they are indicated by a same subgroup number immediately following "TRAV" but a different number following "-" sign. For example, TRAV1-1 and TRAV1-2 are from a same subgroup. As used herein, a "group" is a set of genes that share the same "gene type" (e.g., V, D, J or C type) and participate potentially in the synthesis of a polypeptide of the same "chain type". By extension, a group includes the related pseudogenes and orphans. A "subgroup" means a set of genes that belong to the same group, in a given species, and that share at least 75% identity at the nucleotide level (in the germline configuration for V, D, and J).

In human, more than 40 functional V genes for TRB have been identified, including, for example, TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, and TRBV30. V genes for other species, e.g., mouse, can be found in IMGT database.

Diversify Connector Sequences

Figure 5:
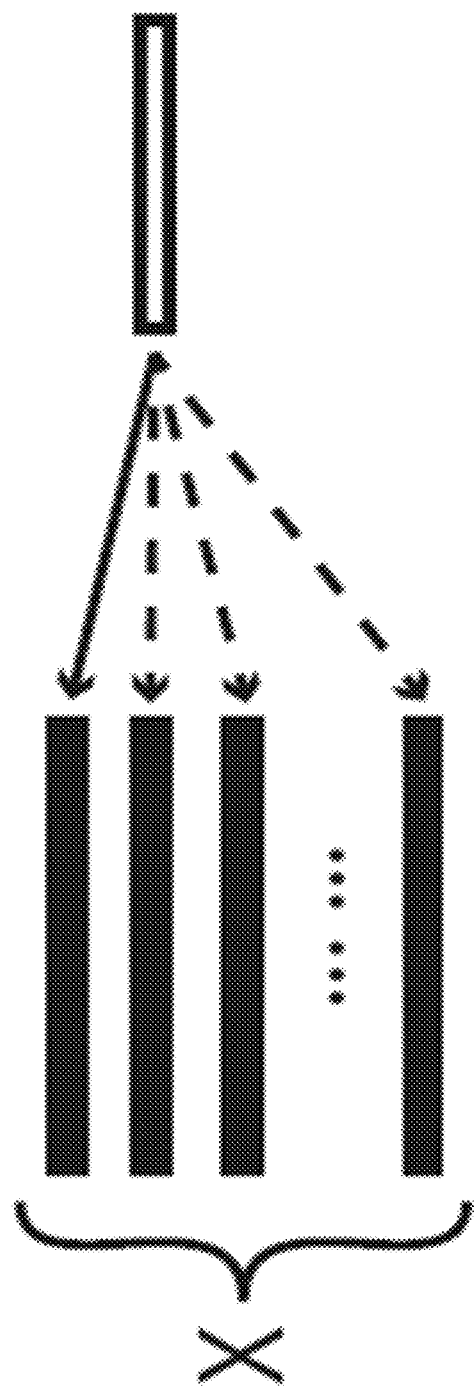
FIG. 5 depicts a scheme of potential challenge associated with linking a CDR3-J polynucleotide to the correct V gene germline polynucleotide. The dashed arrows depict linking can happen between the CDR3-J polynucleotide and the incorrect V gene germline polynucleotide.
Figure 6:
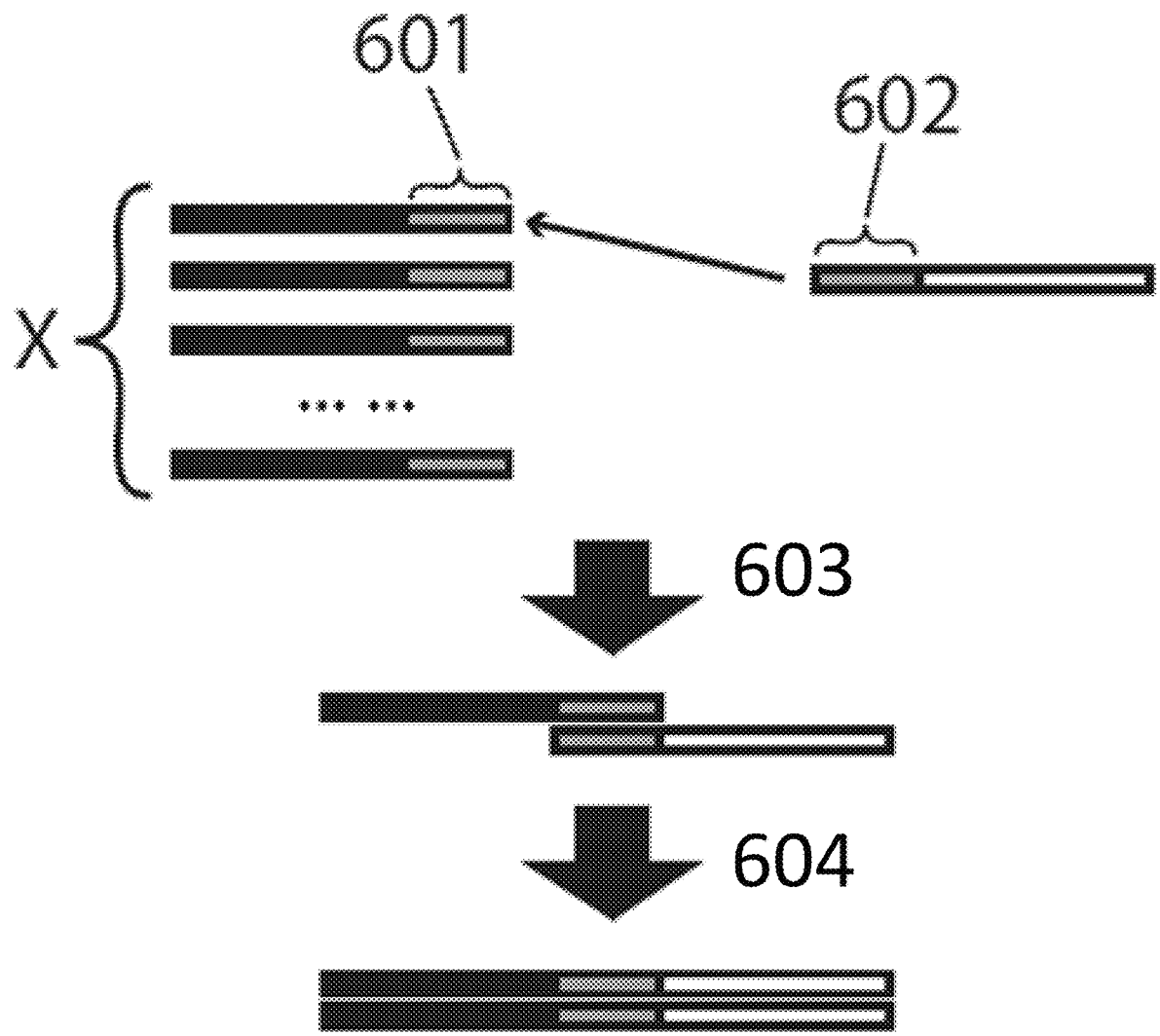
FIG. 6 depicts a scheme of linking a CDR3-J polynucleotide (the gray box connected to the white box) to the designated, pre-synthesized V gene germline polynucleotide (the black box connected to the gray box pointed by the thin arrow), by overlapping primer extension. The top thick arrow (603) depicts hybridization between the connector sequence on the pre-synthesized V gene germline polynucleotide (601) and the connector sequence on the CDR3-J polynucleotide (602). The bottom thick arrow (604) depicts primer extension. 601 may be referred to as a connector sequence and 602 may be referred to as an anti-connector sequence (or vice versa).

Connecting a V gene germline polynucleotide and a CDR3-J polynucleotide can be achieved by molecular biology techniques such as ligation and overlapping primer extension (FIG. 6). However, to fully utilize the power of chip-based oligonucleotide synthesis, one may connect thousands of or more CDR3-J oligonucleotides with their corresponding V gene germline polynucleotides in a bulk reaction (as shown by the arrow of FIG. 8, 803). The major challenge in doing this can be that the connector region between the V gene germline polynucleotide (FIG. 6, 601) and the CDR3-J (FIG. 6, 602) may be the conserved FR3 region. Therefore, in a bulk reaction, it can be difficult to control which V gene germline polynucleotide is connected to which CDR3-J (as depicted in FIG. 5 where the solid arrow depicts linking to the correct V gene germline polynucleotide and the dashed arrows depict linking to the incorrect V gene germline polynucleotide). For example, a TCR sequence may be formed by TRBV4-1 connected to a particular CDR3-J beta sequence. In the bulk reaction, the V gene germline polynucleotides for both TRBV4-1 and TRBV4-2 can be present, and the FR3 regions for these TRBV genes can be highly similar. Therefore, the CDR3-J oligonucleotide for this TCR may be incorrectly connected to the TRBV4-2 germline polynucleotide. To alleviate this problem, codon diversification can be used to create dissimilarities among different FR3 sequences. For example, the connector sequences can be codon-diversified such that they can have different nucleic acid sequences, even though they may encode an identical amino acid sequence. Codon diversification can be achieved by computational methods such as the method shown in Example 2. A plurality of nucleic acid sequences can be generated by assigning a codon to an amino acid randomly or according to an arbitrary rule, where each nucleic acid sequence can encode the same amino acid sequence. Next, the plurality of nucleic acid sequences can be evaluated computationally to assign a score according to an arbitrary rule. The arbitrary rule may consider factors such as restriction site, propensity to hybridize with an unwanted sequence, propensity to hybridize with a given sequence, or unwanted secondary structure in the sequence. Next, based on the score, a nucleic acid sequence can be selected from the plurality of nucleic acid sequences as a codon-diversified connector sequence. The codon-diversified connector sequence can be used to achieve correct linking of a CDR3-J polynucleotide and the designated pre-synthesized portion of a TCR V gene. In a "V gene germline polynucleotide library" comprising some or all the known TCR V genes, for example, each different TCR V gene can have a different connector sequence, which can be used to correctly connect to the corresponding CDR3-J oligonucleotide to form a TCR chain according to a reference sequence. The reference sequence can be generated by sequencing cognate pairs of TCR chains. However, in some cases, it may be unclear to what extent the connector sequences can be diversified and to what extent the connection between the V gene germline polynucleotides and CDR3-J oligonucleotides can be correct in a bulk reaction. As shown in Example 2, it may be possible to diversify the FR3 regions of human TCR V genes so that the 'misconnection probability' for any given CDR3-J sequence is practically undetectable. The algorithm set out in Example 2 can be used to generate 'codon-diversified V gene germline polynucleotides' and their corresponding CDR3-J sequences.

Once a diverse set of connector sequences are found, many methods using molecular biology techniques (e.g., ligation, restriction digestion, circularization) can be used to convert a CDR3-J oligonucleotide pool to a full-length, expressible TCR pool. Example 1 provides an example workflow. The methods provided herein can also be used to generate a pool of individual TCR chains (e.g., not paired chains) in a bulk reaction. For example, to generate a pool of TCR alpha chains, each individual CDR3-J oligonucleotide may comprise CDR3 and J region from TCR alpha chain but may not comprise another CDR3 and J region from a TCR beta chain, and then the CDR3-J oligonucleotide can be used to link with corresponding TRAV gene to form the TCR alpha chain.

Methods for Constructing Nucleic Acid Molecules Encoding TCRs

The nucleic acid molecules encoding TCRs described herein can be constructed from two or more nucleic acid fragments. In some embodiments, the two or more nucleic acid fragments can be referred to as a first nucleic acid molecule, a second nucleic acid molecule, a third nucleic acid molecule, a fourth nucleic acid molecule, etc. When constructing the nucleic acid molecules, standard molecular biology techniques, including but not limited to hybridization, extension, ligation, and enzymatic digestion/cleavage, may be used.

The nucleic acid fragment described herein can encode a TCR chain or portion thereof. For example, the portion of the TCR chain encoded by the nucleic acid fragment can comprise greater than or equal to about 10, 15, 20, 25, 30, 35, 40, 45, 50, 60, 70, 80, 90, 100, 110, 120, 130, 140, 150, 200, 250, or more amino acids. The nucleic acid fragment can comprise a sequence encoding a functional TCR chain. The functional TCR chain may or may not be a full length TCR chain. The functional TCR chain may comprise one or more mutations or modifications. In some cases, a functional TCR chain, when expressed in a host cell, can incorporate into a TCR complex (e.g., a complex having TCRα, TCRβ, CD3γ, CD3δ, CD3ε, and ζ chains). In some cases, a functional TCR can bind to its target ligand. In some cases, a functional TCR, when expressed in a host cell, can incorporate into the cell membrane. In some cases, a functional TCR can be expressed in a host cell.

The nucleic acid fragment used to construct nucleic acid molecule encoding a TCR or portion thereof can comprise a sequence encoding a CDR3.

The nucleic acid fragment used to construct nucleic acid molecule encoding a TCR or portion thereof can comprise a sequence encoding a first CDR3 of a first TCR chain and a second CDR3 of a second TCR chain, wherein the first CDR3 and the second CDR3 are derived from a cognate pair of TCR chains. In some embodiments, the sequence encoding the first CDR3 and the sequence encoding the second CDR3 are separated by at most about 100, 90, 80, 70, 60, 50, 40, 30, 20, 10, or 5 nucleotides.

The nucleic acid fragment used to construct nucleic acid molecule encoding a TCR or portion thereof can comprise a TCR V gene sequence or portion thereof. The nucleic acid fragment used to construct nucleic acid molecule encoding a TCR or portion thereof can comprise a sequence derived from a TCR V gene sequence. The sequence derived from a TCR V gene can comprise a V-REGION nucleic acid sequence. The sequence derived from a TCR V gene can comprise a sequence encoding FR1, CDR1, FR2, CDR2 and/or FR3 nucleic acid sequence. The sequence derived from a TCR V gene can comprise a sequence encoding a leader peptide. The sequence derived from a TCR V gene can comprise a sequence encoding L-PART1, L-PART2, FR1, CDR1, FR2, CDR2 and/or FR3 nucleic acid sequence. The sequence derived from a TCR V gene can comprise or can be a portion of the TCR V gene. The portion of the TCR V gene can be at least 10 nucleotides in length. For example, the portion of the TCR V gene may be greater than or equal to about 10, 20, 30, 50, 60, 70, 80, 90, 100, 200, 300, 400, 500, 600, 700, 800, 900, 1000, or more nucleotides in length. The sequence derived from a TCR V gene may comprise one or more modified nucleotides. The sequence derived from a TCR V gene may be codon-optimized (or codon-diversified)

such that it has a different sequence than the TCR V gene or portion thereof but it can encode a same amino acid sequence. The sequence derived from a TCR V gene may not comprise a sequence encoding a portion of a CDR3. The sequence derived from a TCR V gene may not comprise a sequence of a junctional region of a rearranged gene.

The nucleic acid fragment used to construct nucleic acid molecule encoding a TCR or portion thereof can comprise a sequence encoding a constant domain or portion thereof. The nucleic acid fragment used to construct nucleic acid molecule encoding a TCR or portion thereof can comprise a sequence encoding a constant region or portion thereof. In some cases, the constant domain or constant region is a TCR alpha constant domain or constant region, a TCR beta constant domain or constant region, a TCR gamma constant domain or constant region, or a TCR delta constant domain or constant region. In some cases, the constant region comprises a constant domain. In some cases, the constant region further comprises a transmembrane region, a connecting region, a cytoplasmic region, or a combination thereof.

The nucleic acid fragment used to construct nucleic acid molecule encoding a TCR or a portion thereof can comprise a connector sequence. The connector sequence can be used to link one nucleic acid molecule to another nucleic acid molecule. The connector sequence of one nucleic acid molecule can hybridize (e.g., form base pair or base pairs) with an anti-connector sequence of another nucleic acid molecule. The anti-connector sequence can be complementary (e.g., fully or substantially complementary) with the connector sequence. The anti-connector sequence can be hybridizable with the connector sequence under certain conditions (e.g., temperature, buffer condition, pH, etc.). The anti-connector sequence can be a reverse complement sequence (or complementary sequence) of the connector sequence. When the connector sequence hybridizes with the anti-connector sequence, the base pair(s) formed can be at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 100, or more base pairs. The base pairs formed between the connector sequence and the anti-connector sequence can be contiguous or non-contiguous. For example, in the cases where non-contiguous base pairs are formed, there may be unpaired region or regions separating paired regions. If a first nucleic acid molecule comprises a connector sequence, then a complementary sequence of the connector sequence on a second nucleic acid molecule can be referred to as an anti-connector sequence. The connector sequence (or anti-connector sequence) can be of various lengths. For example, the connector sequence (or anti-connector sequence) can be greater than or equal to about 2, 3, 4, 5, 6, 7, 8, 9, 10, 11, 12, 13, 14, 15, 20, 25, 30, 35, 40, 45, 50, 55, 60, 65, 70, 75, 80, 85, 90, 100, or more nucleotides in length. The connector sequence (or anti-connector sequence) can be less than or equal to about 300, 250, 200, 150, 100, 90, 85, 80, 75, 70, 65, 60, 55, 50, 45, 40, 35, 30, 25, 20, 15, 14, 13, 12, 11, 10, 9, 8, 7, 6, 5, 4, 3 or 2 nucleotides in length. The connector sequence (or anti-connector sequence) can be at 5' end or 3' end of a nucleic acid molecule. The connector sequence (or anti-connector sequence) can also be an internal sequence of a nucleic acid molecule. For example, the connector sequence can be an internal connector sequence and can be exposed at 5' end or 3' end by cutting an internal sequence (e.g., a sequence adjacent to the internal connector sequence) of the nucleic acid molecule. An example of the internal connector sequence is provided in Example 1, the inter-chain connector (ICC). In some cases, a connector sequence and an anti-connector sequence are used to link a nucleic acid molecule encoding a CDR3 or a portion thereof of a TCR chain with another nucleic acid molecule comprising a TCR V gene or a portion thereof. In some cases, a connector sequence and an anti-connector sequence are used to link a nucleic acid molecule comprising a J region of a TCR with another nucleic acid molecule comprising a TCR V gene or a portion thereof. In some cases, a connector sequence and an anti-connector sequence are used to link a nucleic acid molecule comprising a sequence encoding a CDR3 or a portion thereof and a J region of a TCR with another nucleic acid molecule comprising a TCR V gene or a portion. In some cases, a connector sequence and an anti-connector sequence are used to link a nucleic acid molecule comprising a sequence encoding a CDR3 or a portion thereof, a J region, and a TCR V gene or a portion thereof with another nucleic acid molecule encoding a constant domain or a portion thereof of a TCR.

The connector sequence (or the anti-connector sequence) can be a sequence encoding a portion of a TCR V gene (e.g., the portion of the TCR V gene adjacent to the sequence encoding a CDR3 in the rearranged gene). And in such cases, the connector sequence and one or more other connector sequences in a pool of connector sequences may encode a same amino acid sequence (e.g., the conserved portion of the TCR V gene adjacent to the CDR3). When the connector sequence encodes a conserved portion of a TCR V gene, the connector sequence can be codon-diversified such that the connector sequence can be used to link a nucleic acid molecule to another nucleic acid molecule specifically, resulting in a constructed nucleic acid molecule encoding a cognate pair of a TCR. In some embodiments, the connector sequence (or anti-connector sequence) comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 150, 200, or more nucleotides of the TCR V gene adjacent to a sequence encoding a CDR3 in a rearranged gene. Because of the specificity of the connector sequence and the anti-connector sequence, a pool of nucleic acid molecules having different sequences which encode different TCRs can be constructed in a bulk reaction (e.g., in a same compartment). The connector sequence can prescribe which TCR V gene the sequence encoding a CDR3 should be linked to according to a reference sequence (e.g., a native sequence of a TCR chain determined by sequencing). The connector sequence (or the anti-connector sequence) can be an arbitrary (e.g., pre-determined) sequence which may not encode a portion of a TCR V gene. And in such cases, the arbitrary sequence can be removed after linking two nucleic acid fragments together.

Figure 7:
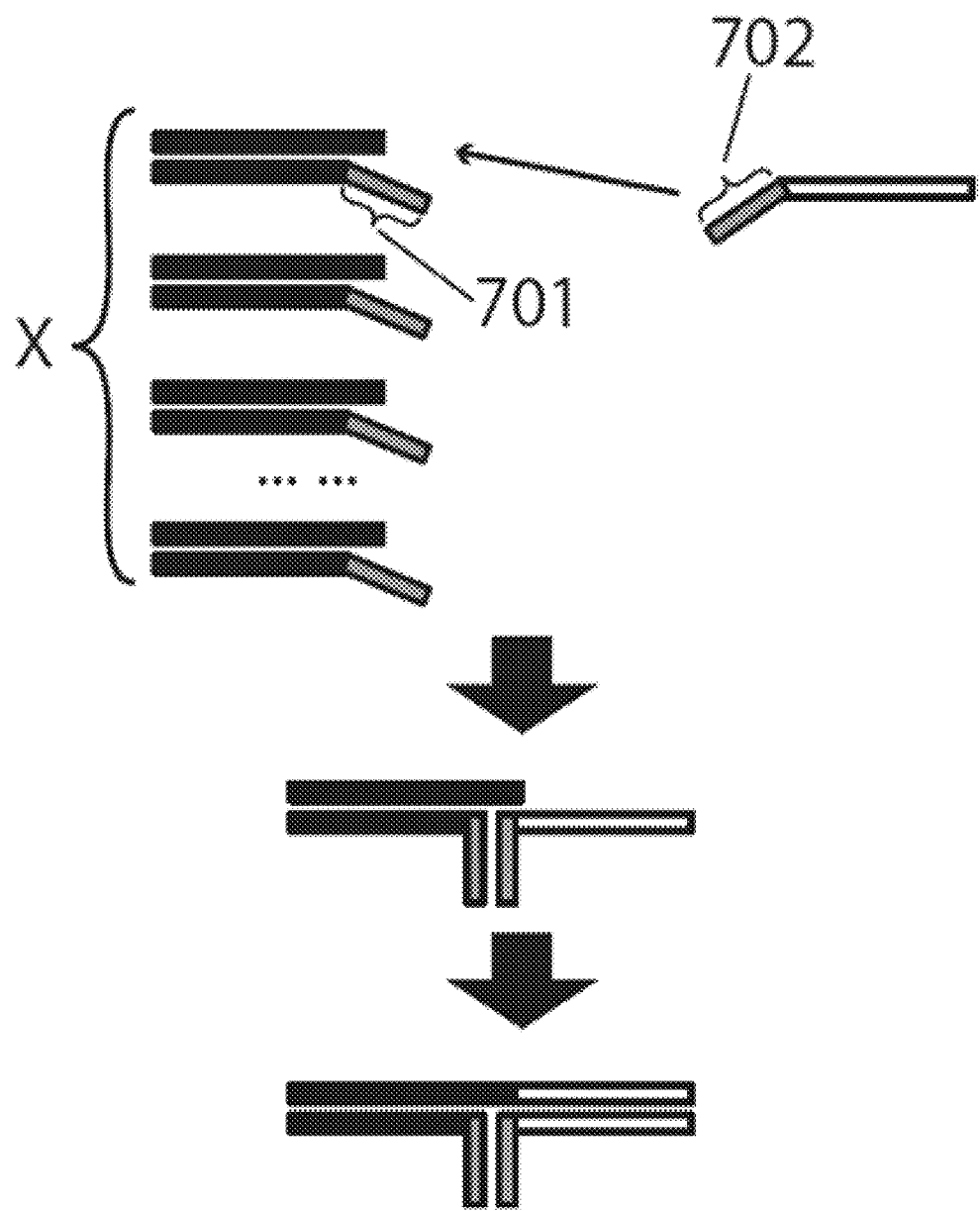
FIG. 7 depicts linking a CDR3-J polynucleotide and the designated V gene germline polynucleotide using arbitrary connector (701) and anti-connector (702) sequences.

FIG. 7 depicts an example to use arbitrary connector (701) and anti-connector (702) sequence to link a CDR3-J polynucleotide to a designated V gene germline polynucleotide (thin arrow). Here each V gene germline polynucleotide has as partially double-stranded structure. The top strand, with its 3' end to its right in this figure, has a single-stranded region at its 3' end. The connector and the anti-connector sequences may be single stranded and may hybridize to each other. The connector and anti-connector sequence only serves the purpose of specific hybridization and may not be related to TCR whatsoever, hence arbitrary. After the hybridization between the connector and the anti-connector, the 3' end of the top strand of the V gene germline polynucleotide may hybridize to the CDR3-J polynucleotide and may be extended by a DNA polymerase. The number of nucleotides on the 3' end of the top strand of the V gene germline polynucleotide that are hybridized to the CDR3-J polynucleotide may be 1, 2, 3, 4, 5, 6, 7, 8, 9, 10, 11, 12, 13, 14, or 15, or up to 20.

The nucleic acid fragment used to construct nucleic acid molecule encoding a TCR or a portion thereof can comprise a self-cleaving peptide. The self-cleaving peptide can be a 2A peptide, an intein peptide, or a hedgehog peptide. Examples of 2A peptide include, but are not limited to, P2A (e.g., sequence: ATNFSLLKQAGDVEENPGP (SEQ ID NO: 284)), E2A (e.g., sequence QCTNYALLKLAGD-VESNPGP (SEQ ID NO: 285)), F2A (e.g., sequence VKQTLNFDLLKLAGDVESNPGP (SEQ ID NO: 286)), and T2A (e.g., sequence EGRGSLLTCGDVEENPGP (SEQ ID NO: 287)) peptide.

The nucleic acid fragment used to construct nucleic acid molecule encoding a TCR or a portion thereof can comprise a restriction enzyme recognition site. For example, the restriction enzyme recognition site can be a recognition site for Type IIS restriction enzyme. Examples of Type-IIS restriction enzymes which can be useful in the present disclosure include, but are not limited to, EarI, MnlI, PleI, AlwI, BbsI, BbvI, BcoDI, BsaI, BseRI, BsmAI, BsmBI, BspMI, Esp3I, HgaI, SapI, SfaNI, BbvI, BsmFI, BsrDI, BtsI, FokI, BseRI, HphI, MlyI and MboII. In some cases, two or more different restriction enzymes can be used during nucleic acid construction process. In some cases, a restriction enzyme that create a 4-bp 5' overhang (for example, BbsI, BbvI, BcoDI, BsaI, BsmBI, FokI, etc.) can be used. In some cases, a restriction enzyme that creates a blunt end or 3' overhang (for example, BseRI, BsrDI, BtsI, MlyI, etc.) can be used.

A nucleic acid fragment used to construct nucleic acid molecule encoding a TCR or a portion thereof can be circularized. For example, the nucleic acid fragment can be circularized by joining two ends of the nucleic acid fragment by ligation. The ligation can be blunt end ligation. The ligation can be performed after creating sticky ends using 5'-to-3' exonuclease (e.g, Gibson Assembly), 3'-to-5' exonuclease (e.g., sequence and ligase independent cloning or SLIC), or USER enzyme mix (e.g., USER friendly DNA recombination or USERec). Additional examples of circularization methods include, but are not limited to, circular polymerase extension cloning (CPEC) and seamless ligation cloning extract (SLiCE) assembly. Alternatively, these two ends can be joined by overlapping PCR. A variety of ligases can be used for ligation, for example, including but not limited to, T4 DNA ligase, T4 RNA ligase, *E. coli* DNA ligase.

The nucleic acid fragment used to construct the nucleic acid molecule encoding a TCR chain or portion thereof can be synthesized chemically. For example, the nucleic acid fragment can be pre-synthesized by chip-based synthesis. In some cases, the nucleic acid fragment synthesized can be equal to or greater than about 10, 20, 30, 40, 50, 60, 70, 80, 90, 100, 150, 200, 250, 300, 350, 400, or more nucleotides in length. In some cases, the nucleic acid fragment synthesized by can be equal to or less than about 500, 450, 400, 350, 300, 250, 200, 150, 100, 90, 80, 70, 60, 50, 40, 30, 20, or 10 nucleotides in length.

The two nucleic acid sequences encoding two peptide chains of a TCR can be constructed in several orientations, for example, head-to-head, head-to-tail, and tail-to-tail. As described herein, "head" refers to "5' end" of a sense nucleic acid strand and "tail" refers to "3' end" of a sense nucleic acid strand. In some cases, the orientation is head-to-tail, the order of the paired nucleic acid sequences encoding a TCR (e.g., TRA followed by TRB, or TRB followed by TRA) can be controlled.

Any nucleic acid molecule described herein can be a double-stranded nucleic acid molecule or single-stranded nucleic acid molecule. In some cases, a nucleic acid molecule may comprise a double-stranded region and a single-stranded region. For example, the nucleic acid molecule having a connector sequence or anti-connector sequence may be a double-stranded nucleic acid molecule having the connector sequence or anti-connector sequence region as a single-stranded region (e.g., an overhang or sticky end). The overhang can be at least 1, 2, 3, 4, 5, 6, 7, 8, 9, 10, or more nucleotides long. The overhang can be at 5' end or 3' end of a nucleic acid molecule.

Any nucleic acid molecule describe herein can comprise one or more modified nucleotides. Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs can be compatible with natural and mutant polymerases for de novo and/or amplification synthesis.

Figure 1B:
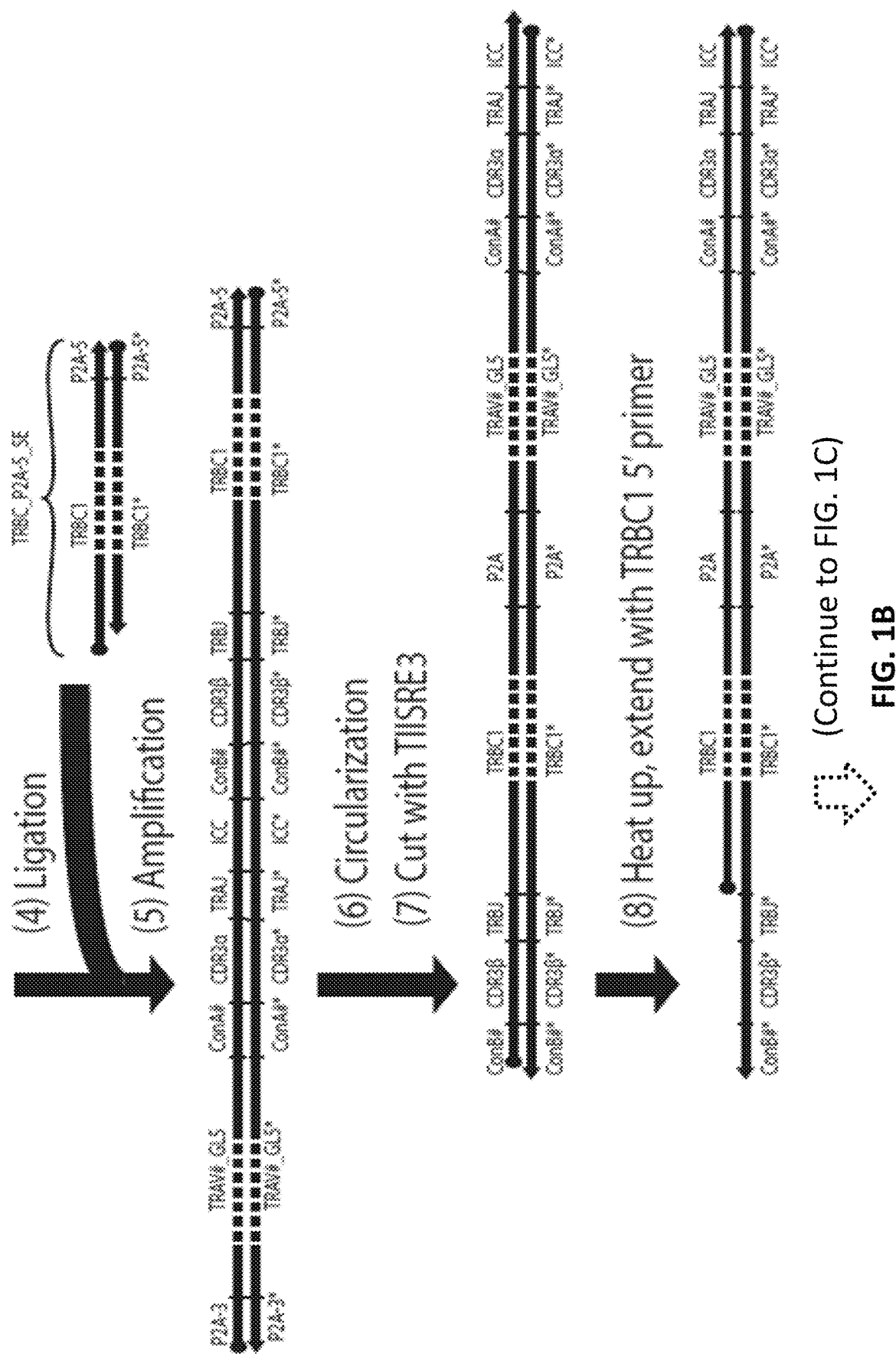
Figure 1C:
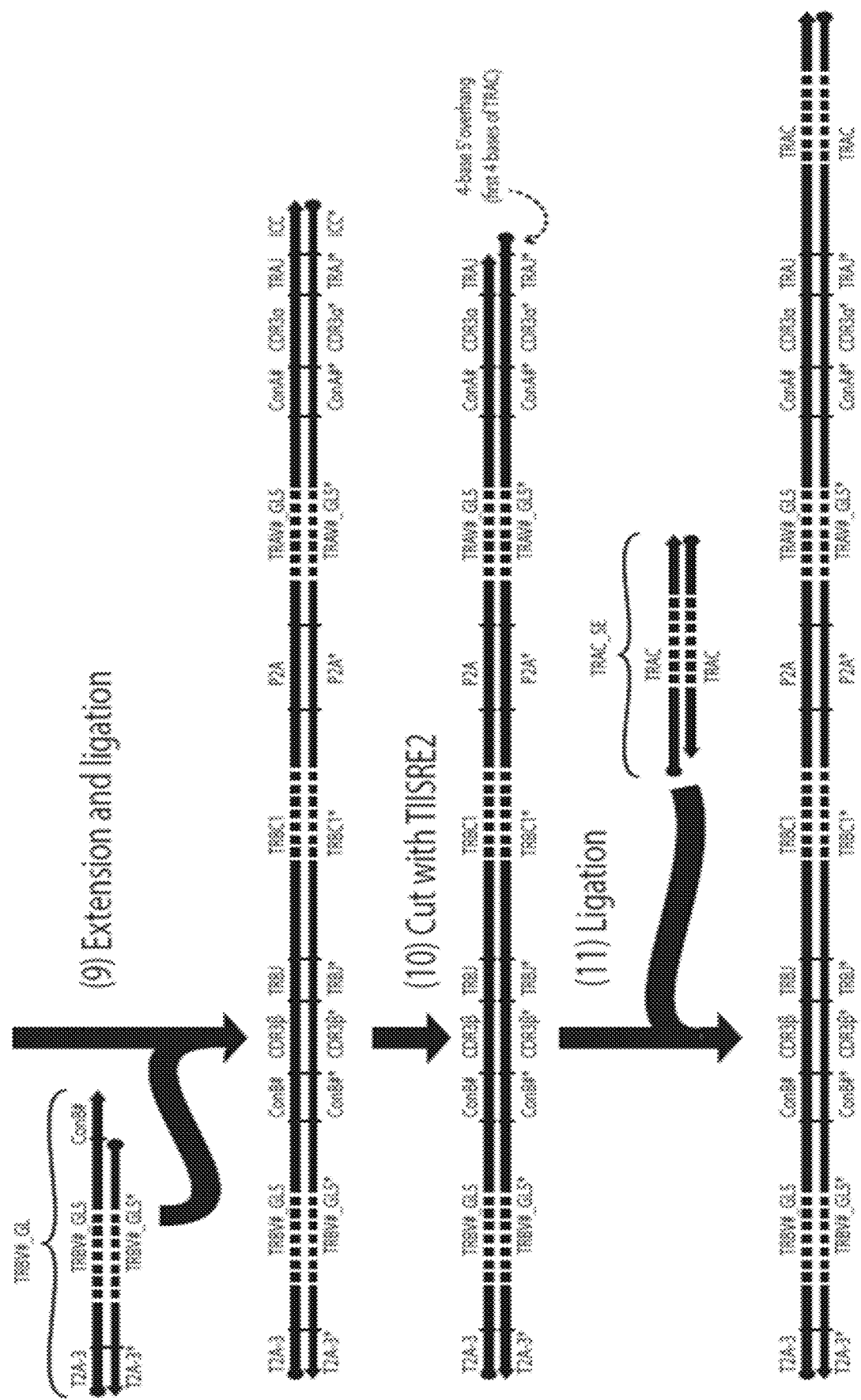

An example workflow of constructing nucleic acid molecules encoding TCRs is shown in FIGS. 1A-1C. A plurality of cognate pairs of TCRs can be pre-determined using various existing methods (e.g., single cell barcoding and sequencing) prior to using the methods described herein to construct the nucleic acid molecules encoding TCRs. Various sequencing methods can be used to determine sequences of paired TCR chains, for example, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing. The paired sequences from the sequencing library can serve as reference sequences for the cognate pairs of TCR chains such that one can know which CDR3 is paired with which V gene through specific interactions between a connector sequence and an anti-connector sequence. A plurality of nucleic acid molecules encoding different TCRs can be constructed in a bulk using the methods described herein, but the construction of one molecule is shown in FIGS. 1A-1C as an example. A first nucleic acid molecule comprising a sequence encoding a first CDR3 (e.g., CDR3α) and a second CDR3 (e.g., CDR3β) can be contacted with a second nucleic acid molecule comprising a sequence derived from a first TCR V gene (e.g., TRAV). The connector sequence (e.g., ConA #*) of the first nucleic acid molecule can hybridize with the anti-connector sequence (ConA #) of the second nucleic acid molecule to link the two nucleic acid molecules. Extension and ligation can be performed to generate a third nucleic acid molecule comprising the sequence derived from the first TCR V gene and the sequence encoding the first CDR3 and the second CDR3. Next, a restriction enzyme (e.g., TIISRE1 of FIG. 1A) can be used to generate an overhang (or sticky end) of the third nucleic acid molecule. Next, the third nucleic acid molecule can be contacted with a fourth nucleic acid molecule comprising a sequence encoding a first constant region or constant domain (e.g., TRBC). The third nucleic acid molecule can then be ligated to the fourth nucleic acid molecule through the overhang to generate a fifth nucleic acid molecule comprising the sequence derived from the first TCR V gene, the sequence encoding the first CDR3 and the second CDR3, and the sequence encoding the first constant region. The fifth nucleic acid molecule can be circularized and cut with a restriction enzyme (e.g., TIISRE3) to expose an internal connector sequence (e.g., ICC). Next, the fifth nucleic acid molecule can be contacted with a sixth nucleic acid molecule comprising a sequence derived from a second TCR V gene (e.g., TRBV). The fifth nucleic acid molecule can be ligated to the sixth nucleic acid molecule through the interaction between a connector sequence and an anti-connector sequence. Next, the sixth nucleic acid molecule can be cut by a restriction enzyme (e.g., TIISRE2) to generate an overhang. Next, the sixth nucleic acid molecule can be contacted with a seventh nucleic acid molecule comprising a sequence encoding a second constant region or constant domain (e.g., TRAC). The sixth nucleic acid molecule and the seventh nucleic acid molecule can be ligated to form an eighth nucleic acid molecule comprising all regions encoding paired TCR chains. The eighth nucleic acid molecule can be further constructed into an expression vector for TCR chain expression in a host cell. It should be understood that the nucleic acid fragment comprising the sequence derived from a TCR V gene may be single-stranded and in such case, the 3' end of the connector sequence of the nucleic acid fragment encoding the CDR3 can be extended upon hybridizing with the anti-connector sequence.

The methods described herein can be used to generate a pool of individual TCR chains, for example, a pool of TCR alpha chains or TCR beta chains.

The methods for generating a plurality of nucleic acid molecules described herein can comprise providing a first plurality of nucleic acid molecules (or nucleic acid fragments). A nucleic acid molecule of the first plurality of nucleic acid molecules can comprise a sequence encoding a first CDR3 of a first T-cell receptor (TCR) chain and a second CDR3 of a second TCR chain. The first CDR3 and the second CDR3 can be from a cognate pair of TCR chains. Next, a second plurality of nucleic acid molecules can be provided. A nucleic acid molecule of the second plurality of nucleic acid molecules can comprise a sequence derived from a TCR V gene. The nucleic acid molecule may not comprise a sequence encoding a constant domain. Next, the first plurality of nucleic acid molecules and the second plurality of nucleic acid molecules can be contacted. The nucleic acid molecule of the first plurality of nucleic acid molecules can link with the nucleic acid molecule of the second plurality of nucleic acid molecules to form a nucleic acid molecule comprising the sequence encoding the first CDR3 and the second CDR3 and the sequence derived from the TCR V gene. The sequence encoding the first CDR3 and the second CDR3 and the TCR V gene can be derived from the cognate pair of TCR chains.

The method for generating a plurality of nucleic acid molecules, each nucleic acid molecule of the plurality encoding a T-cell receptor (TCR) chain or region thereof, can comprise contacting a first plurality of nucleic acid molecules and a second plurality of nucleic acid molecules to generate a third plurality of nucleic acid molecules comprising at least two different nucleic acid molecules. Each of the at least two different nucleic acid molecules can have a different sequence encoding a different TCR chain or region thereof. The at least two different nucleic acid molecules can be generated in a same compartment. In some cases, at least about 5, 10, 20, 50, 100, 200, 300, 400, 500, 1,000, 1,500, 2,000, 2,500, 3,000, 3,500, 4,000, 5,000, 6,000, 7,000, 8,000, 9,000, 10,000, 12,000, 15,000, 20,000, 100,000, 1,000,000, 10,000,000, or more different sequences encoding different TCRs can be generated in the same compartment.

The method for generating a plurality of nucleic acid molecules described herein can comprise providing a first plurality of nucleic acid molecules. A nucleic acid molecule of the first plurality of nucleic acid molecules can comprise a sequence encoding a first CDR3 of a first T-cell receptor (TCR) chain and a second CDR3 of a second TCR chain. The first CDR3 and the second CDR3 can be from a cognate pair of TCR chains. Next, a second plurality of nucleic acid molecules can be provided. A nucleic acid molecule of the second plurality of nucleic acid molecules can comprise a sequence derived from a TCR V gene. Next, the first plurality of nucleic acid molecules and the second plurality of nucleic acid molecules can be contacted. The nucleic acid molecule of the first plurality of nucleic acid molecules can link with the nucleic acid molecule of the second plurality of nucleic acid molecules to form a linear nucleic acid molecule comprising the sequence encoding the first CDR3 and the second CDR3 and the sequence derived from the TCR V gene. The sequence encoding the first CDR3 and the second CDR3 and the TCR V gene can be derived from the cognate pair of TCR chains.

The method for generating a plurality of nucleic acid molecules can comprise providing a first plurality of nucleic acid molecules. A nucleic acid molecule of the first plurality of nucleic acid molecules can comprise (i) a synthetic sequence encoding a first CDR3 of a first T-cell receptor (TCR) chain and a second CDR3 of a second TCR chain and (ii) a synthetic sequence encoding a third CDR3 of a third T-cell receptor (TCR) chain and a fourth CDR3 of a fourth TCR chain. The first CDR3 and the second CDR3 can be from a first cognate pair of TCR chains and the third CDR3 and the fourth CDR3 can be from a second cognate pair of TCR chains. Next, a second plurality of nucleic acid molecules can be provided. A nucleic acid molecule of the second plurality of nucleic acid molecules can comprise a sequence derived from a TCR V gene. Next, the first plurality of nucleic acid molecules and the second plurality of nucleic acid molecules can be contacted. The nucleic acid molecule of the first plurality of nucleic acid molecules can link with the nucleic acid molecule of the second plurality of nucleic acid molecules to form a nucleic acid molecule comprising the sequence encoding the first CDR3 and the second CDR3 and the sequence derived from the TCR V gene. The sequence encoding the first CDR3 and the second CDR3 and the TCR V gene can be derived from the cognate pair of TCR chains.

The method for generating a nucleic acid molecule encoding a T-cell receptor (TCR) chain or portion thereof can comprise providing at least one nucleic acid molecule comprising a sequence encoding a CDR3 of a TCR chain. Next, a plurality of nucleic acid molecules can be provided. Each nucleic acid molecule of the plurality can comprise a sequence derived from a TCR V gene. The plurality of nucleic acid molecules can comprise at least two different sequences derived from at least two different TCR V genes. In some cases, the plurality of nucleic acid molecules can comprise at least 2, 5, 10, 15, 20, 25, 30, 35, 40 or more different sequences derived from at least 2, 5, 10, 15, 20, 25, 30, 35, 40 or more different TCR V genes. Next, the at least one nucleic acid molecule comprising a sequence encoding a CDR3 of a TCR chain can be contacted to the plurality of nucleic acid molecules, each comprising a sequence derived from a TCR V gene, in a same compartment. The at least one nucleic acid molecule comprising a sequence encoding a CDR3 of a TCR chain can be capable of linking to a nucleic acid molecule of the plurality of nucleic acid molecules to generate a third nucleic acid molecule comprising the sequence encoding the CDR3 and a sequence derived from one of the at least two different TCR V genes, thereby generating the nucleic acid molecule encoding the TCR chain or portion thereof.

The composition described herein that can be used for the methods described herein can comprise a first plurality of nucleic acid molecules. Each nucleic acid molecule of the first plurality of nucleic acid molecules can comprise a sequence encoding a first CDR3 of a first T-cell receptor (TCR) chain and a second CDR3 of a second TCR chain. The first CDR3 and the second CDR3 can be from a cognate pair of TCR chains. The composition can further comprise a second plurality of nucleic acid molecules. Each nucleic acid molecule of the second plurality of nucleic acid molecules can comprise a sequence derived from a TCR V gene. Each nucleic acid molecule of the second plurality of nucleic acid molecules may not comprise a sequence encoding the first CDR3 and the second CDR3. In this composition, (i) each nucleic acid molecule of the first plurality of nucleic acid molecules can comprise a sequence encoding a different first CDR3 and/or second CDR3, and/or (ii) each nucleic acid molecule of the second plurality of nucleic acid molecules comprises a sequence derived from a different TCR V gene.

The composition described herein that can be used for the methods described herein can comprise a plurality of nucleic acid molecules. Each nucleic acid molecule of the plurality of nucleic acid molecules can comprise a sequence derived from a T-cell receptor (TCR) V gene. The plurality of nucleic acid molecules can comprise a first nucleic acid molecule having a first connector sequence and a second nucleic acid molecule having a second connector sequence. The first connector sequence can be different from the second connector sequence.

The composition described herein that can be used for the methods described herein can comprise a plurality of nucleic acid molecules. Each nucleic acid molecule of the plurality of nucleic acid molecules can encode a CDR3 of a T-cell receptor (TCR) chain. A first nucleic acid molecule of the plurality can comprise a first connector sequence and a second nucleic acid molecule of the plurality can comprise a second connector sequence. The first connector sequence can be different from the second connector sequence.

The composition described herein that can be used for the methods described herein can comprise a plurality of nucleic acid molecules. Each nucleic acid molecule of the plurality can comprise a sequence encoding at least ten amino acids of a T-cell receptor (TCR) chain. A first nucleic acid molecule of the plurality can comprise a first connector sequence and a second nucleic acid molecule of the plurality can comprise a second connector sequence. The first connector sequence can be different from the second connector sequence. The first connector sequence or the second connector sequence can encode a portion of a TCR chain. The first connector sequence or the second connector sequence can be in frame with the sequence encoding at least ten amino acids of a TCR chain.

The composition described herein that can be used for the methods described herein can comprise a plurality of nucleic acid molecules. Each nucleic acid molecule of the plurality of nucleic acid molecules can comprise a sequence derived from a T-cell receptor (TCR) V gene and may not comprise a CDR3 sequence. A first nucleic acid molecule of the plurality can comprise a first anti-connector sequence and a second nucleic acid molecule of the plurality can comprise a second anti-connector sequence. The first anti-connector sequence can be different from the second anti-connector sequence. The sequence derived from a TCR V gene of the first nucleic acid molecule and the second nucleic acid molecule can be derived from a different TCR V gene. The composition can further comprise at least one nucleic acid molecule comprising a sequence encoding a CDR3 of a TCR chain. The at least one nucleic acid molecule can further comprise a first connector sequence complementary to the first anti-connector sequence.

The present disclosure provides compositions and methods for the assembly or synthesis of a TCR library comprising a plurality of TCRs. In some cases, it may be useful to isolate or purify a particular TCR sequence (e.g., a TCR-of-interest) from the TCR library for further characterization or manipulation. To do this, a barcode can be included in the nucleic acid molecules or fragments used to construct the sequence encoding a TCR or portion thereof. In some cases, a nucleic acid fragment comprising a sequence encoding a CDR3 comprises a barcode. In some cases, a nucleic acid fragment comprising a sequence encoding a first CDR3 of a first TCR chain and a second CDR3 of a second TCR chain comprises a barcode. For example, a CDR3-J oligo or paired CDR3-J oligo can comprise a barcode. The connector sequence (or in some cases, the anti-connector sequence) can comprise a barcode. The interchain connector (or ICC) of the CDR3-J oligo can comprise a barcode. The barcode can be a primer binding site, e.g., a TCR-specific primer-binding site or DOPBS.

For example, each sequence encoding a unique paired CDR3-J in the paired CDR3-J oligo pool (e.g., FIG. 1A) can comprise a unique barcode (or a unique DOPBS). The sequences of the DOPBSes can be arbitrarily designed. The sequences of the DOPBSes can be designed to avoid common pitfalls such as unwanted secondary structures, restriction sites, similarity with other sequences in the TCR genes, or similarities between primer-binding sites. The barcode (or DOPBS) can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides long. The DOPBS can be an additional sequence included in each sequence of the paired CDR3-J pool. The DOPBS can be a sequence already included in each sequence of the paired CDR3-J pool. For example, a connector sequence or portion thereof can be used as a DOPBS. The sequences listed in Table 3 can be used as DOPBSes. The product of Step (9) of FIG. 1C can be used as the template in a dial-out PCR using a forward primer corresponding to T2A-3, and a reverse primer corresponding to the DOPBS associated with the TCR-of-interest. The PCR product can be subject to Steps (10) and (11) of FIG. 1C. The final product can contain primarily the TCR-of-interest.

Expression of TCRs

Using the methods provided herein, a pool of nucleic acid molecules, each encoding a TCR or portion thereof, can be further delivered into a host cell for expression. The constructed nucleic acid molecule can be inserted into vectors in order to be expressed in a host cell. The constructed nucleic acid molecule may be delivered into a recipient cell as a linear or circular nucleic acid strand. In some cases, the constructed nucleic acid or vector comprising the constructed nucleic acid can be delivered into a recipient cell by electroporation. In some cases, the constructed nucleic acid or vector comprising the constructed nucleic acid can be delivered by a carrier such as a cationic polymer.

The vector can be a plasmid, transposon (e.g., Sleeping Beauty, Piggy Bac), adenoviral vector, AAV vector, retroviral vector or lentiviral vector. Non-limiting examples of a vector include a plasmid, shuttle vector, phagemide, cosmid, virion, retroviral vector, adenoviral vector or particle and/or vector commonly used in gene therapy. Non-limiting examples of suitable plasmid vectors include pUC, pBR322, pET, pBluescript, and variants thereof. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A vector may include nucleic acid sequences that permit it to replicate in a host cell, such as an origin of replication. A vector may also include one or more selectable marker genes and other genetic elements. A vector can be an expression vector that includes a constructed nucleic acid sequence encoding a TCR or a portion thereof according to the present disclosure operably linked to sequences allowing for the expression of the TCR. Additional examples of vectors include but are not limited to viral and non-viral vectors, such as retroviral vector (including lentiviral vectors), adenoviral vectors including replication competent, replication deficient and gutless forms thereof, adeno-associated virus (AAV) vectors, simian virus 40 (SV-40) vectors, bovine papilloma vectors, Epstein-Barr vectors, herpes vectors, vaccinia vectors, Moloney murine leukemia vectors, Harvey murine sarcoma virus vectors, murine mammary tumor virus vectors, Rous sarcoma virus vectors and nonviral plasmids. Baculovirus vectors can be suitable for expression in insect cells. The non-viral vector can be formulated into a nanoparticle, a cationic lipid, a cationic polymer, a metallic nanopolymer, a nanorod, a liposome, a micelle, a microbubble, a cell-penetrating peptide, or a liposphere.

In some embodiments, the vector is a self-amplifying RNA replicon, also referred to as self-replicating (m)RNA, self-replication (m)RNA, self-amplifying (m)RNA, or RNA replicon. The self-amplifying RNA replicon is an RNA that can replicate itself. In some embodiments, the self-amplifying RNA replicon can replicate itself inside of a cell. In some embodiments, the self-amplifying RNA replicon encodes an RNA polymerase and a molecule of interest. The RNA polymerase may be a RNA-dependent RNA polymerase (RDRP or RdRp). The self-amplifying RNA replicon may also encode a protease or an RNA capping enzyme. In some embodiments, the self-amplifying RNA replicon vector is of or derived from the Togaviridae family of viruses known as alphaviruses which can include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, Onyong-nyong virus, Ross River virus, Barmah Forest Virus, Getah Virus, Sagiyama virus, Bebaru virus, Mayaro virus, Una virus, Aura virus, Whataroa virus, Babanki virus, Kyzylagach virus, Highlands J Virus, Fort Morgan virus, Ndumu virus, Buggy Creek virus, and any other virus classified by the International Committee on Taxonomy of Viruses (ICTV) as an alphavirus. In some embodiments, the self-amplifying RNA replicon is or contains parts from an attenuated form of the alphavirus, such as the VEE TC-83 vaccine strain. In some embodiments, the self-amplifying RNA replicon vector has been engineered or selected in vitro, in vivo, ex vivo, or in silica for a specific function (e.g., prolonged or increased bipartite immunoreceptor expression) in the host cell, target cell, or organism. For example, a population of host cells harboring different variants of the self-amplifying RNA replicon can be selected based on the expression level of one or more molecules of interested (encoded in the self-amplifying RNA replicon or in the host genome) at different time point. In some embodiments, the selected or engineered self-amplifying RNA replicon has been modified to reduce the type I interferon response, the innate antiviral response, or the adaptive immune response from the host cell or organism which results in the RNA replicon's protein expression persisting longer or expressing at higher levels in the host cell, target cell, or organism. In some embodiments, this optimized self-amplifying RNA replicon sequence is obtained from an individual cell or population of cells with the desired phenotypic trait (e.g., higher or more sustained expression of the molecules of interest, or reduced innate antiviral immune response against the vector compared to the wildtype strains or the vaccine strains). In some embodiments, the cells harboring the desired or selected self-amplifying RNA replicon sequence are obtained from a subject (e.g., a human or an animal) with beneficial response characteristics (e.g., an elite responder or subject in complete remission) after being treated with a therapeutic agent comprising a self-amplifying RNA replicon. In some embodiments, the self-amplifying RNA replicon can contain one or more sub-genomic sequence(s) to produce one or more sub-genomic polynucleotide(s). In some embodiments, the sub-genomic polynucleotides act as functional mRNA molecules for translation by the cellular translation machinery. A sub-genomic polynucleotide can be produced via the function of a defined sequence element (e.g., a sub-genomic promoter or SGP) on the self-amplifying RNA replicon that directs a polymerase to produce the sub-genomic polynucleotide from a sub-genomic sequence. In some embodiments, the SGP is recognized by an RNA-dependent RNA polymerase (RDRP or RdRp). In some embodiments, multiple SGP sequences are present on a single self-amplifying RNA replicon and can be located upstream of sub-genomic sequence encoding for a bipartite immunoreceptor, a constituent of the bipartite immunoreceptor, or an additional agent. In some embodiments, the nucleotide length or composition of the SGP sequence can be modified to alter the expression characteristics of the sub-genomic polynucleotide. In some embodiments, non-identical SGP sequences are located on the self-amplifying RNA replicon such that the ratios of the corresponding sub-genomic polynucleotides are different from instances where the SGP sequences are identical. In some embodiments, non-identical SGP sequences direct the production of a TCR and an additional agent (e.g., a cytokine) such that they are produced at a ratio relative to one another that leads to increased expression of the TCR, increased or faster expansion of the target cell without cytotoxic effects to the target cell or host, or dampens the innate or adaptive immune response against the RNA replicon. In some embodiments, the location of the sub-genomic sequences and SGP sequences relative to one another and the genomic sequence itself can be used to alter the ratio of sub-genomic polynucleotides relative to one another. In some embodiments, the SGP and sub-genomic sequence encoding the TCR can be located downstream of an SGP and sub-genomic region encoding the additional agent such that the expression of the TCR is substantially increased relative to the additional agent. In some embodiments, the RNA replicon or SGP has been selected or engineered to express an optimal amount of the cytokine such that the cytokine promotes the expansion of the T cell or augments the therapeutic effect of the TCR but does not cause severe side effects such as cytokine release syndrome, cytokine storm, or neurological toxicity.

The expression of the two chains can be driven by two promoters or by one promoter. In some cases, two promoters are used. In some cases, the two promoters, along with their respective protein-coding sequences for the two chains, can be arranged in a head-to-head, a head-to-tail, or a tail-to-tail orientation. In some cases, one promoter is used. The two protein-coding sequences can be linked in frame such that one promoter can be used to express both chains. And in such cases, the two protein-coding sequences can be arranged in a head-to-tail orientation and can be connected with ribosome binding site (e.g., internal ribosomal binding site or IRES), protease cleavage site, or self-processing cleavage site (such as a sequence encoding a 2A peptide) to facilitate bicistronic expression. In some cases, the two chains can be linked with peptide linkers so that the two chains can be expressed as a single-chain polypeptide. Each expressed chain may contain the full variable domain sequence including the rearranged V(D)J gene. Each expressed chain may contain the full variable domain sequence including CDR1, CDR2, and CDR3. Each expressed chain may contain the full variable domain sequence including FR1, CDR1, FR2, CDR2, FR3, and CDR3. In some cases, each expressed chain may further contain a constant domain sequence.

To create expression vectors, additional sequences may be added to the constructed nucleic acid molecules. These additional sequences include vector backbone (e.g., elements required for the vector's replication in target cell or in temporary host such as *E. coli*), promoters, IRES, sequence encoding the self-cleaving peptide, terminators, accessory genes (such as payloads), as well as partial sequences of the immunoreceptor polynucleotides (such as part of the sequences encoding the constant domains).

Protease cleavage sites include, but are not limited to, an enterokinase cleavage site: (Asp)4Lys (SEQ ID NO: 288); a factor Xa cleavage site: Ile-Glu-Gly-Arg (SEQ ID NO: 289); a thrombin cleavage site, e.g., Leu-Val-Pro-Arg-Gly-Ser (SEQ ID NO: 290); a renin cleavage site, e.g., His-Pro-Phe-His-Leu-Val-Ile-His (SEQ ID NO: 291); a collagenase cleavage site, e.g., X-Gly-Pro (where X is any amino acid); a trypsin cleavage site, e.g., Arg-Lys; a viral protease cleavage site, such as a viral 2A or 3C protease cleavage site, including, but not limited to, a protease 2A cleavage site from a picornavirus, a Hepatitis A virus 3C cleavage site, human rhinovirus 2A protease cleavage site, a picornavirus 3 protease cleavage site; and a caspase protease cleavage site, e.g., DEVD (SEQ ID NO: 292) recognized and cleaved by activated caspase-3, where cleavage occurs after the second aspartic acid residue. In some embodiments, the present disclosure provides an expression vector comprising a protease cleavage site, wherein the protease cleavage site comprises a cellular protease cleavage site or a viral protease cleavage site. In some embodiments, the first protein cleavage site comprises a site recognized by furin; VP4 of IPNV; tobacco etch virus (TEV) protease; 3C protease of rhinovirus; PC5/6 protease; PACE protease, LPC/PC7 protease; enterokinase; Factor Xa protease; thrombin; genenase I; MMP protease; Nuclear inclusion protein a(N1a) of turnip mosaic potyvirus; NS2BNS3 of Dengue type 4 flaviviruses, NS3 protease of yellow fever virus; ORF V of cauliflower mosaic virus; KEX2 protease; CB2; or 2A. In some embodiments, the protein cleavage site is a viral internally cleavable signal peptide cleavage site. In some embodiments, the viral internally cleavable signal peptide cleavage site comprises a site from influenza C virus, hepatitis C virus, hantavirus, flavivirus, or rubella virus.

A suitable IRES element to include in the vector of the present disclosure can comprise an RNA sequence capable of engaging a eukaryotic ribosome. In some embodiments, an IRES element of the present disclosure is at least about 250 base pairs, at least about 350 base pairs, or at least about 500 base pairs. An IRES element of the present disclosure can be derived from the DNA of an organism including, but not limited to, a virus, a mammal, and a *Drosophila*. In some cases, a viral DNA from which an IRES element is derived includes, but is not limited to, picornavirus complementary DNA (cDNA), encephalomyocarditis virus (EMCV) cDNA and poliovirus cDNA. Examples of mammalian DNA from which an IRES element is derived includes, but is not limited to, DNA encoding immunoglobulin heavy chain binding protein (BiP) and DNA encoding basic fibroblast growth factor (bFGF). An example of *Drosophila* DNA from which an IRES element is derived includes, but is not limited to, an Antennapedia gene from *Drosophila melanogaster*. Addition examples of poliovirus IRES elements include, for instance, poliovirus IRES, encephalomyocarditis virus IRES, or hepatitis A virus IRES. Examples of flaviviral IRES elements include hepatitis C virus IRES, GB virus B IRES, or a pestivirus IRES, including but not limited to bovine viral diarrhea virus IRES or classical swine fever virus IRES.

Examples of self-processing cleavage sites include, but are not limited to, an intein sequence; modified intein; hedgehog sequence; other hog-family sequence; a 2A sequence, e.g., a 2A sequence derived from Foot and Mouth Disease Virus (FMDV); and variations thereof for each.

A vector for recombinant immunoglobulin or other protein expression may include any number of promoters, wherein the promoter is constitutive, regulatable or inducible, cell type specific, tissue-specific, or species specific. Further examples include tetracycline-responsive promoters. The vector can be a replicon adapted to the host cell in which the recombinantly constructed gene is to be expressed, and it can comprise a replicon functional in a bacterial cell as well, for example, Escherichia coli. The promoter can be constitutive or inducible, where induction is associated with the specific cell type or a specific level of maturation, for example. Alternatively, a number of viral promoters can be suitable. Examples of promoters include the β-actin promoter, SV40 early and late promoters, immunoglobulin promoter, human cytomegalovirus promoter, retrovirus promoter, elongation factor 1A (EF-1A) promoter, phosphoglycerate kinase (PGK) promoter, and the Friend spleen focus-forming virus promoter. The promoters may or may not be associated with enhancers, wherein the enhancers may be naturally associated with the particular promoter or associated with a different promoter.

Applications

The compositions and methods described herein can have various applications. An example application can be to re-construct sequences encoding natively paired TCRs from sequencing data, e.g., single cell sequencing data. In some applications, one may want to re-construct sequences encoding natively paired TCRs identified from tumor-infiltrating T cells. In these applications, a fresh tissue sample (e.g., a fresh solid tumor sample) form a subject may be used for single cell sequencing to obtain sequence information of both TCR chains of natively paired TCRs. However, when a tissue sample (e.g., a solid matter sample that is not a bodily fluid sample) containing tumor-infiltrating cells is a frozen sample or a fixed sample (e.g., FFPE sample), it may be challenging to separate cells to obtain single cell suspension. In these cases, a blood sample containing peripheral T cells from the same subject may be used for single cell sequencing to identify sequences of natively paired TCRs. Because the blood sample may contain tumor-infiltrating T cells released from the tissue sample into the blood stream, the sequences obtained from the blood sample may contain the sequences from these tumor-infiltrating T cells. Then, the tissue sample from the same subject can be used for bulk sequencing. Although bulk sequencing of the tissue sample may not provide paired sequences of natively paired TCRs, it can provide CDR3 sequences for individual TCR chains. The CDR3 sequences obtained in the bulk sequencing of the tissue sample (referred to as "tissue CDR3 sequences" herein) can then be used to align with paired sequences obtained in the single cell sequencing of the blood sample. If the CDR3 sequences of the paired sequences match with the tissue CDR3 sequences, the paired sequences can be identified and used for any down-stream applications.

Single cell sequencing refers to obtaining sequence information from individual cells. In single cell sequencing, a population of cells can be made into single cell suspension and compartmentalized into individual partitions. Within each partition, the sequences released from a single cell can be barcoded and later sequenced. Various single cell sequencing methods can be used for TCR reconstruction (see De Simone M, Rossetti G and Pagani M (2018) Single Cell T Cell Receptor Sequencing: Techniques and Future Challenges. Front. Immunol. 9:1638). Bulk sequencing refers to obtaining sequence information from a population of cells. In bulk sequencing, nucleic acid molecules can be isolated from a mixture of cells and subjected to sequencing together.

Figure 9A:
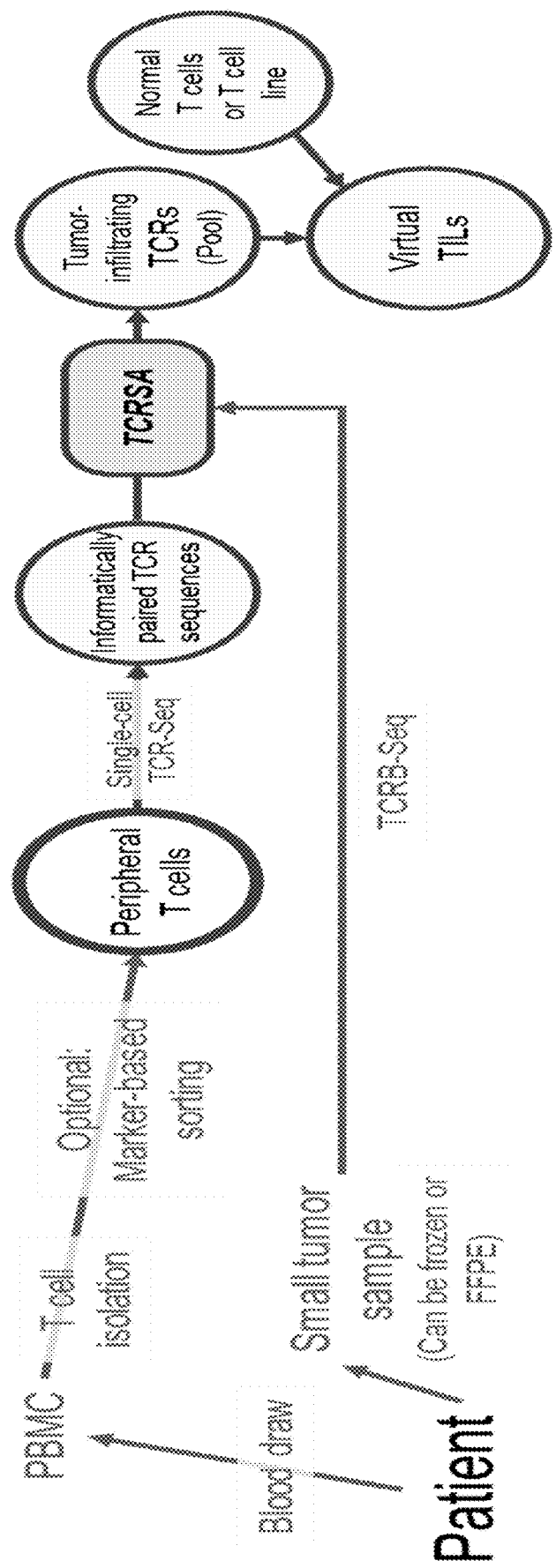
FIG. 9A depicts an example workflow of using blood sample to identify tumor-infiltrating TCRs in the tumor sample.

FIG. 9A shows an example workflow of using blood sample to identify tumor-infiltrating TCRs in the tumor sample. First, a blood sample can be drawn from a patient. Next, a PBMC sample containing peripheral blood mononuclear cells can be isolated from the blood sample. For example, these cells can be extracted from whole blood using ficoll, a hydrophilic polysaccharide that separates layers of blood, and gradient centrifugation. Next, T cell can be isolated from the PBMC sample. T cells can be isolated from PBMCs by lysing the red blood cells and depleting the monocytes, for example, by centrifugation through a PERCOLL™ gradient or by counterflow centrifugal elutriation. Optionally, a subpopulation of T cells may be further enriched by marker-based sorting. The marker can be a cell surface marker. Examples of cell surface markers include, but are not limited to, CD39, CD69, CD103, CD25, PD-1, TIM-3, OX-40, 4-1BB, CD137, CD3, CD28, CD4, CD8, CD45RA, CD45RO, GITR and FoxP3. The marker can be a cytokine. Examples of cytokine markers include, but are not limited to, IFN-γ, TNF-alpha, IL-17A, IL-2, IL-3, IL-4, GM-CSF, IL-10, IL-13, granzyme B and perforin. The T cell or the subpopulation of T cells can then be subjected to single cell sequencing to obtained paired sequences of natively paired TCRs (e.g., informatically paired TCR sequences in FIG. 9A). A tumor sample may also be obtained from the same patient. The tumor sample may be a fixed or frozen sample. For example, the tumor sample may be fixed by a fixing agent such as formaldehyde. The tumor sample may be a formalin-fixed paraffin-embedded (FFPE) tissue sample. Next, the tumor sample can be subjected to bulk sequencing to obtain CDR3 sequences of TCR chains. Next, the CDR3 sequences obtained from the tumor sample can be used to compare with the CDR3 sequences of the paired sequences to identify tumor-infiltrating TCRs. The tumor-infiltrating TCRs can be expressed in normal T cells or cell lines, which are shown as "virtual TILs" in FIG. 9A.

Figure 9B:
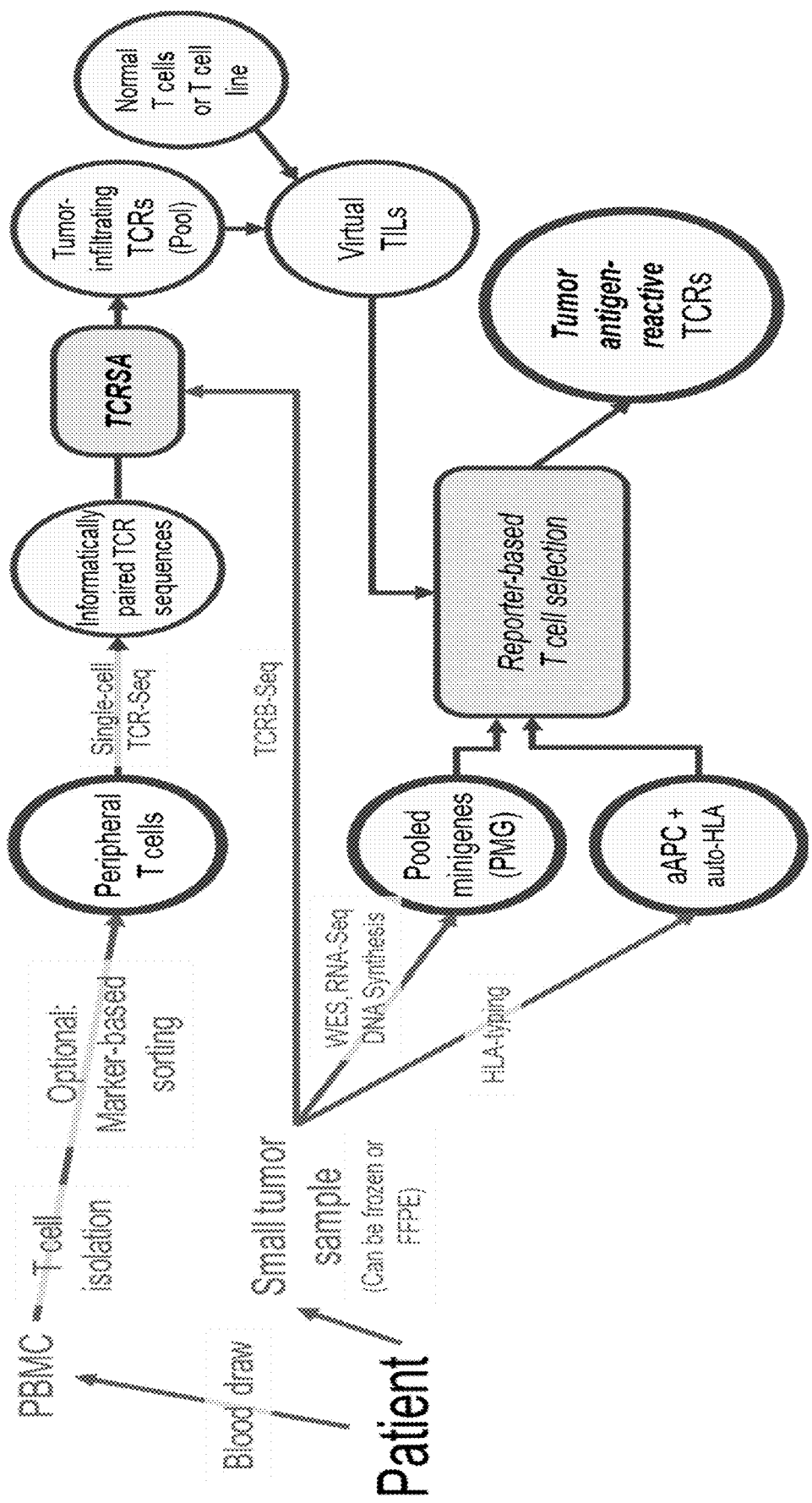
FIG. 9B depicts an example application of TCRs identified using the method shown in FIG. 9A.
Figure 9C:
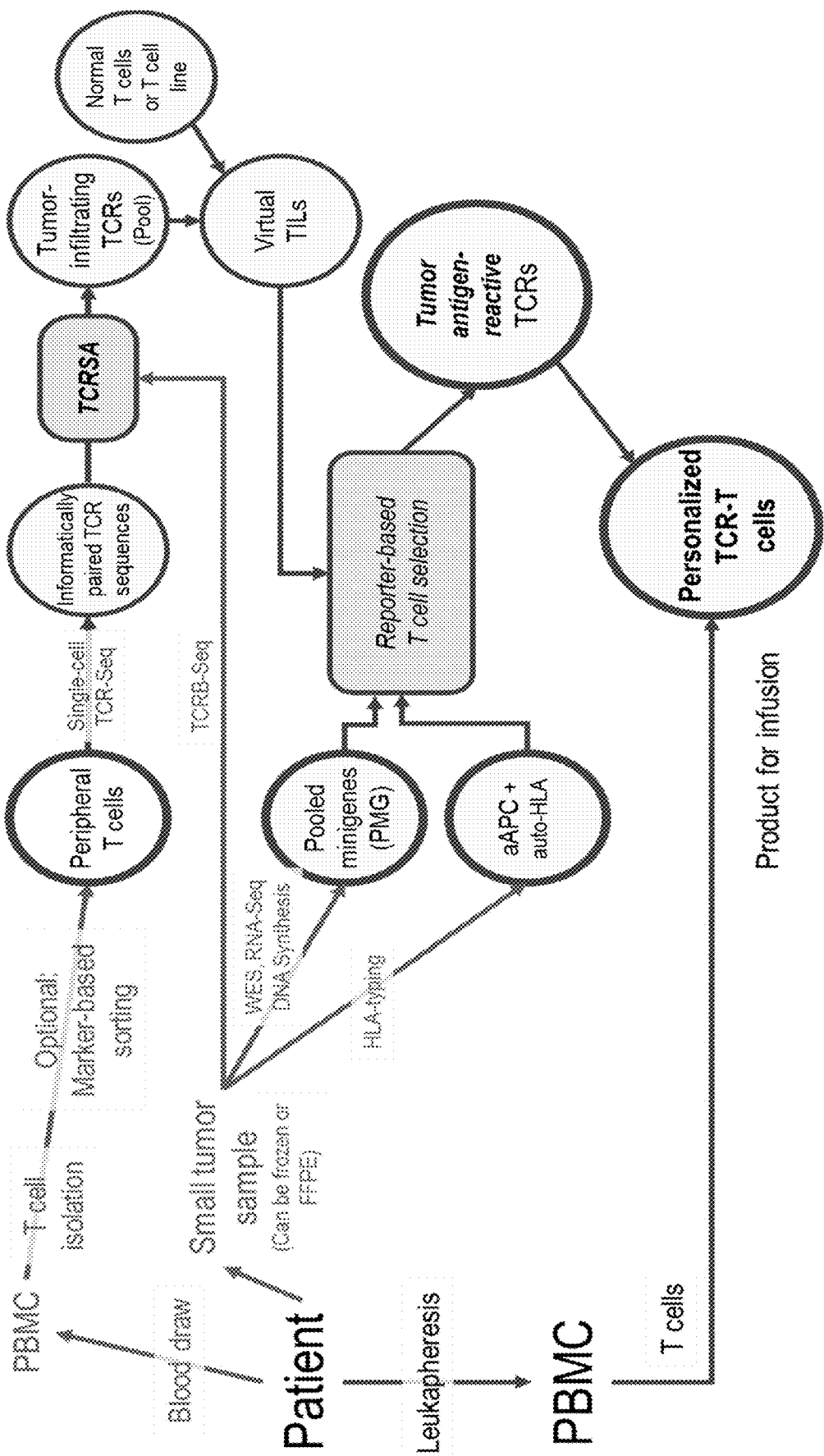
FIG. 9C depicts an example application of TCRs identified using the method shown in FIG. 9A.

FIG. 9B shows an example application of virtual TILs. The virtual TILs can comprise a reporter system, which can be used for reporter-based T cell selection for target-reactive TCRs. For example, the virtual TILs can be a reporter cell comprising a reporter gene, which reporter gene is regulated to send a signal when a TCR of the cell binds to a target antigen. These virtual TILs can be activated by contacting with antigen-loaded antigen-presenting cells (APCs) or artificial APCs. Next, target-reactive T cells can be selected out, for example, by FACS, based on the signal generated by the reporter system or other selection mechanisms (e.g., cell surface marker or cytokine marker). The selection may be based on cell surface marker expression on the virtual TILs after the cells contact MHC-bound antigen. The cell surface marker may be CD25, CD69, CD39, CD103, CD137, as well as other T cell activation markers, or any combination thereof. The selection may be based on calcium influx. The selection may also be based on reporter gene expression. The reporter gene may be a fluorescent protein (such as GFP and mCherry). The reporter gene may be under the control of a transcription factor which is regulated by TCR signaling. Examples of these transcription factors include, but are not limited to, AP-1, NFAT, NF-kappa-B, Runx1, Runx3, etc. The selection may be based on cytokines released from the activated virtual TILs using methods such as ICS and cytokine capture assay. FIG. 9C shows another application of virtual TILs. After identifying target-reactive TCRs, the target-reactive TCRs can be delivered and expressed in host cells such as autologous T cells (the T cells isolated from the same patient where the tissue sample and the blood sample were obtained). The target-reactive TCRs can be delivered and expressed in an allogeneic T cell. The T cells expressing the target-reactive TCRs can then be administered into the same patient to treat diseases such as cancer.

The method of identifying a sequence of a natively paired T-cell receptor (TCR) in a tissue sample (e.g., a solid sample) from a subject can comprise identifying one or more paired sequences of one or more natively paired TCRs in a sample containing a plurality of peripheral T cells obtained from the subject. Each of the one or more paired sequences can comprise a CDR3 sequence. Next, a tissue CDR3 sequence of a TCR chain of a TCR in the tissue sample can be identified, for which the other TCR chain to which it is natively paired may be unknown. The tissue CDR3 sequence can match a CDR3 sequence of at least one paired sequence of the one or more paired sequences of the one or more natively paired TCRs, thereby identifying the at least one paired sequence as the sequence of the natively paired TCR in the tissue sample. Also provided herein is a method of identifying a target-reactive T-cell receptor (TCR). The method can comprise providing a cell comprising the TCR identified using the methods described herein. Next, the cell can be contacted with a target antigen presented by an antigen-presenting cell (APC). The cell can bind to the target antigen presented by the APC via the TCR, thereby identifying the TCR as the target-reactive TCR.

The APC described herein can be professional APC such as dendritic cell, macrophage, or B cell. The APC can be a monocyte or monocyte-derived dendritic cell. An aAPC can express ligands for T cell receptor and costimulatory molecules and can activate and expand T cells for transfer, while improving their potency and function in some cases. An aAPC can be engineered to express any gene for T cell activation. An aAPC can be engineered to express any gene for T cell expansion. An aAPC can be a bead, a cell, a protein, an antibody, a cytokine, or any combination. An aAPC can deliver signals to a cell population that may undergo genomic transplant. For example, an aAPC can deliver a signal 1, signal, 2, signal 3 or any combination. A signal 1 can be an antigen recognition signal. For example, signal 1 can be ligation of a TCR by a peptide-WIC complex or binding of agonistic antibodies directed towards CD3 that can lead to activation of the CD3 signal-transduction complex. Signal 2 can be a co-stimulatory signal. For example, a co-stimulatory signal can be anti-CD28, inducible co-stimulator (ICOS), CD27, and 4-1BB (CD137), which bind to ICOS-L, CD70, and 4-1BBL, respectively. Signal 3 can be a cytokine signal. A cytokine can be any cytokine. A cytokine can be IL-2, IL-7, IL-12, IL-15, IL-21, or any combination thereof.

In some cases, an aAPC may be used to activate and/or expand a cell population. In some cases, an artificial may not induce allospecificity. An aAPC may not express HLA in some cases. An aAPC may be genetically modified to stably express genes that can be used to activation and/or stimulation. In some cases, a K562 cell may be used for activation. A K562 cell may also be used for expansion. A K562 cell can be a human erythroleukemic cell line. A K562 cell may be engineered to express genes of interest. K562 cells may not endogenously express HLA class I, II, or CD1d molecules but may express ICAM-1 (CD54) and LFA-3 (CD58). K562 may be engineered to deliver a signal 1 to T cells. For example, K562 cells may be engineered to express HLA class I. In some cases, K562 cells may be engineered to express additional molecules such as B7, CD80, CD83, CD86, CD32, CD64, 4-1BBL, anti-CD3, anti-CD3 mAb, anti-CD28, anti-CD28mAb, CD1d, anti-CD2, membrane-bound IL-15, membrane-bound IL-17, membrane-bound IL-21, membrane-bound IL-2, truncated CD19, or any combination. In some cases, an engineered K562 cell can expresses a membranous form of anti-CD3 mAb, clone OKT3, in addition to CD80 and CD83. In some cases, an engineered K562 cell can expresses a membranous form of anti-CD3 mAb, clone OKT3, membranous form of anti-CD28 mAb in addition to CD80 and CD83.

Kits

The compositions described herein can be provided in a kit. For example, the kit can comprise a container having a pool of nucleic acid molecules that can be used to construct a plurality of polynucleotide molecules, each polynucleotide encoding a TCR chain or a portion thereof, or a cognate pair of TCR chains. In some cases, each nucleic acid molecule of the pool of nucleic acid molecules encodes a CDR3 of the TCR chain. In some cases, each nucleic acid molecule of the pool of nucleic acid molecules encodes a first CDR3 and a second CDR3 of a cognate pair of TCR chains. In some cases, each nucleic acid molecule of the pool of nucleic acid molecules comprises a sequence derived from a TCR V gene. In some cases, each nucleic acid molecule of the pool of nucleic acid molecules comprises a connector sequence as described herein. The connector sequence may have a different sequence than other connector sequences in the same pool of nucleic acid molecules. The kit can comprise one or more containers, each container containing a pool of nucleic acid molecules. The nucleic acid molecules provided in the kit can be in liquid form or dried form (e.g., lyophilized form).

The kit can further comprise instructional material to direct a user to use the pool of nucleic acid molecules to construct the plurality of polynucleotide molecules encoding TCRs.

The kit can further comprise at least one reagent (e.g., buffer, enzyme, additive, etc.) that can be used in the reaction of constructing nucleic acid molecules.

EXAMPLES

Example 1. Converting a CDR3-J Oligonucleotide Pool to a Full-Length, Expressible TCR Pool This example uses 3 Type IIS Restriction Enzyme to create sticky ends. Such enzymes are commercially available. In this example, two enzymes that create a 4-bp 5' overhang (for example, BbsI, BbvI, BcoDI, BsaI, BsmBI, FokI, etc.) and one restriction enzyme that creates a blunt end or 3' overhang (for example, BseRI, BsrDI, BtsI, MlyI, etc.) are used. The optimal enzyme set to use can depend on practical factors (e.g., local availability, cutting efficiency, star activity) and can be easily chosen experimentally. Here, the first two restriction enzymes are called TIISRE1, TIISRE2, and the last restriction enzyme is called TIISRE3.

In this example, the paired CDR3-J oligonucleotides are synthesized in 'head-to-tail' orientation with respect to the coding sequence of the alpha and beta CDR3-J. In other words, the alpha CDR-3J and beta CDR-3J are synthesized in the same 5' to 3' direction. The resultant full-length, expressible TCR polynucleotide is also in head-to-tail orientation. The paired CDR3-J oligonucleotides can be synthesized in other orientations, for example, head-to-head and tail-to-tail. Methods described herein can be combined with methods described in U.S. Provisional Patent Applications No. 62/718,227, 62/725,842, 62/732,898, 62/818,355 and 62/823,831, each of which is entirely incorporated herein by reference, to design paired CDR-3J oligonucleotides and obtain full-length, expressible TCR polynucleotides in other orientations.

As shown in FIGS. 1A-1C, the paired CDR3-J oligo contains the reverse-complement sequence of TRBJ, CDR3beta, TRAJ, and CDR3alpha, in the 5' to 3' order, with other intervening domains to be described below. Throughout this document, the symbol '*' denotes complementarity. For example, if P refers a polynucleotide sequence, the P* refers to the reverse complement of P. Also, when appropriate, the letter X is used to refer to A or B. For example, TRXV may be used to refer to TRAV and TRBV collectively. For clarity, in this example and in FIGS. 1A-1C, TRAJ domain and TRBJ domain refer to the polynucleotide sequences encoding parts of TRAJ region and TRBJ region, respectively, that are not included in the CDR3.

BCC stands for "beta constant connector", whose function is to connect with TRBC sequence. ConB # is the connector for a specific TRBV sequence, with the symbol # denoting a numerical ID of a TRBV gene. Similarly, ConA # is the connector for a specific TRAV sequence. ICC stands for "inter-chain connector", which will be used for connecting TRBV for to ConB #, as well as connecting TRAC to TRAJ.

ConB # and ConA # domains can be codon-diversified (see Example 2) so that ConX # for different TRBV genes are sufficiently different at nucleotide level that ConX # and ConX #* can hybridize with highly yield only when the numerical IDs for ConX # and ConX #* are the same.

A library of 48 partially double-stranded TRAV #_GL polynucleotides (one for each TRAV gene in IMGT that are annotated as functional) can be prepared using conventional methods. All TRAV #_GL polynucleotides can be mixed to create the TRAV #_GL pool. GL stands for germline. The top strand of each TRAV # GL polynucleotide contains (1) a P2A-3 domain, which encodes the 3' portion of the self-cleaving P2A peptide, (2) a TRAV #_GL5 domain, which encodes the 5' portion of the germline sequence of TRAV #, including L, FR1, CDR1, FR2, CDR2, and the portion of FR3 upstream of ConA #, in this order, and (3) ConA # which encodes the final stretch of FR3 and is codon-diversified. The bottom strand of each TRAV #_GL polynucleotide contains TRAV #_GL5* and P2A-3*. Thus, the TRAV #_GL polynucleotide has a 3' overhang with the sequence ConA #. A library and a pool of 48 TRBV #_GL polynucleotides can be similarly prepared. The P2A-3 domain in TRAV #_GL can be replaced by T2A-3 in TRBV #_GL. T2A is another self-cleaving peptide.

A pool of 1,000 to 500,000 paired CDR3-J oligonucleotides can be prepared by chip-based synthesis.

In Step (1), the TRAV #_GL pool can be mixed with the paired CDR3-J pool at a temperature that allows specific hybridization between ConA # and ConA #*. Then, in Step (2), a DNA polymerase can be used to extend the top strand of TRAV #_GL, and a ligase can be used to ligate the paired CDR3-J oligo and the bottom strand of TRAV #_GL.

BCC contains the recognition site of TIISRE1. In Step (3), TIISRE1 can be used to cleave at BCC, leaving a 4-base 5' overhang at the bottom strand. In this example, the 4 bases are the antisense of the first 4 bases of TRBC1. In Step (4), this cleavage product can be ligated to a pre-prepared TRBC_P2A-5_SE which contains the full TRBC1 sequence and a P2A-5 domain, and has a 4-based 5' overhang at the beginning of the TRBC1 sequence. The P2A-5 domain is the 5' end portion of the P2A coding sequence. SE stands for sticky end. This ligation production can be PCR-amplified in Step (5).

In Step (6), this amplification product can be circularized by ligation between P2A-5 and P2A-3 using method described in U.S. Provisional Patent Applications No. 62/718,227, 62/725,842, 62/732,898, 62/818,355 and 62/823,831. After ligation, P2A-5 and P2A-3 forms P2A. In this example, the ICC contains the recognition site of TIISRE3, which, in Step (7) can be used to cleave immediately 3' of ConB #* on the bottom strand. The cutting site on the top strand is less important. In Step (8), this cleavage product can be heated up to separate the top and bottom strands. A primer containing the first ~20 bases of TRBC1 can be used to extend on the bottom strand, leaving a single-stranded region at the 3' end of the bottom strand. At the tip of the 3' end of this strand is the ConB #* domain. In Step (9), the TRBV #_GL pool can be added so ConB # on the top strand of TRBV #_GL can hybridize with the corresponding ConB #*. DNA polymerase and ligase can be added to convert the hybridization product to fully double-stranded DNA.

The remnant of ICC also contains the recognition site of TIISRE2, which in Step (10) can be used to cleave ICC, leaving a 4-base 5' overhang which is the antisense sequence of the first 4 bases of TRAC. In Step (11) a pre-prepared TRAC_SE can be ligated to the 5' overhang, forming complete TRAC sequence, similar to Step (4) described above.

The final product can be ligated into a lentiviral backbone or proper 'homology sequence' used for CRISPR/TALEN/ZFN-based knock-in.

Example 2. Testing Codon Diversification using Human TRAV and TRBV Sequences

Figure 2A:
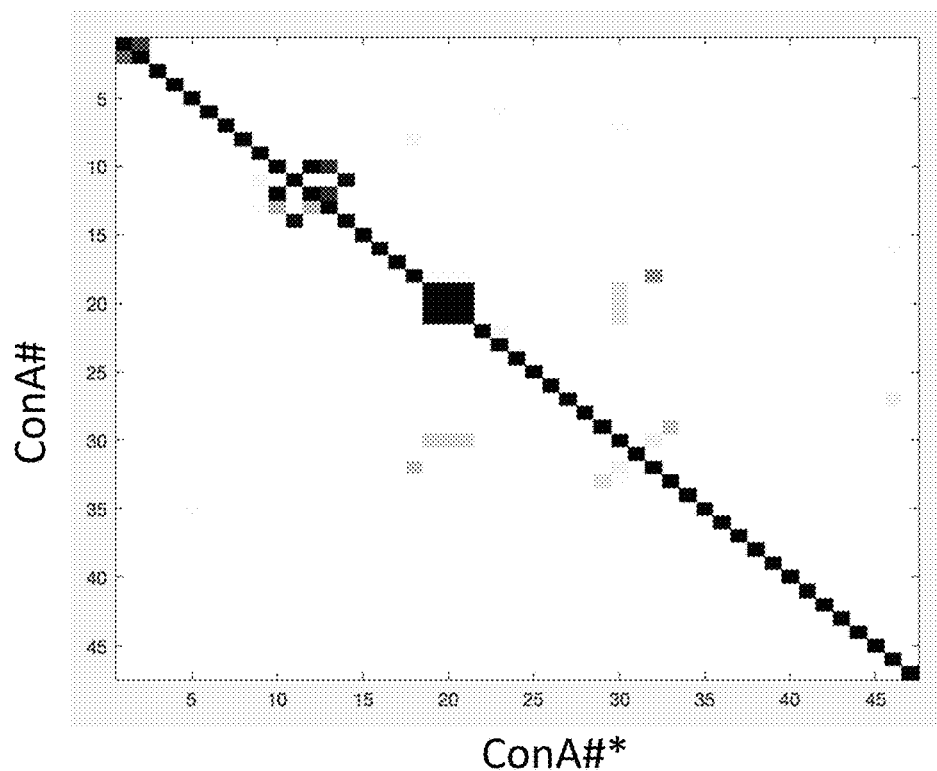
FIG. 2A depicts an example simulation result using the methods described herein.
Figure 2B:
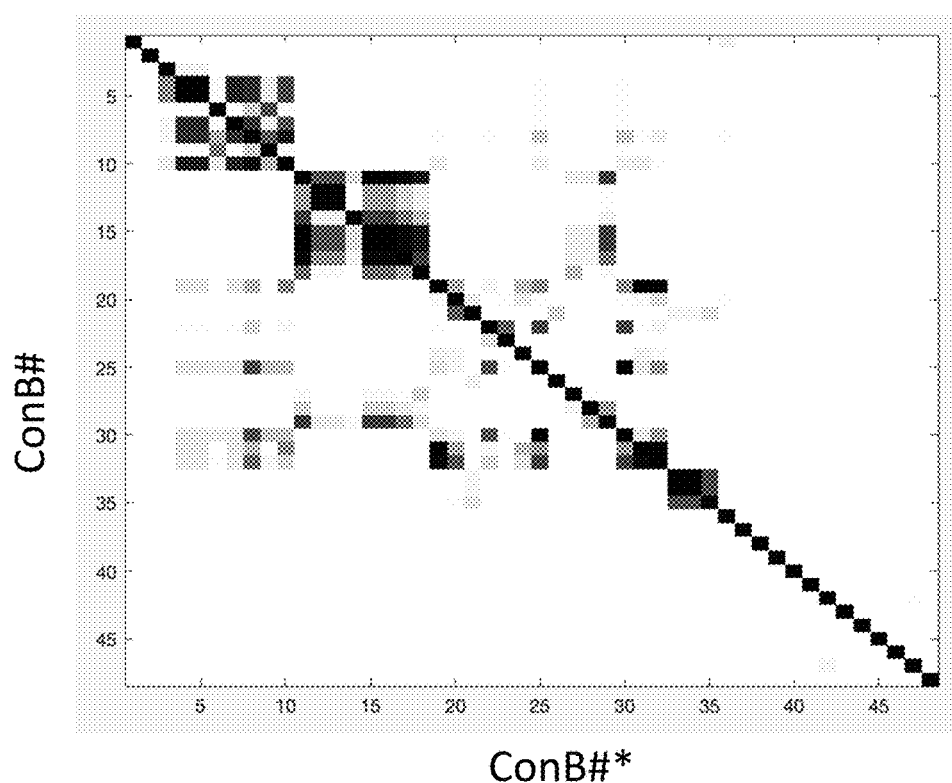
FIG. 2B depicts an example simulation result using the methods described herein.
Figure 3A:
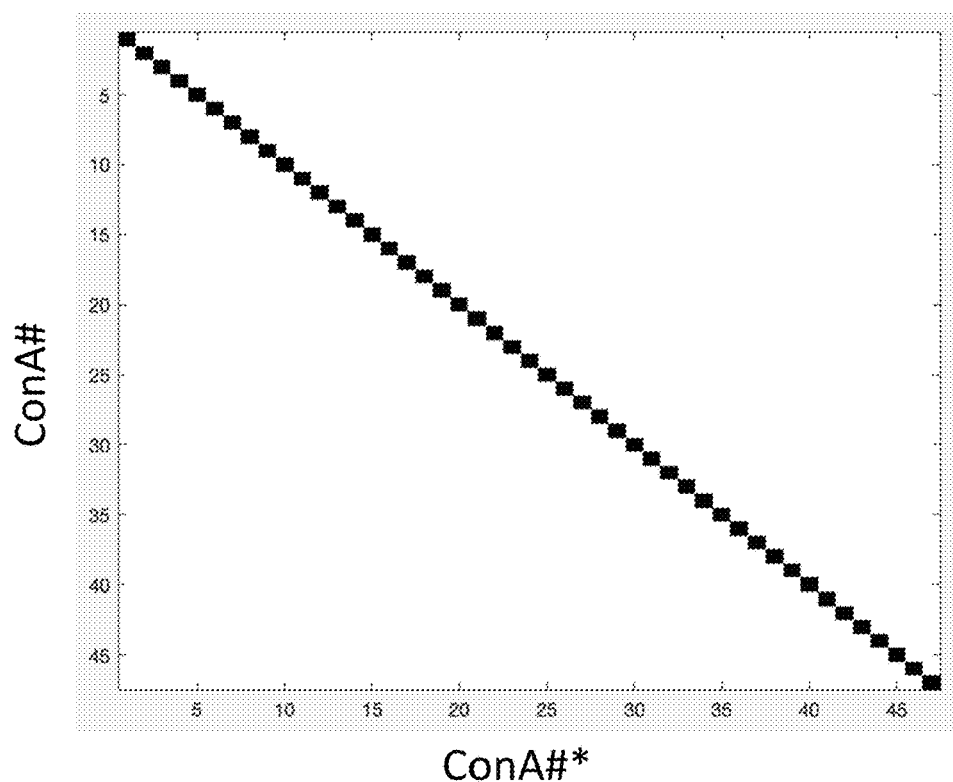
FIG. 3A depicts an example simulation result using the methods described herein.
Figure 3B:
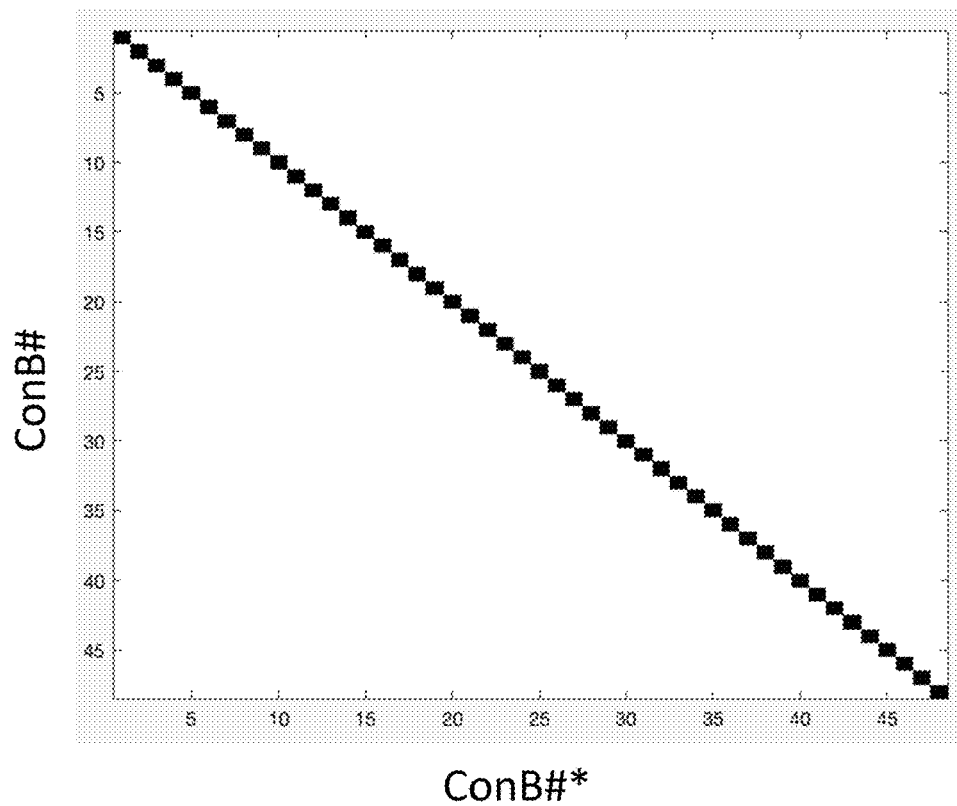
FIG. 3B depicts an example simulation result using the methods described herein.

In this example, a thermodynamics-based algorithm is provided to design codon-diversified ConA # and ConB # sequences. The algorithm is written in MATLAB language. Some variables and custom functions used in this algorithm will be described in the 'note' section below, with the rest described in the comment of the code or self-explanatory to skilled artisans. Some custom functions rely on thermodynamics-based simulation of DNA hybridization using publicly available thermodynamic parameters (e.g., $\Delta H$ and $\Delta S$ for base pair stacks) and models (e.g., $\Delta S$ as a function of loop size). These parameters and models have been extensively published by John SantaLucia Jr. Skilled artisan can readily write these functions from scratch or with the help of publicly available software packages such as NUPACK. The algorithm contains two stages: initial design and codon diversification, which are described in Script1 and Script2, respectively. In initial design, ConA # and ConB # sequences are designed according to the original TRAV or TRBV sequences. Hybridization yield of every ConX # to every ConX #* is then computed to serve as a baseline (FIG. 2A and FIG. 2B). FIG. 2A shows hybridization yield of the connector sequences designed according to the original TRAV sequences without codon diversification (ConA # to ConA #*). FIG. 2B shows hybridization yield of the connector sequences designed according to the original TRBV sequences without codon diversification (ConB # to ConB #*). During codon diversification, the codon choices of the last ~60 bases of some of the TRXV #_GL are randomized, and ConX # sequences that allow specific hybridization are chosen. Next, hybridization yield of every ConX # to every ConX #* using the codon-diversified sequence set is then calculated to see if the codon diversification was successful (FIG. 3A and FIG. 3B). FIG. 3A shows hybridization yield of the codon-diversified connector sequences (ConA # to ConA #*). FIG. 3B shows hybridization yield of the codon-diversified connector sequences (ConB # to ConB #*).

| Script 1: Initial design. |
|---|

```
clear
fHybTemp = 60; %Hybridization temperature (unit: degree C)
fConcNa = 125; %Sodium ion concentration (unit: mM)
fConcMg = 3; % Magnesium ion concentration (unit: mM)
fConcQB = 5; %Concentration of ConA# or ConB#
%Store the parameters above in struPara.
struPara.fHybTemp = fHybTemp;
struPara.fConcNa = fConcNa;
struPara.fConcMg = fConcMg;
struPara.fConcQB = fConcQB;
cChain = 'B'; % The value can be A or B to design initial ConA and
ConB sequences respectively.
cFileGeneSeq = sprintf('hsTR %sV_UTR200-L-
V_Sorted_FOnly.txt', cChain); % See notes
% Read V gene sequences
fidGene = fopen(cFileGeneSeq);
raGeneInfo = textscan(fidGene,'%s\t %d\t %d\t %s','Headerlines',1);
fclose(fidGene);
% Initialize the cell array (ra1on1s) that stores the initially
designed ConA or ConB sequences
iTotalNumOfGene = size(raGeneInfo{1},1);
ra1on1s{1} = -ones(iTotalNumOfGene,2);
ra1on1s{2} = cell(iTotalNumOfGene,4);
for iGeneNum = 1:iTotalNumOfGene
    fprintf('Designing 1on1 for gene #%u.\n',iGeneNum);
    cGeneName = raGeneInfo{1}{iGeneNum};
    cGeneSeq = raGeneInfo{4}{iGeneNum};
    iLStart = raGeneInfo{2}(iGeneNum);
    cCDS = cGeneSeq(iLStart:end);
    cAA = nt2aa(cCDS);
    iPosAAConservedC = find(cAA=='C',1,'last');
    viPosNTConservedC = iPosAAConservedC*3-2:iPosAAConservedC*3;
    vPosOfTinCys(iGeneNum) = viPosNTConservedC(1); % Position of the
first nucleotide of the codon for the conserved Cys at the N
terminus of CDR3
    cSA60 = cCDS(viPosNTConservedC(1)-59:viPosNTConservedC(1));
    ra1on1ofThisGene = fun_Design1on1(cSA60,struPara); % See notes
    disp(ra1on1ofThisGene{1})
    ra1on1s{1}(iGeneNum,:) = ra1on1ofThisGene{1};
    ra1on1s{2}(iGeneNum,:) = ra1on1ofThisGene{2};
end
%%
cTime = datestr(now);
cTime(cTime==' ')='_';
cTime(cTime==':')='_' ;
save(['IniDesign1on1_',cChain,num2str(fHybTemp),'_',cTime,'.mat'],'v
PosOfTinCys','cChain','raGeneInfo','ra1on1s','struPara');
%% Compute cross hybridization yield
xFracBoundHyb_THyb = -ones(iTotalNumOfGene,iTotalNumOfGene);
for iSimQB = 1:iTotalNumOfGene
    for iDE = 1:iTotalNumOfGene
        if xFracBoundHyb_THyb(iSimQB,iDE) >= 0
            continue;
        end
        cSimQB = ra1on1s{2}{iSimQB,3}; % cSimQB = sequence of ConA/B
        cDE = ra1on1s{2}{iDE,4}; % cDE = sequence of ConA/B*
        fThisFracBound_THyb =
NP_GetBoundFrac(cSimQB,fConcQB,cDE,fConcQB/100,...
            fHybTemp,'Na',fConcNa,'Mg',fConcMg); % See note
        xFracBoundHyb_THyb(iSimQB,iDE) = fThisFracBound_THyb;
    end
end
%%
save('IniDesign.mat','xFracBoundHyb_THyb','xFracBoundHyb_THybMinus5o
C');
figure;
colormap(gray);
imagesc(1-xFracBoundHyb_THyb);
```

Notes for Script1:

The files "hsTRAV_UTR200-L-V_Sorted_FOnly.txt" and "hsTRBV_UTR200-L-V_Sorted_FOnly.txt" are TSV files recording the sequences of all TCR V genes annotated as 'functional' in IMGT database. Each file has 4 columns, the first column is the name of the V gene, the 4th column is the sequence of the V gene cDNA sequencing starting from ~200 nt upstream of the start codon (of L-PART1), the 2nd column is the position of the first nucleotide of the start codon. The 3rd column is the position of the first nucleotide of the V gene (e.g., after L-PART2).

The function "fun_Design1on1" returns the ConA or ConB sequence using two inputs: (1) the variable cSA60 which records the last 60 bases of the TRXV #_GL, and (2)

parameters for thermodynamic modeling stored in the variable struPara. Briefly, the function finds the shortest continuous subsequence of cSA60 ending at the 3' end of cSA60 (noted as ConX) that satisfies the following statement: when 5 nM of a first DNA oligonucleotide having sequence ConX and 0.05 nM of a second DNA oligonucleotide having sequence ConX* is mixed, more than 97% of the second oligonucleotide is predicted to be bound to the first oligonucleotide at the temperature, sodium ion concentration and magnesium ion concentration defined by struPara.fHybTemp, struPara.fConcNa, and struPara.fConcMg respectively. The output of this function (ra1on1ofThisGene) is a cell array with two cells, the first cell, ra1on1ofThisGene{1} is a 1×2 vector, where ra1on1ofThisGene{1}(1) is an output not used in this example, and ra1on1ofThisGene{1}(2) is the position of the first base of ConX on cSA60. ra1on1ofThisGene{2} is a 1×4 cell array, where ra1on1ofThisGene{2}{1} and ra1on1ofThisGene{2}{2} are not used in this example, ra1on1ofThisGene{2}{3} is the sequence of ConX, and ra1on1ofThisGene{2}{4} is the sequence of ConX*. A skilled artisan can write this function as described above.

The function "NP_GetBoundFrac" returns the fraction of a first DNA oligonucleotide having sequence ConX* that is bound to a second DNA oligonucleotide having sequence ConX when 5 nM (as recorded by fConcQB) of the second nucleotide and 0.05 nM (as recorded by fConcQB/100) of the first nucleotide is mixed at 60° C. (as recorded by fHybTemp) and reach equilibrium in the presence of 125 mM $Na^+$ (as recorded by fConcNa) and 5 mM $Mg^{++}$ (as recorded by fConcMg).

The image produced by this script shows a gray scale heat map of how what fraction of ConX #* is predicted to be bound to ConX # when 0.05 nM of ConX #* is mixed with 5 nM of ConX # at the condition described above. As shown in FIG. 2A and FIG. 2B, substantial cross-binding (e.g., mis-connection) is present especially for TRBV (FIG. 2B).

Script 2. Codon diversification

```
clear;
load('IniDesign.mat');
fConcQB = struPara.fConcQB;
fConcNa = struPara.fConcNa;
fConcMg = struPara.fConcMg;
fHybTemp = struPara.fHybTemp;
fCodonFreqThreshold = 0.15; % Lowest allowed codon frequency
fSSThreshold = 0.6;
fCrossAssemblyThreshold = 0.02; % Lowest allowed level of mis-
connection
iMaxLengthDE = 35; % Maximum allowed length of ConX
struParaDiv.fCodonFreqThreshold = fCodonFreqThreshold;
struParaDiv.fSSThreshold = fSSThreshold;
struParaDiv.fCrossAssemblyThreshold = fCrossAssemblyThreshold;
struParaDiv.iMaxLengthDE = iMaxLengthDE;
%%% Initiate
ra1on1NewDesign = cell(1,2);
iTotalNumOfGene = size(ra1on1s{1},1);
xCrossPrimeAlreadyDesigned_Hyb_THyb = -ones(iTotalNumOfGene);
%%
for iGeneToModify = 1:iTotalNumOfGene
    cSA60 = ra1on1s{2}{iGeneToModify,1};
    cAAInFrame = nt2aa(cSA60(3:59));
    fprintf('%s\n',cSA60);
    bHaveYouTriedInitialDesign = false;
    while(1)
        if ~bHaveYouTriedInitialDesign
            ra1on1ofThisGene{1} = ra1on1s{1}(iGeneToModify,:);
            ra1on1ofThisGene{2} = ra1on1s{2}(iGeneToModify,:);
            bHaveYouTriedInitialDesign = true;
        else %Randomize
            cTrialMiddle57 =
fun_aa2nt(cAAInFrame,raCodonTable,fCodonFreqThreshold); % See note
            cAAToMakeSure =
nt2aa(cTrialMiddle57, 'AlternativeStartCodons','false');
            if ~strcmpi(cAAInFrame,cAAToMakeSure)
                error('something is wrong');
            end
            cTrialSA60 = [cSA60(1:2),cTrialMiddle57,'T'];
            fprintf('%s\n',cTrialSA60);
            ra1on1ofThisGene = fun_Design1on1(cTrialSA60,struPara);
        end
        iStartPosBM = ra1on1ofThisGene{1}(2);
        cTrialSimQB = ra1on1ofThisGene{2}{3};
        cTrialDE = ra1on1ofThisGene{2}{4};
        % Check DE length
        iLeftestStartPosBM = 60 - iMaxLengthDE + 1;
        if iStartPosBM < iLeftestStartPosBM
            fprintf('DE too long\n');
            continue;
        end
        %%
        vRow_THyb = -ones(1,iGeneToModify);
        vColumn_THyb = -ones(iGeneToModify,1);
        for iDE = 1:iGeneToModify
```

| Script 2. Codon diversification |
|---|
| ```
        if iDE ~= iGeneToModify
            cDE = ra1on1NewDesign{2}{iDE,4};
        else
            cDE = cTrialDE;
        end
        fFracHyb__THyb =
NP__GetBoundFrac(cTrialSimQB,fConcQB,cDE,fConcQB/100,...
            fHybTemp,'Na',fConcNa,'Mg',fConcMg);
        vRow__THyb(iDE) = fFracHyb__THyb;
    end
    for iQB = 1:iGeneToModify
        if iQB ~= iGeneToModify
            cExtSimQB = ra1on1NewDesign{2}{iQB,2};
        else
            cExtSimQB = cTrialExtSimQB;
        end
        fFracHyb__THyb =
NP__GetBoundFrac(cExtSimQB,fConcQB,cTrialDE,fConcQB/100,...
            fHybTemp,'Na',fConcNa,'Mg',fConcMg);
        vColumn__THyb(iQB) = fFracHyb__THyb;
    end
    vRowToUse = vRow__THyb;
    vColumnToUse = vColumn__THyb;
    if vRowToUse(end) >= 0.5 && sum(vRowToUse(1:end-
1))<fCrossAssemblyThreshold && ...
            vColumnToUse(end) >= 0.5 && sum(vColumnToUse(1:end-
1))<fCrossAssemblyThreshold
        ra1on1NewDesign{1}(iGeneToModify,:) =
ra1on1ofThisGene{1};
        ra1on1NewDesign{2}(iGeneToModify,:) =
ra1on1ofThisGene{2};
        xCrossPrimeAlreadyDesigned__Hyb__THyb(iGeneToModify,1:iGeneToModify) =
vRow__THyb;
        xCrossPrimeAlreadyDesigned__Hyb__THyb(1:iGeneToModify,iGeneToModify) =
vColumn__THyb;
        break;
        end
    end
end
%%
figure;
colormap(gray)
imagesc(1-xCrossPrimeAlreadyDesigned__Hyb__THyb);
``` |

Notes for Script2:

The function "fun_aa2nt" returns a polynucleotide sequence that encodes the same polypeptide as the input sequence cAAInFrame, using the codon table information provided by the input raCodonTable, and lowest allowed codon frequency provided by the input fCodonFreqThreshold.

The image produced by this script shows a gray scale heat map of what fraction of ConX #* is predicted to be bound to ConX # when 0.05 nM of ConX #* is mixed with 5 nM of ConX # at the condition described above after codon diversification. As shown in FIG. 3A and FIG. 3B, only specific hybridization is predicted to happen noticeably. Thus, this example shows the codon diversification scheme is feasible, and shows how to obtain codon diversified ConA and ConB sequences.

Example 3. Connector Sequences Derived from Mouse TRAV and TRBV Genes

This example provides codon-diversified connector sequences derived from mouse TRAV and TRBV genes. Similar to the above examples, ConA is the connector for a specific TRAV sequence, and ConB is the connector for a specific TRBV sequence. The codon diversification was performed using the same methods as described in Example 2. Table 1 shows codon-diversified connector sequences derived from mouse TRAV genes. Table 2 shows codon-diversified connector sequences derived from mouse TRBV genes. In Tables 1 and 2, The gene name and accession number is shown for each V gene in the first column, and the corresponding connector sequence is shown in the second column.

TABLE 1

| | Connector sequences derived from mouse TRAV genes | |
|---|---|---|
| SEQ ID NO: | Connector of mouse TRAV genes | Connector Sequence |
| 1 | >ConA of Trav1\|ENSMUST00000103567.5 | TCAAAGACTCTGCCTCATACCTCT |

TABLE 1-continued

Connector sequences derived from mouse TRAV genes

| SEQ ID NO: | Connector of mouse TRAV genes | Connector Sequence |
|---|---|---|
| 2 | >ConA of Trav2\|ENSMUST00000196939.1 | CTGAGAGACGCAGCTGTGTATTACT |
| 3 | >ConA of Trav3-1\|ENSMUST00000103569.2 | GGGGACTCAGCCGTGTACTTCT |
| 4 | >ConA of Trav3-3\|ENSMUST00000181768.2 | GGTGACTCCGCAGCCTATTTCT |
| 5 | >ConA of Trav3-4\|ENSMUST00000103670.3 | TGGGGATAGCGCAGTCTATTTCT |
| 6 | >ConA of Trav3d-3\|ENSMUST00000196023.1 | CCGGAGACAGCGCAGTTTATTTTT |
| 7 | >ConA of Tray3n-3\|ENSMUST00000197557.1 | GGTGACAGCGCCGTCTATTTTT |
| 8 | >ConA of Trav4-2\|ENSMUST00000103637.5 | TGGAGGACTCAGGCACTTACTTCT |
| 9 | >ConA of Trav4-3\|ENSMUST00000103655.2 | TGGAGGACTCTGGGACATACTTTT |
| 10 | >ConA of Trav4-4-dv10\|ENSMUST00000103663.5 | TGGAGGACTCTGGCACCTATTTTT |
| 11 | >ConA of Trav4d-3\|ENSMUST00000103592.1 | ACTCGAGGATTCCGGTACTTATTTCT |
| 12 | >ConA of Trav4d-4\|ENSMUST00000103600.2 | GAAGACTCCGGGACCTACTTTT |
| 13 | >ConA of Trav4n-3\|ENSMUST00000103618.1 | GCTGGAGGATTCCGGAACCTATTTCT |
| 14 | >ConA of Trav4n-4\|ENSMUST00000103627.2 | CTCGAAGATAGCGGCACATATTTTT |
| 15 | >ConA of Trav5-1\|ENSMUST00000103570.1 | GCCTGGTGATAGCGCAATATACTTCT |
| 16 | >ConA of Trav5d-4\|ENSMUST00000179701.1 | TGGCGACTCTGCAATGTACTTCT |
| 17 | >ConA of Trav5n-4\|ENSMUST00000179997.1 | CCCGGAGACTCTGCTATGTATTTTT |
| 18 | >ConA of Trav6-1\|ENSMUST00000103571.1 | GGAATCCGATAGCGCAGTCTATTACT |
| 19 | >ConA of Trav6-2\|ENSMUST00000198058.1 | TCCGACAGCGCTGTCTACTACT |
| 20 | >ConA of Trav6-3\|ENSMUST00000180549.2 | AAGAGATTGATAGCGCTGTTTACTACT |
| 21 | >ConA of Trav6-4\|ENSMUST00000184650.1 | AGGAATCTGATTCCGCAGTCTATTTTT |
| 22 | >ConA of Trav6-5\|ENSMUST00000181210.2 | AGAATCTGATAGCGCCGTTTATTATT |
| 23 | >ConA of Trav6-6\|ENSMUST00000103584.3 | GTCCGACTCCGCAGTCTACTACT |
| 24 | >ConA of Trav6-7-dv9\|ENSMUST00000103638.5 | AGGAGTCTGATTCTGCAGTCTACTATT |
| 25 | >ConA of Trav6d-3\|ENSMUST00000181483.2 | CCAAGAAATAGATTCCGCAGTCTACTACT |
| 26 | >ConA of Trav6d-4\|ENSMUST00000180717.2 | GTCTGACAGCGCAGTCTACTTCT |

TABLE 1-continued

Connector sequences derived from mouse TRAV genes

| SEQ ID NO: | Connector of mouse TRAV genes | Connector Sequence |
|---|---|---|
| 27 | >ConA of Trav6d-5\|ENSMUST00000180687.2 | AGGAAAGCGATTCTGCAGTCTATTACT |
| 28 | >ConA of Trav6d-6\|ENSMUST00000197754.1 | AAGAGTCTGACTCCGCAGTTTATTATT |
| 29 | >ConA of Trav6d-7\|ENSMUST00000178650.2 | AGAATCCGACTCTGCAGTTTACTATT |
| 30 | >ConA of Trav6n-5\|ENSMUST00000103611.1 | GAGTCTGATAGCGCTGTGTACTACT |
| 31 | >ConA of Trav6n-6\|ENSMUST00000181793.2 | GAATCTGACTCTGCCGTTTACTATT |
| 32 | >ConA of Trav6n-7\|ENSMUST00000179607.2 | AGTCCGACTCTGCTGTGTACTACT |
| 33 | >ConA of Trav7-1\|ENSMUST00000198019.1 | CCATCTGATTCCGCACTGTATTTCT |
| 34 | >ConA of TRAV7-2\|AC004407 | ACCTTCTGATAGCGCTCTCTATTTTT |
| 35 | >ConA of Trav7-3\|ENSMUST00000177622.3 | CCTTCTGATTCTGCACTGTACCTGT |
| 36 | >ConA of Trav7-4\|ENSMUST00000181728.2 | CCAAGCGATTCTGCACTGTATTTTT |
| 37 | >ConA of Trav7-5\|ENSMUST00000200609.1 | CCTCTGACTCTGCAGTCTACCTCT |
| 38 | >ConA of Trav7-6\|ENSMUST00000103641.5 | CCCAGCGACTCTGCAGTTTATCTCT |
| 39 | >ConA of Trav7d-2\|ENSMUST00000200127.1 | CCGACAGCGCACTCTACCTGT |
| 40 | >ConA of Trav7d-3\|ENSMUST00000179789.3 | TTCCGACTCTGCACTGTATCTGT |
| 41 | >ConA of Trav7d-4\|ENSMUST00000178768.3 | TCCGATAGCGCCCTGTATTTCT |
| 42 | >ConA of Trav7d-5\|ENSMUST00000197128.1 | CTCCGATTCCGCACTCTATCTCT |
| 43 | >ConA of Trav7D-6\|ENSMUST00000196756.1 | CCTCCGATAGCGCTGTTTATCTCT |
| 44 | >ConA of Trav7n-4\|ENSMUST00000103609.1 | GCGACAGCGCCCTGTACTTTT |
| 45 | >ConA of Trav7n-5\|ENSMUST00000199753.1 | CCCTCTGATAGCGCACTGTATCTCT |
| 46 | >ConA of Trav7n-6\|ENSMUST00000178100.2 | CTTCTGACAGCGCTGTGTATCTGT |
| 47 | >ConA of Trav8-1\|ENSMUST00000103643.3 | GCGAGGACACAGCTGTTTACTTTT |
| 48 | >ConA of TRAV8-2\|AC004096 | AGTGCGAAGATACAGCAGTTTACTTCT |
| 49 | >ConA of Trav8d-1\|ENSMUST00000103580.3 | CGGTGTGAGGATACTGCTGTTTATTTCT |
| 50 | >ConA of Trav8d-2\|ENSMUST00000198439.4 | CGAAGATACCGCCGTCTACTTTT |
| 51 | >ConA of Trav8n-2\|ENSMUST00000103632.3 | GGCAACTGACACAGCAGTCTACTTTT |

TABLE 1-continued

Connector sequences derived from mouse TRAV genes

| SEQ ID NO: | Connector of mouse TRAV genes | Connector Sequence |
|---|---|---|
| 52 | >ConA of Trav9-1\|ENSMUST00000103581.5 | GAGCGATTCTGCCGTTTACTTCT |
| 53 | >ConA of Trav9-2\|ENSMUST00000103654.2 | TCCGATTCCGCCGTGTATTTTT |
| 54 | >ConA of Trav9-4\|ENSMUST00000103662.5 | TTGGTCTGATTCTGCAGTTTACTTTT |
| 55 | >ConA of Trav9d-1\|ENSMUST00000178426.3 | GGTCTGATTCCGCTGTCTACTTTT |
| 56 | >ConA of Trav9d-2\|ENSMUST00000199746.4 | CTGGTCTGACTCTGCTGTTTATTTTT |
| 57 | >ConA of Trav9d-3\|ENSMUST00000178252.2 | GGTCCGACTGGGCAGTCTATTTTT |
| 58 | >ConA of Trav9d-4\|ENSMUST00000200548.1 | TGGTCTGATTCTGCCGTCTATTTCT |
| 59 | >ConA of Trav9n-2\|ENSMUST00000198913.4 | AGCGACTCTGCCGTGTATTTCT |
| 60 | >ConA of Trav9n-3\|ENSMUST00000177705.2 | GAGCGATTGGGCAGTCTACTTTT |
| 61 | >ConA of Trav9n-4\|ENSMUST00000103626.2 | TGGTCCGATTCTGCTGTCTATTTTT |
| 62 | >ConA of Trav10\|ENSMUST00000103583.4 | AGCCTGAAGATTCAGCCATCTACTTCT |
| 63 | >ConA of Trav10d\|ENSMUST00000103646.4 | CCCGAGGACTCTGCTATTTACTTCT |
| 64 | >ConA of Trav10n\|ENSMUST00000103612.1 | ACAGCCAGAAGATTCTGCAATATACTTCT |
| 65 | >ConA of Trav11\|ENSMUST00000103585.3 | GCTCGATGACACAGCTACATACATCT |
| 66 | >ConA of TRAV11D\|AC004101 | TCCTGGATGATACTGCAACATACATAT |
| 67 | >ConA of Trav12-1\|ENSMUST00000200115.1 | CTCTCTGACTCTGCACTGTACTACT |
| 68 | >ConA of Trav12-2\|ENSMUST00000180972.2 | ACTGTCTGACTCTGCACTCTATTACT |
| 69 | >ConA of Trav12-3\|ENSMUST00000103657.5 | CTGTCCGATTCTGCACTCTACTACT |
| 70 | >ConA of Trav12d-1\|ENSMUST00000181360.2 | AACTGTCTGATTCTGCTCTGTACTATT |
| 71 | >ConA of Trav12d-2\|ENSMUST00000103593.2 | TCCGACTCCGCTCTGTATTTTT |
| 72 | >ConA of Trav12d-3\|ENSMUST00000177703.2 | AGCGACTCTGCCCTCTACTACT |
| 73 | >ConA of Trav12n-1\|ENSMUST00000198682.1 | TCTCTGACTCCGCTCTCTACTACT |
| 74 | >ConA of Trav12n-2\|ENSMUST00000103619.2 | TCTCTGATTCTGCCCTCTACTTTT |
| 75 | >ConA of Trav12n-3\|ENSMUST00000179583.2 | GCTCTCCGATTCTGCTCTGTATTATT |
| 76 | >ConA of Trav13-1\|ENSMUST00000103651.3 | GACAACAGACTCAGGCACTTATCTCT |

TABLE 1-continued

Connector sequences derived from mouse TRAV genes

| SEQ ID NO: | Connector of mouse TRAV genes | Connector Sequence |
|---|---|---|
| 77 | >ConA of Trav13-2\|ENSMUST00000103658.3 | AACAACTGACTCTGGCACATATTTTT |
| 78 | >ConA of TRAV13-3\|AC003995 | CACTGATAGCGGAACCTACCTCT |
| 79 | >ConA of Trav13-4-dv7\|ENSMUST00000180380.2 | TGACAGCGGCACCTACCTGT |
| 80 | >ConA of Trav13-5\|ENSMUST00000103671.3 | ACTACAGATTCCGGCACTTACTTCT |
| 81 | >ConA of Trav13d-1\|ENSMUST00000103588.3 | GCCAGATAACTGATTCTGGTACTTACCTGT |
| 82 | >ConA of Trav13d-2\|ENSMUST00000197954.1 | ACAACTGACAGCGGAACATATCTCT |
| 83 | >ConA of Trav13d-3\|ENSMUST00000179512.2 | AAATAACAGATAGCGGTACATACCTGT |
| 84 | >ConA of Trav13d-4\|ENSMUST00000196079.1 | CCACAGATTCTGGCACCTACTTCT |
| 85 | >ConA of Trav13n-1\|ENSMUST00000198359.1 | ACTGACTCCGGAACCTACCTCT |
| 86 | >ConA of Trav13n-2\|ENSMUST00000196941.1 | ACCGACTCTGGCACTTACCTGT |
| 87 | >ConA of Trav13n-3\|ENSMUST00000179580.2 | AATCACAGACTCTGGAACCTATCTGT |
| 88 | >ConA of Trav13n-4\|ENSMUST00000196105.1 | CCAAATTACCGATTCTGGTACATACCTCT |
| 89 | >ConA of Trav14-1\|ENSMUST00000198297.1 | CGGAGATAGCGCCACATACTTTT |
| 90 | >ConA of Trav14-2\|ENSMUST00000179267.3 | AACCTGGAGATTCTGCAACATATTTCT |
| 91 | >ConA of Trav14-3\|ENSMUST00000103589.5 | CTGGGGACTCTGCAACTTACTTCT |
| 92 | >ConA of Trav14d-1\|ENSMUST00000181038.2 | CCTGGAGACTCAGCTACCTACTTCT |
| 93 | >ConA of Trav14d-2\|ENSMUST00000196802.1 | CCGGGGATAGCGCTACTTATTTTT |
| 94 | >ConA of Trav14d-3-dv8\|ENSMUST00000103608.3 | CCTGGAGATTCCGCAACTTACTTTT |
| 95 | >ConA of Trav14n-1\|ENSMUST00000177578.1 | CCAGGGGATTCTGCTACCTATTTTT |
| 96 | >ConA of Trav14n-2\|ENSMUST00000197614.1 | CCCGGAGATTCTGCCACTTATTTCT |
| 97 | >ConA of Trav14n-3\|ENSMUST00000103652.4 | CTGGCGACAGCGCTACTTATTTCT |
| 98 | >ConA of Trav15-1-dv6-1\|ENSMUST00000103653.2 | AACCAGACGATTCGGGAAAGTATTTCT |
| 99 | >ConA of Trav15-2-dv6-2\|ENSMUST00000103660.3 | CAGAGGATTCAGGGACGTACTTCT |
| 100 | >ConA of Trav15d-1-dv6d-1\|ENSMUST00000103616.4 | CCAGACGACTCCGGAAAGTACTTTT |
| 101 | >ConA of Trav15d-2-dv6d-2\|ENSMUST00000199800.1 | CCGAGGACTCCGGTACATACTTCT |

TABLE 1-continued

Connector sequences derived from mouse TRAV genes

| SEQ ID NO: | Connector of mouse TRAV genes | Connector Sequence |
|---|---|---|
| 102 | >ConA of Trav15n-1\|ENSMUST00000103590.3 | AACCCGATGACTCTGGTAAGTATTTTT |
| 103 | >ConA of Trav15n-2\|ENSMUST00000199112.1 | GCCAGAAGACTCCGGTACATATTTTT |
| 104 | >ConA of Trav16\|ENSMUST00000103667.5 | TCAAATTGAAGATTCTGCAGTCTACTTTT |
| 105 | >ConA of Trav16d-dv11\|ENSMUST00000103606.1 | GATTGAGGACTCGGCAGTATATTTCT |
| 106 | >ConA of Trav16n\|ENSMUST00000199280.1 | AAATCGAAGACTCTGCAGTTTACTTTT |
| 107 | >ConA of Trav17\|ENSMUST00000103672.8 | GAGCGACTCAGCCAAGTACTTCT |
| 108 | >ConA of Trav18\|ENSMUST00000103673.10 | AGGGGATGCTGGGATCTACTTTT |
| 109 | >ConA of Trav19\|ENSMUST00000103674.5 | CCCGAAGATACAGCTGTCTACCTGT |
| 110 | >ConA of Trav21-dv12\|ENSMUST00000180938.2 | AGGGACGCAGCAGTCTATCATT |
| 111 | >ConA of Trav23\|ENSMUST00000199137.1 | GCCACTCTGCCATCTACTTCTGT |

TABLE 2

Connector sequences derived from mouse TRBV genes

| SEQ ID NO: | Connector of mouse TRBV genes | Connector sequence |
|---|---|---|
| 112 | >ConB of Trbv1\|ENSMUST00000103262.2 | GGCGCACACTGTACTGCACAT |
| 113 | >ConB of Trbv2\|ENSMUST00000103263.2 | TGATGACTCGGCCACATACTTCT |
| 114 | >ConB of Trbv3\|AE000663 | TGGAGGACTCAGCTGTGTACTTCT |
| 115 | >ConB of Trbv4\|ENSMUST00000103265.4 | ACCAGAAGATAGCGCAGTTTATCTGT |
| 116 | >ConB of Trbv5\|ENSMUST00000103266.2 | ATCCAGAAGACTCAGCTGTCTATTTTT |
| 117 | >ConB of Trbv12-1\|M15614 | TCGAAGATAGCGCCATGTACTTTT |
| 118 | >ConB of Trbv12-2\|M15613 | ACTGGAAGATAGCGCTGTGTATTTCT |
| 119 | >ConB of Trbv13-1\|ENSMUST00000194399.1 | AAGCCAGACCAGCCTCTATTTTT |
| 120 | >ConB of Trbv13-2\|ENSMUST00000103270.3 | CCCCTCTCAGACATCAGTGTACTTCT |
| 121 | >ConB of Trbv13-3\|ENSMUST00000103271.1 | GCCAGACCGCCGTGTATTTCT |
| 122 | >ConB of Trbv14\|ENSMUST00000103272.3 | GGCGACACAGCCACCTATCTCT |
| 123 | >ConB of Trbv15\|ENSMUST00000103273.2 | GCCTAAAGACAGCGCTGTTTATCTCT |

TABLE 2-continued

Connector sequences derived from mouse TRBV genes

| SEQ ID NO: | Connector of mouse TRBV genes | Connector sequence |
|---|---|---|
| 124 | >ConB of Trbv16\|ENSMUST00000103274.3 | CCAGGACTCAGCGGTGTATCTTT |
| 125 | >ConB of Trbv17\|ENSMUST00000103275.3 | GCCTAGAGTATTCTGCCATGTACCTCT |
| 126 | >ConB of Trbv19\|ENSMUST00000103276.2 | AAAAATGAGATGGCAGTCTTCCTCT |
| 127 | >ConB of Trbv20\|ENSMUST00000103277.1 | CGAGGATAGGGGCCTGTATCTCT |
| 128 | >ConB of Trbv23\|ENSMUST00000193997.5 | GCAGAAGACTCAGCACTGTACTTGT |
| 129 | >ConB of Trbv24\|IMGT | GACGACTCAGCACTGTACCTCT |
| 130 | >ConB of Trbv26\|ENSMUST00000193064.1 | GGGGACTCCGCACTCTATCTCT |
| 131 | >ConB of Trbv29\|ENSMUST00000103281.2 | AAACAAACCAGACATCTGTGTACTTCT |
| 132 | >ConB of Trbv30\|ENSMUST00000103282.2 | GGCCTGGAGACAGCAGTATCTATTTCT |
| 133 | >ConB of Trbv31\|ENSMUST00000193003.1 | TCAGCCATAGCGGTTTTTACCTCT |

Figure 10A:
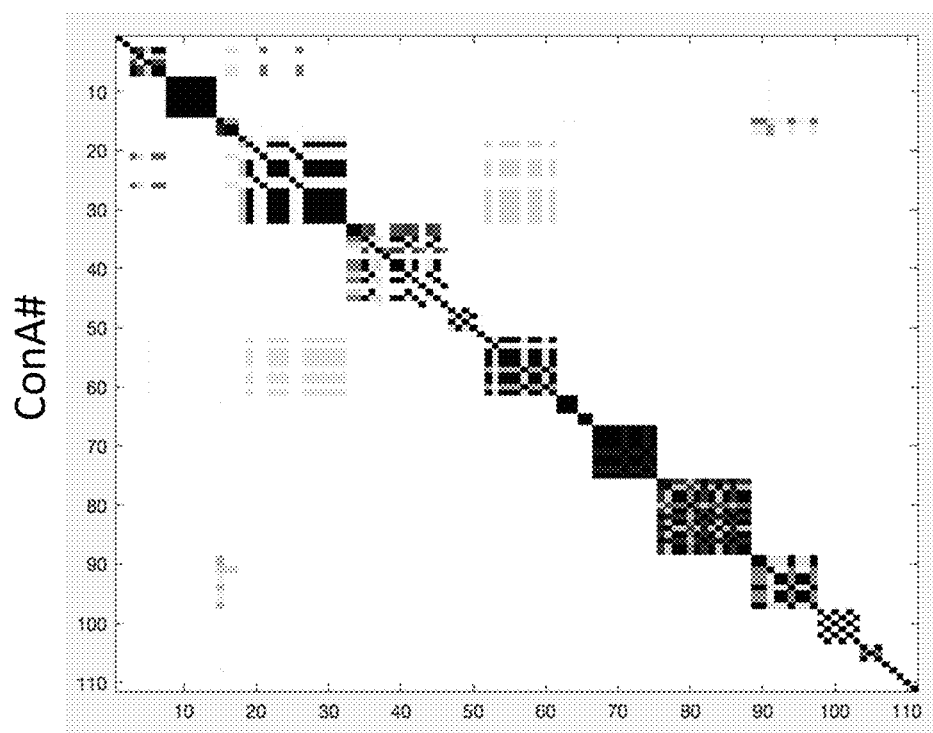
FIG. 10A depicts an example simulation result using the methods described herein.
Figure 10B:
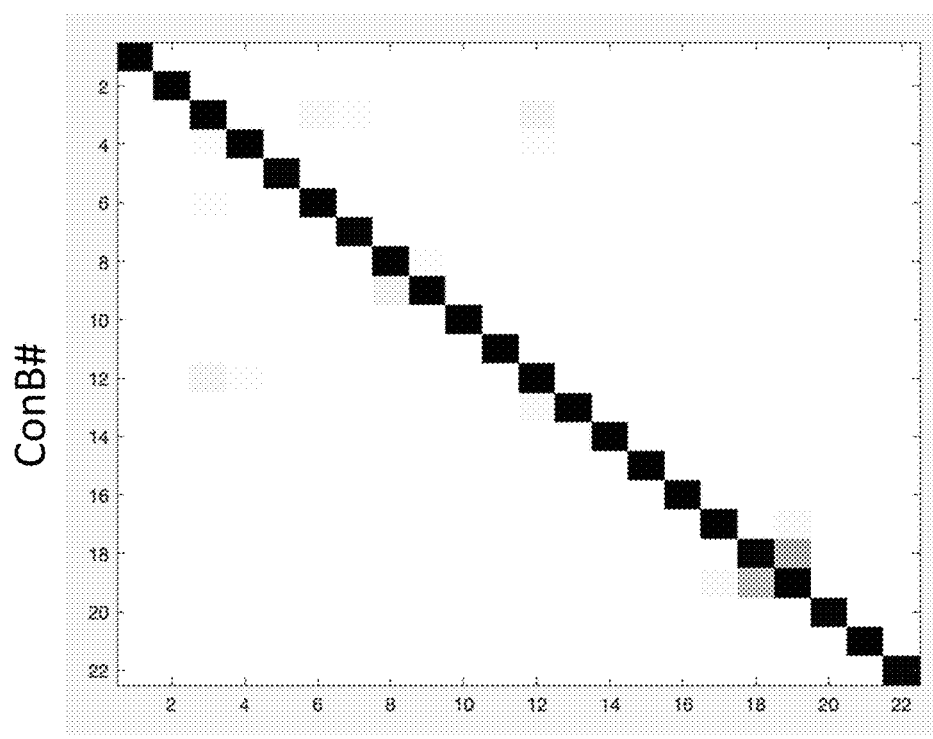
FIG. 10B depicts an example simulation result using the methods described herein.
Figure 11A:
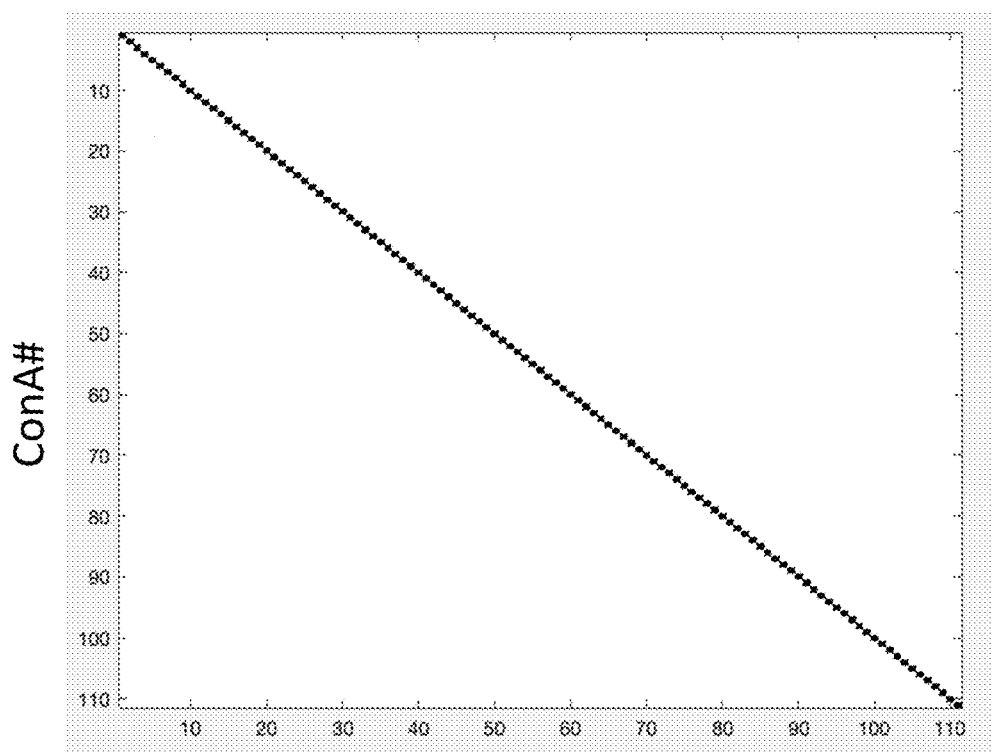
FIG. 11A depicts an example simulation result using the methods described herein.
Figure 11B:
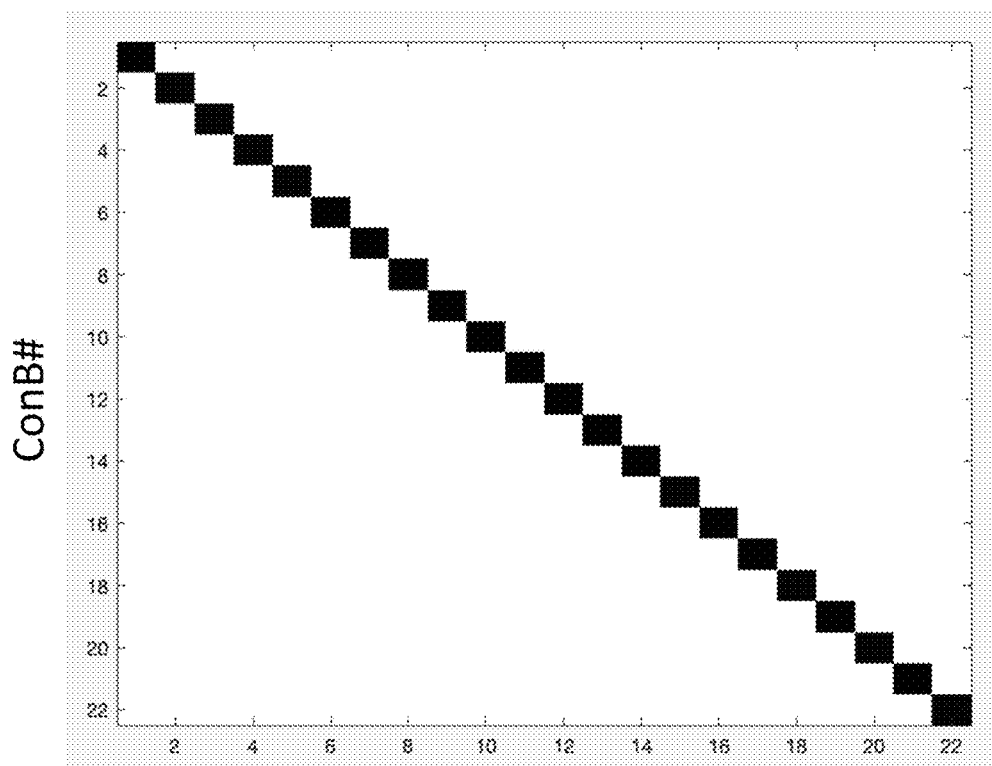
FIG. 11B depicts an example simulation result using the methods described herein.

In the initial design, ConA # and ConB # sequences are designed according to the original TRAV or TRBV sequences. As used herein, the symbol # denotes a numerical ID of a TRAV or TRBV gene. Hybridization yield of every ConX # to every ConX #* is then computed to serve as a baseline (FIG. 10A and FIG. 10B). FIG. 10A shows hybridization yield of the connector sequences designed according to the original TRAV sequences without codon diversification (ConA # to ConA #*). FIG. 10B shows hybridization yield of the connector sequences designed according to the original TRBV sequences without codon diversification (ConB # to ConB #*). During codon diversification, the codon choices of the last ~60 bases of some of the TRXV #_GL are randomized, and ConX # sequences that allow specific hybridization are chosen. Next, hybridization yield of every ConX # to every ConX #* using the codon-diversified sequence set is then calculated to see if the codon diversification was successful (FIG. 11A and FIG. 11B). FIG. 11A shows hybridization yield of the codon-diversified connector sequences (ConA # to ConA #*). FIG. 11B shows hybridization yield of the codon-diversified connector sequences (ConB # to ConB #*).

Example 4. Connector Sequences with Arbitrary Sequences

Table 3 provides arbitrary sequences that can be used as connector sequences to link CDR3-J polynucleotides and the designated V gene germline polynucleotides according to the scheme described in FIG. 7.

TABLE 3

Connector sequences with arbitrary sequences

| SEQ ID NO: | Connector sequence |
|---|---|
| 134 | CCGGGATTTTGTGACTCATC |
| 135 | GAGGATCGTATGTTTCGCAC |
| 136 | CTTGTGTGCACTTACCGTAC |
| 137 | TGATGCATCTCCAGTACAGG |
| 138 | CTTCTGTGTGTACCTCGACA |
| 139 | CTTGCAATCCTTTACCGTGC |
| 140 | GCAAGTGTGGAAAATGACCC |
| 141 | GAGTCTAGTCTCACAACCCA |
| 142 | GAAATGTTGAGGACTCCACG |
| 143 | CCTAACAGATGCTACGTGGA |
| 144 | GTAGGTCCACACAGATTCCA |
| 145 | GCCAGTCACAGCAAATACAC |
| 146 | CCGCTACCAGTATGTACCTT |
| 147 | ACTGTGTTCCTTGTCTTCCG |
| 148 | TGAATGCATCTACGGTACCG |
| 149 | GCGCTTATCAATCTTGCTCG |
| 150 | CGGTCAATTCAGTAGCCACT |
| 151 | GGACACATGTACACTAGCCA |

TABLE 3-continued

Connector sequences with arbitrary sequences

| SEQ ID NO: | Connector sequence |
|---|---|
| 152 | TGGGAGCTCTACGAAAATCC |
| 153 | GTTCTCGAGATCGTCACACA |
| 154 | CTTCTGCATTCGATCCTTGC |
| 155 | GCAGAGTTGTGTGATTGGAG |
| 156 | CCCATCAATTCGGAACCATC |
| 157 | ATCGTAACCCAAGTCTGTGG |
| 158 | GGCGAAATGATCCCTGAATG |
| 159 | AGTGCTCAGAACTTTCAGGC |
| 160 | GATCGTTAACTCTTTGGGCG |
| 161 | ACACGAGGATTGCTGTAGAG |
| 162 | TTCTACCACATTGTCTCGGG |
| 163 | GAATGGCTAAACTGTGTCCC |
| 164 | CGGACTGTACGAGAAACTGA |
| 165 | CTTGCGACAAACTACTCCTG |
| 166 | CCGTTTTACTTTGTCGCCAC |
| 167 | TGGATGATATCACTTCGGCG |
| 168 | CCAACCTCTATATGTGCCCA |
| 169 | TGAACAGGTATGCTCCAGAG |
| 170 | TTGTGGATATCGTCTGGTCC |
| 171 | CTGTGGAACTCGACTCTTGT |
| 172 | CTCCAGGATGCACAAATTCG |
| 173 | GGCTCATGACAAAACACAGG |
| 174 | CCGAATCCGAAAACAACACG |
| 175 | AGACCTAACACTGTGATGCG |
| 176 | CCTGGGTGAGCATAAACTTC |
| 177 | GAGTCTTGGACGAACAAAGG |
| 178 | CACGTACCCATCATGTTCTG |
| 179 | CCGTGTTAGTCAAGTGTGTG |
| 180 | CTGGTGGCATAAATGGAACG |
| 181 | TGGATGTGGGTATCAATGGG |
| 182 | TGTGGCTAACGTAGGACAAG |
| 183 | CCCTCGTTGTGAAAATGTGC |
| 184 | TCGTCATAGGTCAGCTTACG |
| 185 | CCTGATGACCTCTATGCCAA |
| 186 | CGGCAAGAATGAATAGGGTG |
| 187 | GTGCTATTGGTGGGAAATGG |
| 188 | GCCATGTTTGCTTACTGACG |
| 189 | CGTTGTGGCATTCATTAGCG |
| 190 | GCGGTAGGATTGGATCTCAT |
| 191 | CCTCGCAAAGCTGTTATGAC |
| 192 | GCCTTCATGTTATTGGACGC |
| 193 | AGCTGTAGTGTTCTTGAGGC |
| 194 | GGTAGTGTTCGTGTGACATG |
| 195 | CGCGGCATATGTTCATATCC |
| 196 | GAGACTGGATCATGCAACAG |
| 197 | CACAACTTCTCTGGACTCCA |
| 198 | CGACCATGATCTGTATGCGT |
| 199 | GGTGTGACTCTTGTTTCCGT |
| 200 | ACGTACATACAAGTCTGGCG |
| 201 | CCTCAAGGATTCACTCGCAA |
| 202 | CTGTATAGGATGTCCACGCA |
| 203 | GCCTGTGATTGGTAAATGCG |
| 204 | CGCACTCGTAGCATCTAGAA |
| 205 | CGATTTGTTGTCCCTAGCTG |
| 206 | CCCACTTCATCTGACTCTGA |
| 207 | CGGCATTGTACAGGTGTTAC |
| 208 | TCTCCTATTTCCCTGAACGG |
| 209 | CTTGTCCACTAAACGCAACG |
| 210 | CGGGTATCACTGGGTAATGA |
| 211 | GGAACAGAGACCAATCCAGT |
| 212 | GTGGGCATCCGAAATTTCAG |
| 213 | CGCGACGACATTACCAATAG |
| 214 | CGTCGGAATATGCTCTCAGA |
| 215 | GATGCAGATCAATGAGTGGC |
| 216 | ACTGCTTACAAGTGTCCACG |
| 217 | ACTGTATGCAAGCTAGTCCC |
| 218 | AGATCTCCCAAAAGTGTCCG |
| 219 | TTCCAGAACCATGTGATCCC |
| 220 | GCCTTGTCTTTCAACCTCTG |
| 221 | GATACGGATCTTCACATGCG |
| 222 | CGCTCATCTAGGTTGGACTA |
| 223 | CGCGTTCAGATTCCAAACAG |
| 224 | GCCTGGTTACACATGCTATC |
| 225 | GCAAAGGTCCTACAGGTTTC |
| 226 | GGCTTTCCATGTCTATGCTC |

TABLE 3-continued

Connector sequences with arbitrary sequences

| SEQ ID NO: | Connector sequence |
|---|---|
| 227 | GCGACATTAGCAGAGTAGGT |
| 228 | CTCGCCATACTATCTGCATG |
| 229 | CTACTGAACACTTGGCAAGC |
| 230 | CTGTTCAATTCCTGTGCGAG |
| 231 | CACTGAGATGGAATTTGGCG |
| 232 | GTCCATCACAACTTCCACTG |
| 233 | GGCTCAGTCTACTTTGCTTC |
| 234 | GTTAGCTTCCGACACAATGG |
| 235 | CCGTGACACACTTTCATCTC |
| 236 | CCGGGATGTCATTATGAGCA |
| 237 | GAGTGTCCTACGAGATCAGA |
| 238 | TAACGTCTCTCTGAGTGTGG |
| 239 | ACCCTAGACAAGAGACACCT |
| 240 | TGCTCAGTACTCTTCATCGC |
| 241 | AGCTCAATCATGGCTATCGG |
| 242 | CTACACATTGCATCCAACCC |
| 243 | ACTTGTCGAATAGCTCAGGC |
| 244 | GTCTACCCTGAGAACCAGTT |
| 245 | CAGCAACAACCTACCTTAGC |
| 246 | CGATTTGTTGGTACGTGTCC |
| 247 | GCCATTTCCTTTGTACCTGC |
| 248 | GGCCAATAGAGAGACCACAA |
| 249 | CGGAGTCACATGGGTAGAAT |
| 250 | CCCAGTACATTTGTCGGTTG |
| 251 | CCCACTAGCTGCTACTCAAA |
| 252 | GGTGTTGCGTCAAAGTAGAC |
| 253 | TACTCCAGCTCTTACTGTGC |
| 254 | GGATGAGCAGTCAACAGTTC |
| 255 | TCAGGATCGATCAGTTGTCC |
| 256 | CCTCTCTTTTGTGCGGAAAC |
| 257 | TGCCTAGGATTTCGAGAACG |
| 258 | GGCATTGTCCTTAACTTCGC |
| 259 | TGCATCTAACTACGATGGGC |
| 260 | CCCTAGTAGCCACACAACAT |
| 261 | GTGCCATGAATCATCGTCTC |
| 262 | CGCTCTGATGAAAGCTCCAT |
| 263 | CCAGCCATAGTGCATATCCT |

TABLE 3-continued

Connector sequences with arbitrary sequences

| SEQ ID NO: | Connector sequence |
|---|---|
| 264 | GAGATTGTCATGTGGTCGAC |
| 265 | CCGCAGTCTAACAGGAAATC |
| 266 | CGCTTCGACTGAACCTTATG |
| 267 | CGATGCGACCAATAGAAGTG |
| 268 | GCCCTTGGTACGACATATTG |
| 269 | CAGTGATTAGGTGACGCAG |
| 270 | GGCATGGAAGAGGTAGTTTC |
| 271 | CCGATCGTATTCTGTGTCCA |
| 272 | CTAAGTCAAGCACATGGGAC |
| 273 | GATCCACACTCAATCTCCTG |
| 274 | CCTTGTCACATGCTGGTATC |
| 275 | CGCGATTGTGGTTAATAGGC |
| 276 | GTAGGCAAAGTTCACCACAC |
| 277 | GCCACGAATCGAACAAGTAC |
| 278 | TTGAGATCTCGATGAGCACG |
| 279 | GGGCCAAGATCTATTCGTCA |
| 280 | GTGGCTATAGGTATGTCCGA |
| 281 | CCACACTTTCTGCATTCGAC |
| 282 | CGGCATCTCAAAGCACATAC |
| 283 | CGTCCACAAATTTACTGCCC |

Example 5. Characterization of Assembled TCR Genes using Next-Generation Sequencing A pool of nucleic acid sequences encoding paired TCRs were prepared using the methods described herein (e.g., Example 1 with some modifications). The reference sequences encoding natively paired TCRs were obtained from publicly available libraries. 553 reference sequences were selected to be demonstrated in this example. In this example, the nucleic acid sequences encoding CDR3-Jα (or CDR3-Jα fragments) and nucleic acid sequences encoding CDR3-Jβ (or CDR3-Jβ fragments) were separately synthesized. Alternatively, the paired CDR3-Jα and CDR3-Jβ can be synthesized together on one fragment.

553 CDR3-Jα fragments and 553 CDR3-Jβ fragments were synthesized and connected (e.g., by ligation, overlapping PCR, etc.) together to generate a pool of paired CDR3-Jα-CDR3-Jβ fragments. To ensure that a CDR3-Jα was ligated to the natively paired CDR3-Jβ, an arbitrary connector sequence was synthesized on each CDR3-Jα and the arbitrary connector sequence was designed such that it can minimize cross-hybridization with other arbitrary connector sequences in the pool of CDR3-Jα fragments. The complementary sequence of the arbitrary connector sequence was synthesized on the natively paired CDR3-Jβ. Next, a pool of TRAV fragments (pre-synthesized according to the reference sequences) were connected to the paired CDR3-Jα-CDR3-Jβ fragments to generate a pool of TRAV-CDR3-Jα-CDR3-Jβ fragments, each comprising a TRAV sequence connected to its cognate CDR3-Jα. Next, TRBC1 sequence was appended downstream of TRAV-CDR3-Jα-CDR3-Jβ fragments to form TRAV-CDR3-Jα-CDR3-Jβ-TRBC1 fragments. These fragments were circularized and re-linearized by cutting immediately upstream of the CDR3-Jβ, forming CDR3-Jβ-TRBC1-TRAV-CDR3-Jα fragments. The TRBC1 and TRAV fragments were designed in a way that an in-frame self-cleaving P2A sequence connects TRBC1 and TRAV. Next, a pool of TRBV fragments (pre-synthesized according to the reference sequences) were connected to the CDR3-Jβ-TRBC1-TRAV-CDR3-Jα fragments to generate TRBV-CDR3-Jβ-TRBC1-TRAV-CDR3-Jα, which were subjected to next-generation sequencing (NGS) to assess abundance of clones and connection accuracy of the clones. Here, each clone in the NGS data refers to a unique sequence. Since 553 reference sequences were used in this example, there were a total of 553 clones in the NGS data. For data analysis described herein, CDR3-Jα sequences were used to represent clones.

Figure 12:
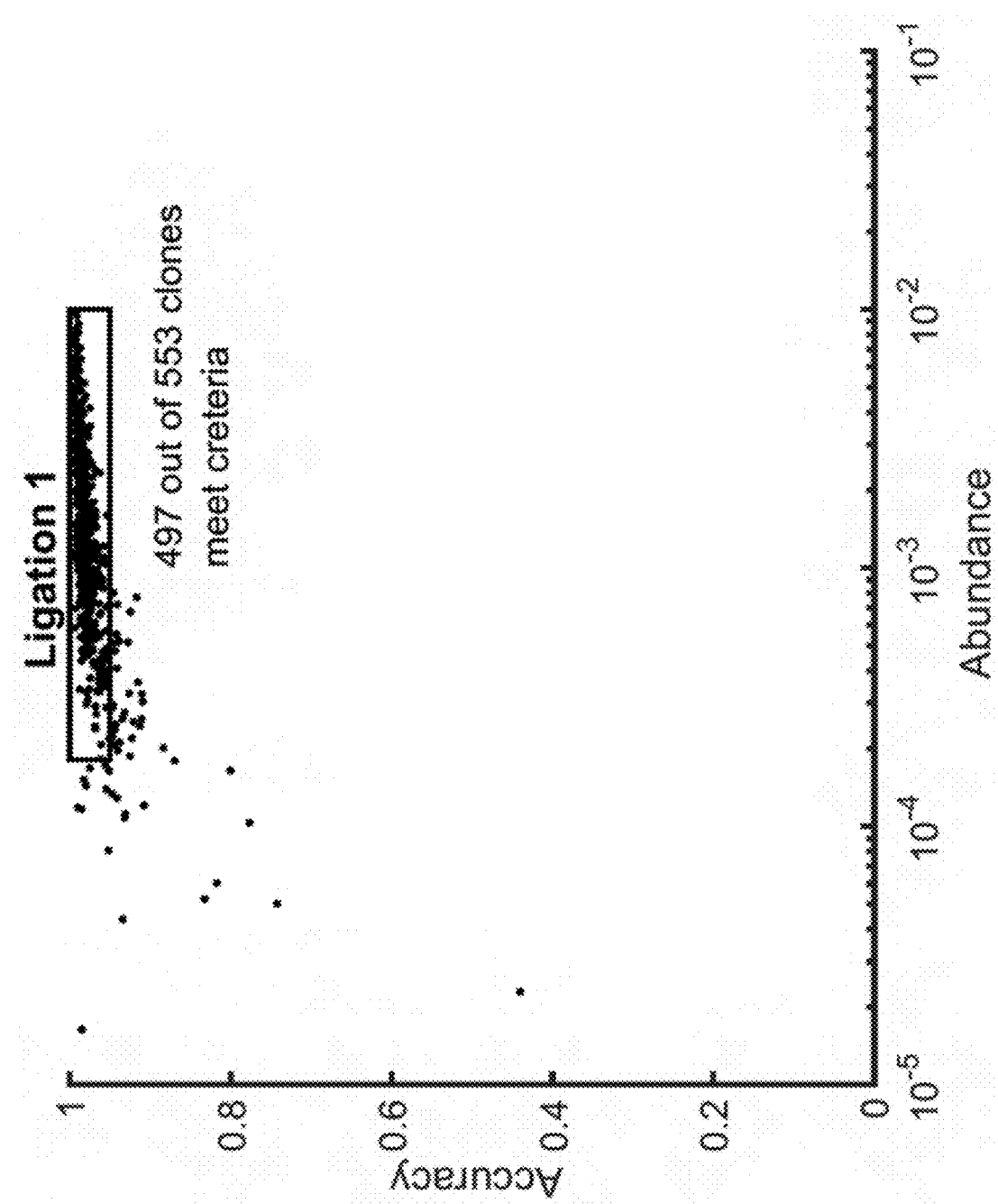
FIG. 12 depicts an example next generation sequencing data assessing the gene assembly methods described herein.

FIG. 12 shows accuracy and abundance of each clone after generating of the paired CDR3-Jα-CDR3-Jβ fragments. Each data point corresponds to a clone of a CDR3-Jα-CDR3-Jβ fragment. Accuracy refers to fraction of CDR3-Jα fragments that are connected to the cognate CDR3-Jβ fragments. For each CDR-Jα, the accuracy can be calculated by the number of correctly connected CDR3-Jβ fragments divided by the total number of connected CDR3-Jβ fragments. Abundance refers to the fraction of each clone in the total pool of clones, which can be calculated by the total number of reads of that clone divided by the total number of reads of all clones. The data show that 497 out of 553 clones have an accuracy higher than 95% and an abundance higher than 0.1/553, as indicated in the box.

Figure 13:
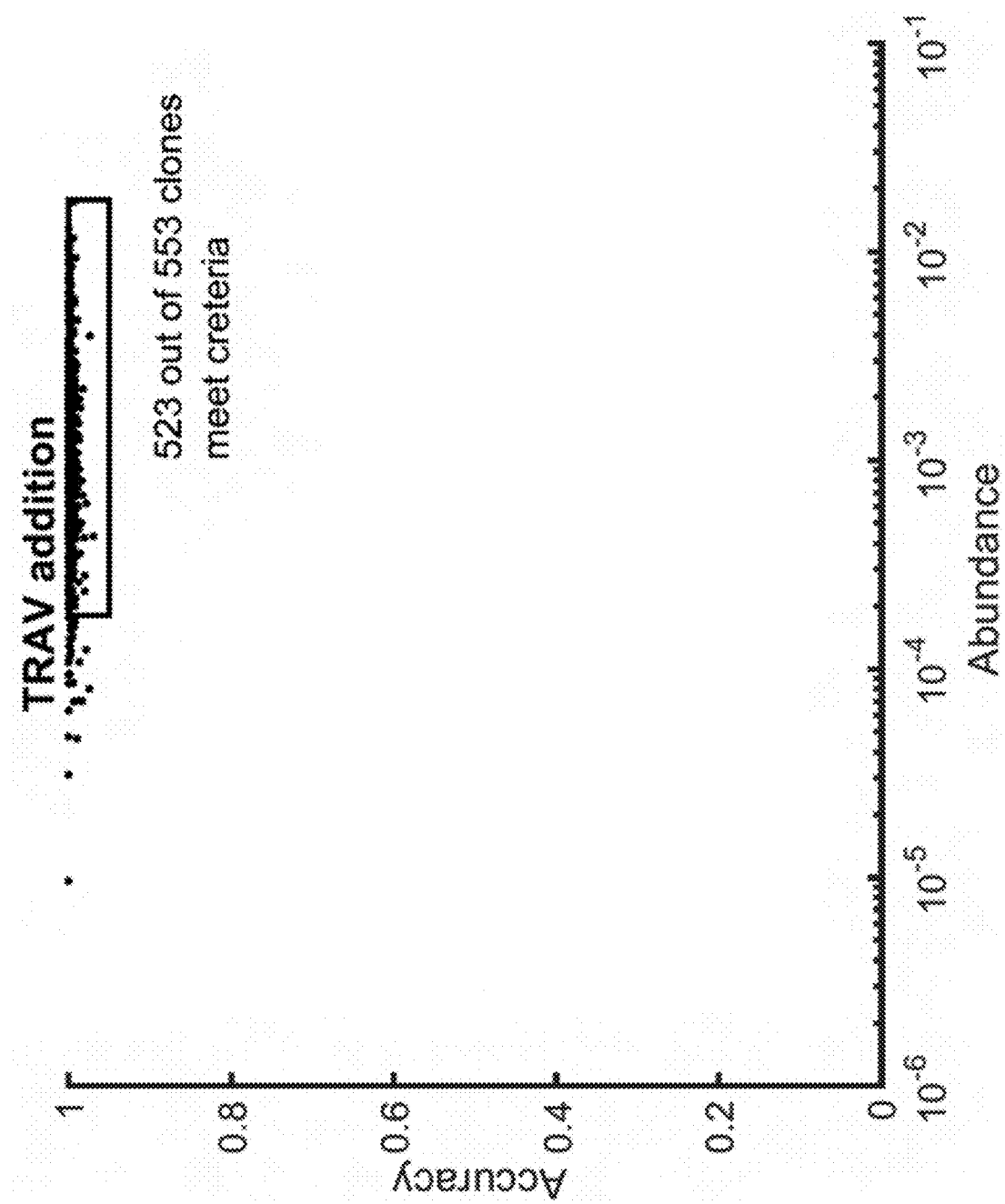
FIG. 13 depicts an example next generation sequencing data assessing the gene assembly methods described herein.

FIG. 13 shows accuracy and abundance of each clone after generating of the TRAV-CDR3-Jα-CDR3-Jβ fragments. Each data point corresponds to a clone of a TRAV-CDR3-Jα-CDR3-Jβ fragment. Accuracy refers to fraction of CDR3-Jα-CDR3-Jβ fragments that are connected to the cognate TRAV fragments. For each CDR3-Jα-CDR3-Jβ, the accuracy can be calculated by the number of correctly connected TRAV fragments divided by the total number of connected TRAV fragments. Abundance refers to the fraction of each clone in the total pool of clones, which can be calculated by the total number of reads of that clone divided by the total number of reads of all clones. The data show that 523 out of 553 clones have an accuracy higher than 95% and an abundance higher than 0.1/553, as indicated in the box.

Figure 14:
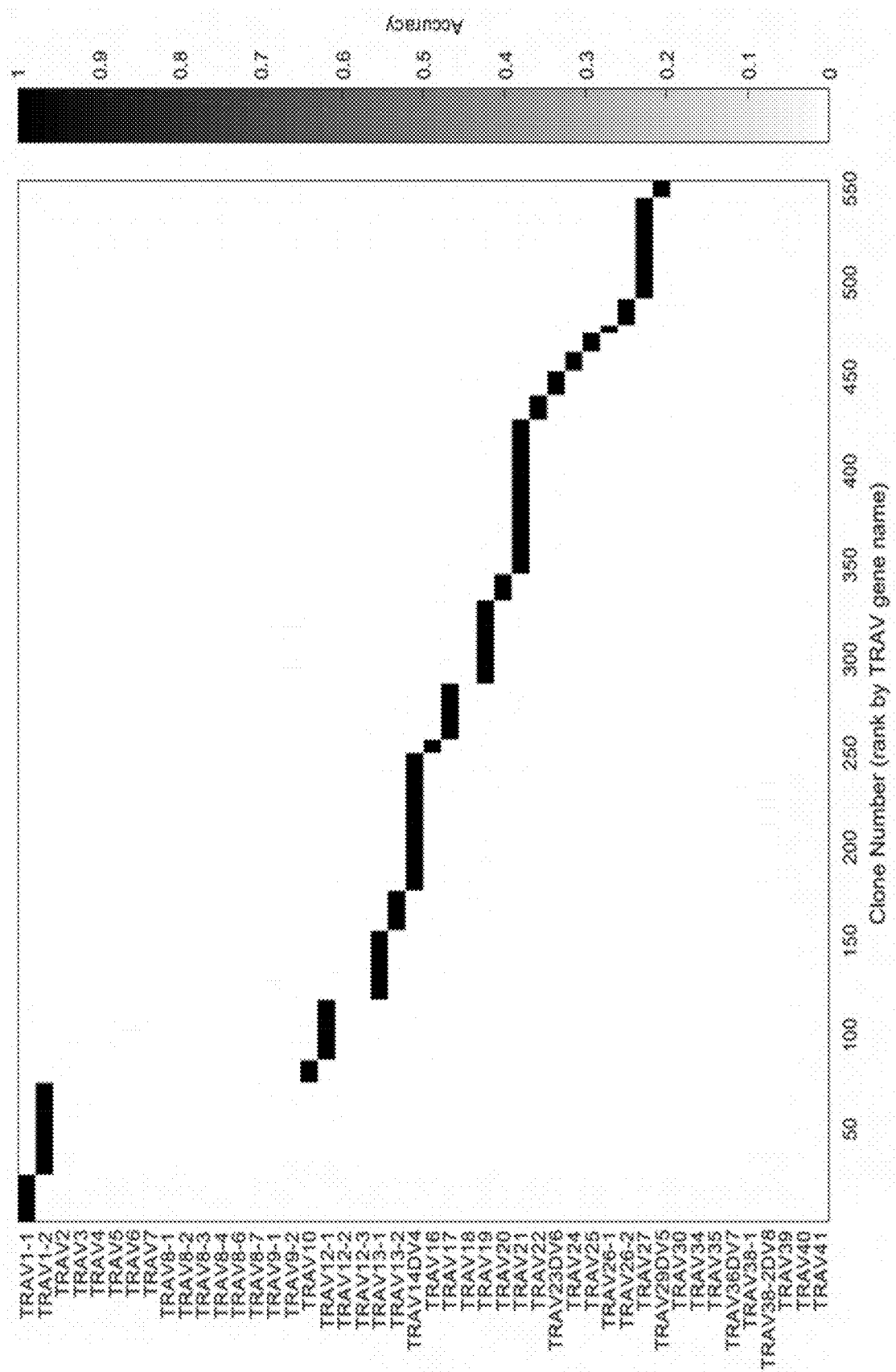
FIG. 14 depicts an example next generation sequencing data assessing the gene assembly methods described herein.

FIG. 14 shows a heatmap mapping each TRAV to each clone in the pool. The clone number is ranked according to its cognate TRAV gene name. The data show for each clone, majority of reads have the correct TRAV sequences, indicating high accuracy when connecting CDR3-Jα-CDR3-Jβ fragments to their cognate TRAV fragments.

Figure 15:
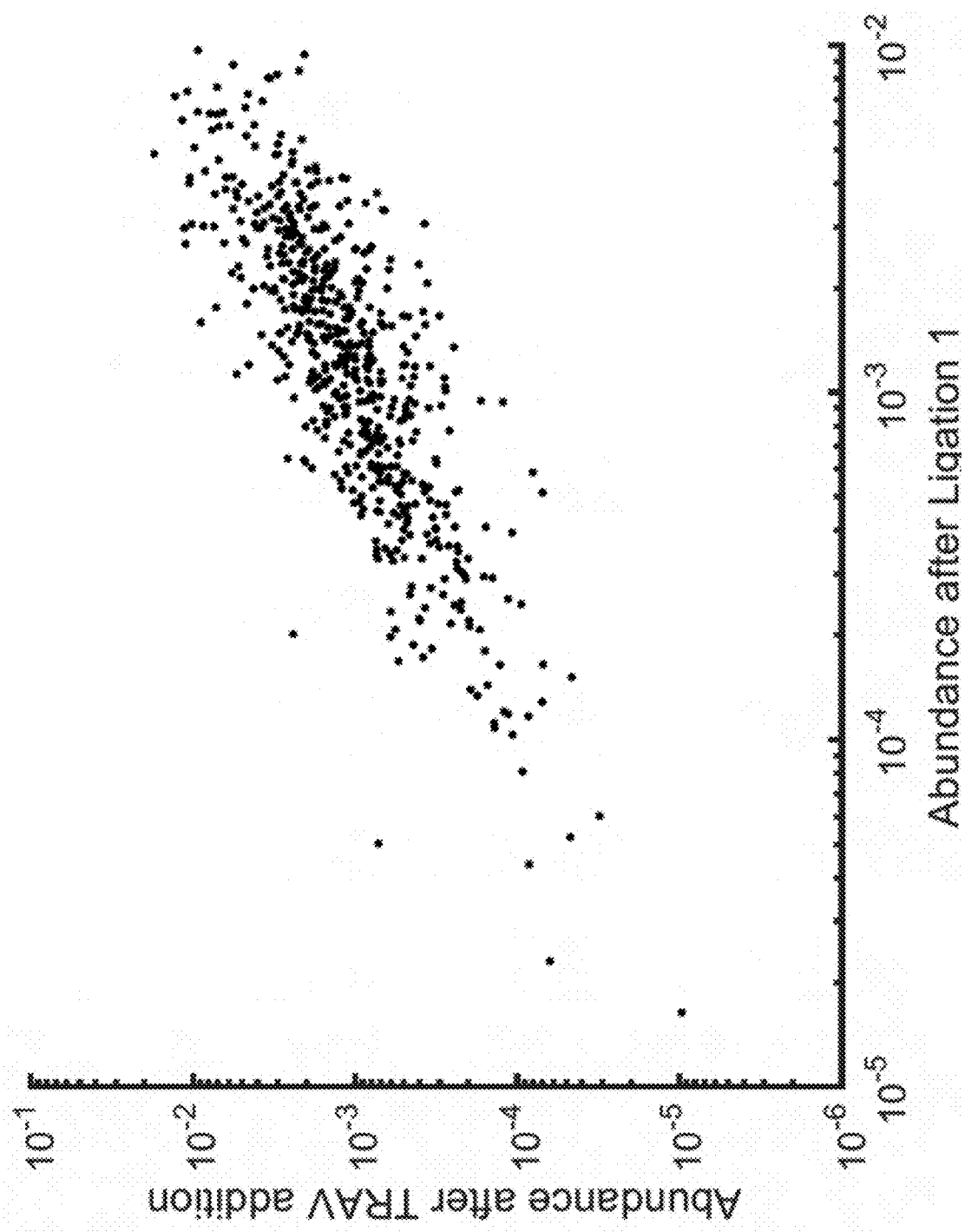
FIG. 15 depicts an example next generation sequencing data assessing the gene assembly methods described herein.

FIG. 15 shows abundance of each clone after generating TRAV-CDR3-Jα-CDR3-Jβ fragments (e.g., TRAV addition in FIG. 15) versus abundance after generating CDR3-Jα-CDR3-Jβ fragments. The data show overall bias is dominated by the bias during the ligation of CDR3-Jα and CDR3-Jβ fragments. This bias may be reduced or avoided by directly synthesizing paired CDR3-Jα-CDR3-Jβ fragments.

Figure 16:
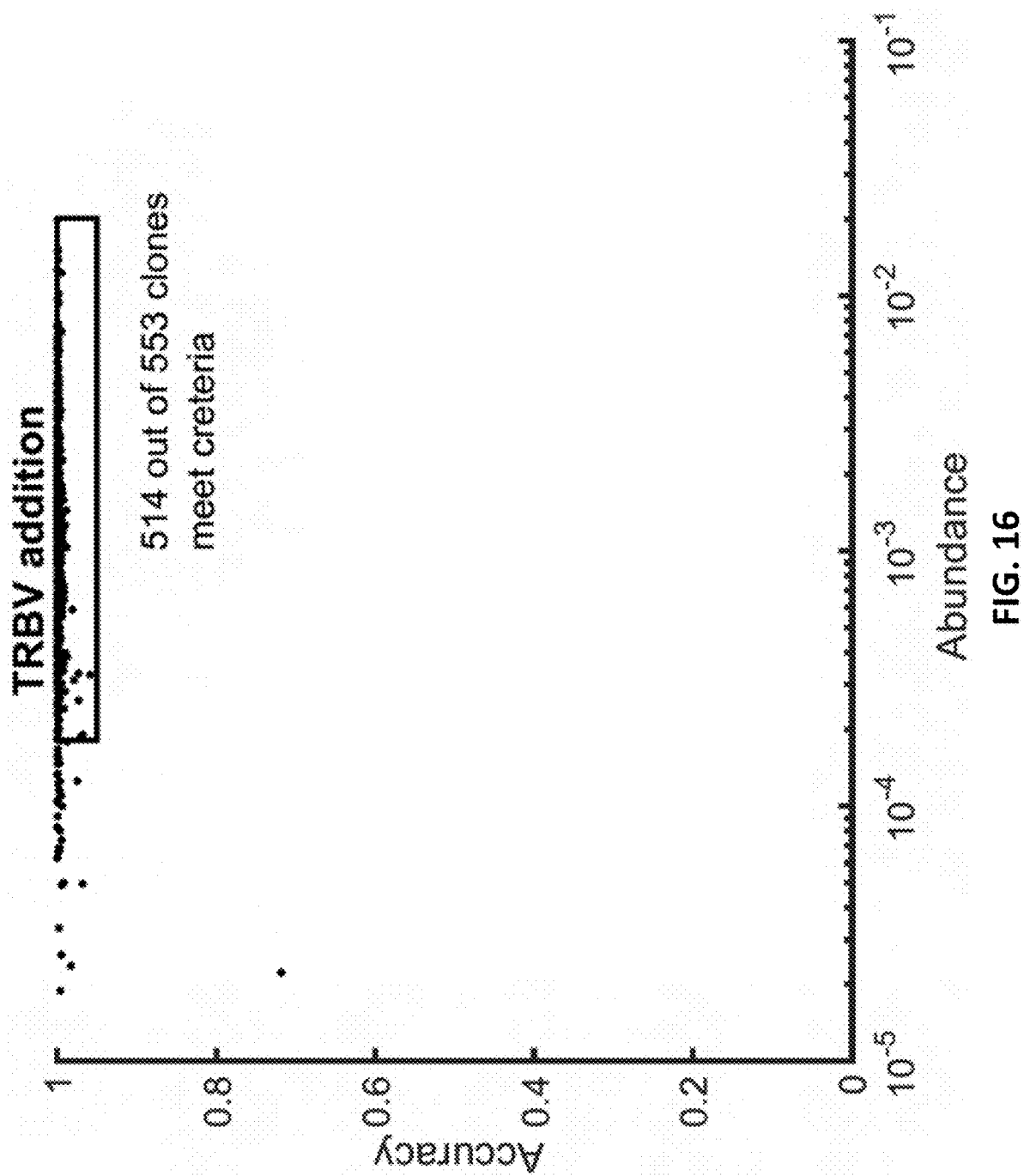
FIG. 16 depicts an example next generation sequencing data assessing the gene assembly methods described herein.

FIG. 16 shows accuracy and abundance of each clone after generating of the TRBV-CDR3-Jβ-TRBC1-TRAV-CDR3-Jα fragments. Each data point corresponds to a clone of a TRBV-CDR3-Jβ-TRBC1-TRAV-CDR3-Jα fragment. Accuracy refers to fraction of CDR3-Jβ-TRBC1-TRAV-CDR3-Jα fragments that are connected to the cognate TRBV fragments. For each CDR3-Jβ-TRBC1-TRAV-CDR3-Jα, the accuracy can be calculated by the number of correctly connected TRBV fragments divided by the total number of connected TRBV fragments. Abundance refers to the fraction of each clone in the total pool of clones, which can be calculated by the total number of reads of that clone divided by the total number of reads of all clones. The data show that 514 out of 553 clones have an accuracy higher than 95% and an abundance higher than 0.1/553, as indicated in the box.

Figure 17:
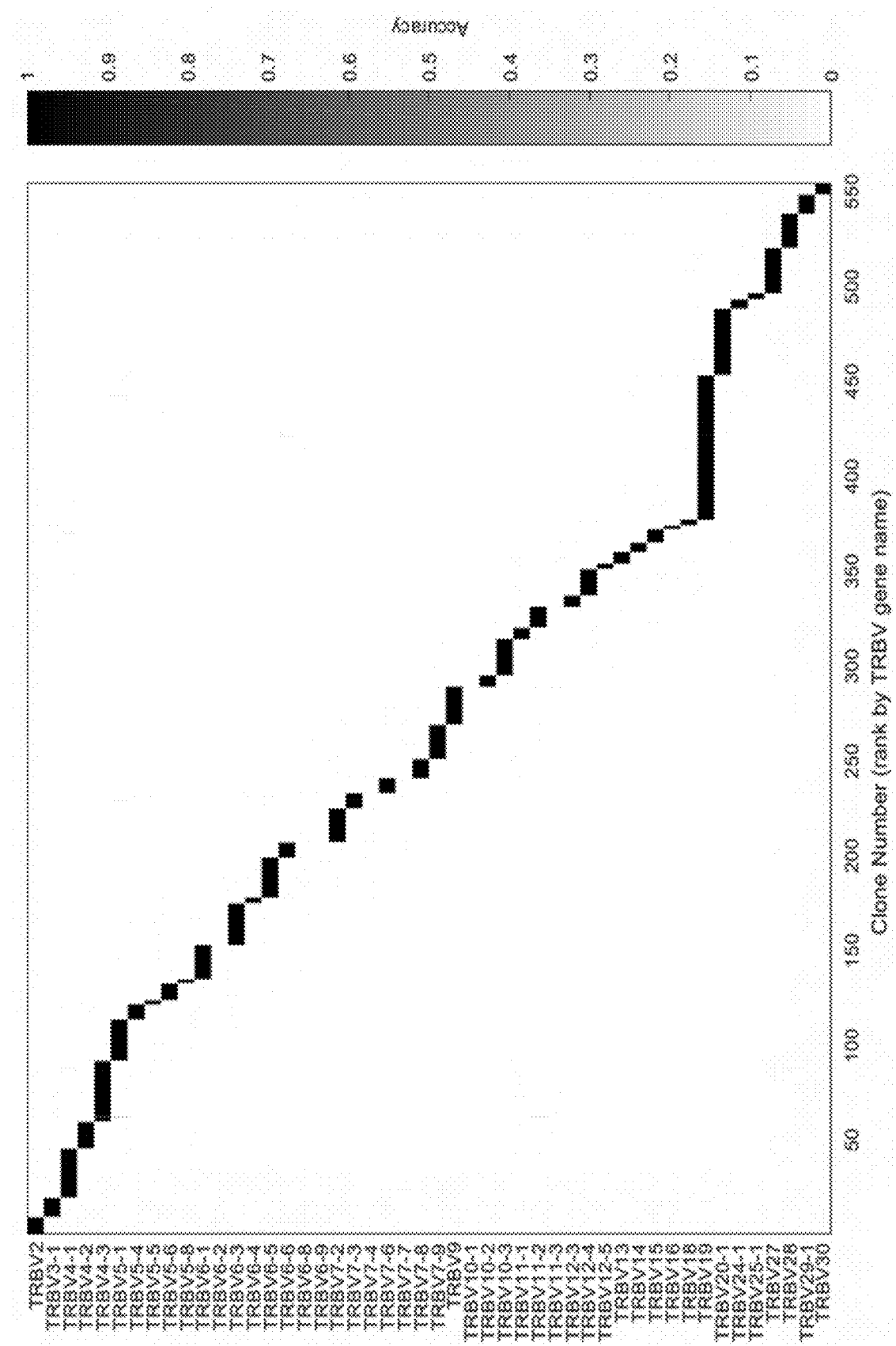
FIG. 17 depicts an example next generation sequencing data assessing the gene assembly methods described herein.

FIG. 17 shows a heatmap mapping each TRBV to each clone in the pool. The clone number is ranked according to its cognate TRBV gene name. The data show for each clone, majority of reads have the correct TRBV sequences, indicating high accuracy when connecting CDR3-Jβ-TRBC1-TRAV-CDR3-Jα fragments to their cognate TRBV fragments.

Figure 18:
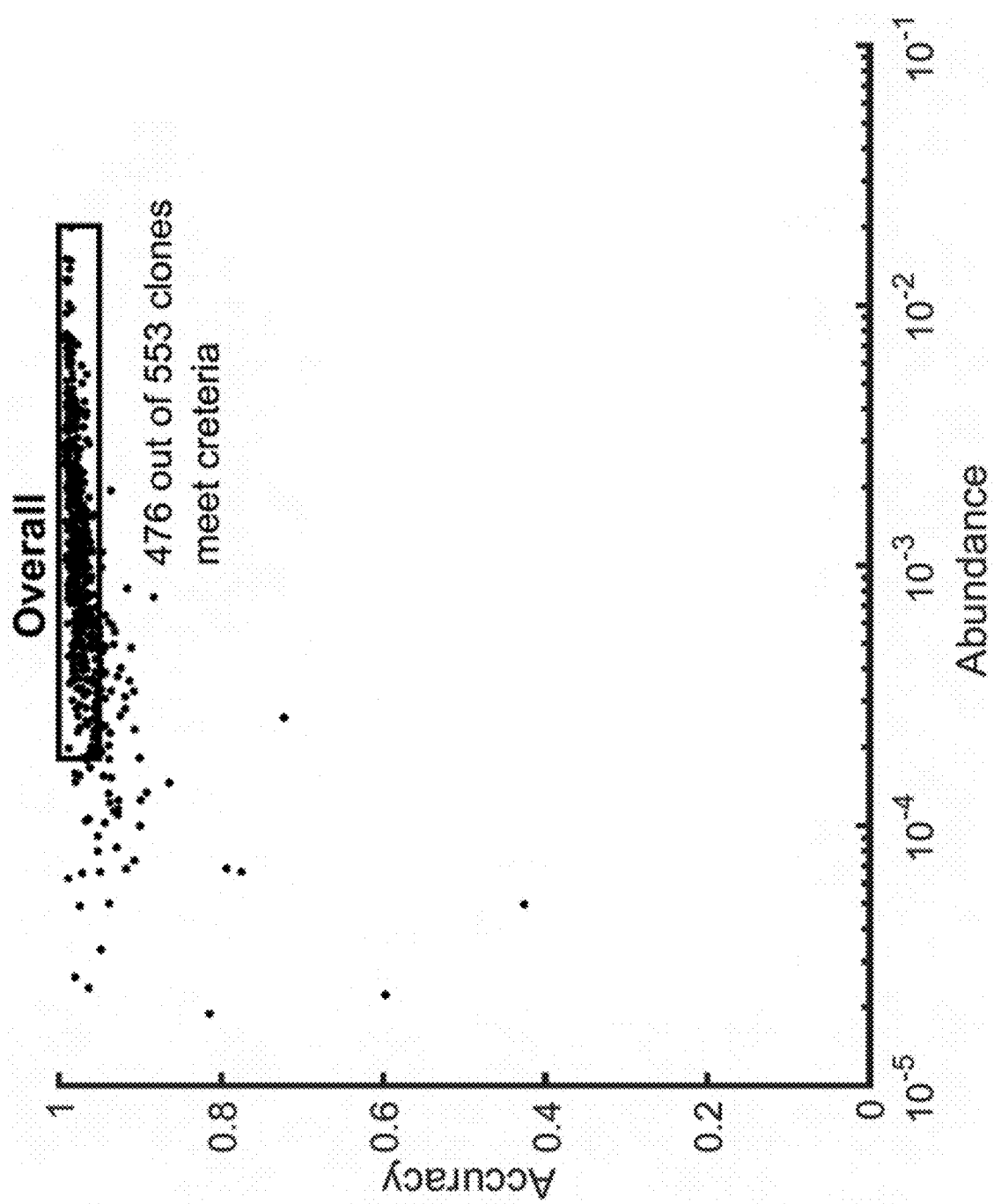
FIG. 18 depicts an example next generation sequencing data assessing the gene assembly methods described herein.

FIG. 18 shows overall accuracy and abundance of each clone after generating of the TRBV-CDR3-Jβ-TRBC1-TRAV-CDR3-Jα fragments. The overall accuracy for each clone was calculated multiplying the accuracy in each step shown in FIGS. 12, 13 and 16. The abundance was calculated by the total number of reads of that clone divided by the total number of reads of all clones.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Embodiment Paragraphs

The present disclosure provides:
[1] A method for generating a nucleic acid molecule encoding a T-cell receptor (TCR) chain or portion thereof, comprising: (a) providing at least one nucleic acid molecule comprising a sequence encoding a CDR3 of a TCR chain; (b) providing a plurality of nucleic acid molecules, each nucleic acid molecule of the plurality comprising a sequence derived from a TCR V gene, wherein the plurality of nucleic acid molecules comprises at least two different sequences derived from at least two different TCR V genes; and (c) contacting the at least one nucleic acid molecule of (a) to the plurality of nucleic acid molecules of (b) in a same compartment, wherein the at least one nucleic acid molecule of (a) is capable of linking to a nucleic acid molecule of the plurality of nucleic acid molecules to generate a third nucleic acid molecule comprising the sequence encoding the CDR3 and a sequence derived from one of the at least two different TCR V genes, thereby generating the nucleic acid molecule encoding the TCR chain or portion thereof.
[2] The method of paragraph [1], wherein the least one nucleic acid molecule comprises a first plurality of nucleic acid molecules, wherein each nucleic acid molecule of the first plurality of nucleic acid molecules comprises a sequence encoding a CDR3 of a TCR chain.
[3] The method of paragraph [1] or [2], wherein the at least one nucleic acid molecule of (a) is capable of specifically linking to a nucleic acid molecule of the plurality of nucleic acid molecules that comprises a sequence derived from any single given TCR V gene of the at least two different TCR V genes.

[4] The method of paragraph [1], wherein the at least one nucleic acid molecule further comprises a J region of the TCR chain.

[5] The method of paragraph [2], wherein each nucleic acid molecule of the first plurality of nucleic acid molecules further comprises a J region of a TCR chain.

[6] The method of any one of paragraphs [1]-[5], wherein the at least two TCR V genes are human TCR V genes or mouse TCR V genes.

[7] The method of any one of paragraphs [1]-[6], wherein the at least two TCR V genes are selected from the group consisting of a human TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, and TRAV41.

[8] The method of any one of paragraphs [1]-[6], wherein the at least two TCR V genes are selected from the group consisting of a human TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, and TRBV30.

[9] The method of any one of paragraphs [1]-[8], wherein each sequence of the plurality of sequences derived from the at least two different TCR V genes comprises a sequence encoding L-PART1, L-PART2, FR1, CDR1, FR2, CDR2, and/or FR3.

[10] The method of any one of paragraphs [1]-[9], wherein the TCR chain is a TCR alpha chain, a TCR beta chain, a TCR gamma chain, or a TCR delta chain.

[11] The method of any one of paragraphs [1]-[10], wherein the at least one nucleic acid molecule further comprises an additional sequence encoding an additional CDR3 of an additional TCR chain.

[12] The method of paragraph [11], wherein the at least one nucleic acid molecule comprises an additional J region of the additional TCR chain.

[13] The method of paragraph [11] or [12], wherein the sequence encoding the CDR3 and the additional sequence encoding the additional CDR3 are separated by at most 100 nucleotides.

[14] The method of any one of paragraphs [11]-[13], wherein the TCR chain and the additional TCR chain are a cognate pair of TCR chains.

[15] The method of any one of paragraphs [1]-[14], wherein the at least one nucleic acid molecule comprises a connector sequence, which connector sequence is capable of linking the at least one nucleic acid molecule to the nucleic acid molecule of the plurality of nucleic acid molecules to generate the third nucleic acid molecule.

[16] The method of paragraph [15], wherein the at least one nucleic acid molecule and the nucleic acid molecule of the plurality of nucleic acid molecules encodes a functional TCR chain or portion thereof.

[17] The method of paragraph [15] or [16], wherein the nucleic acid molecule of the plurality of nucleic acid molecules comprises an anti-connector sequence, which anti-connector sequence is complementary to the connector sequence of the at least one nucleic acid molecule of (a).

[18] The method of any one of paragraphs [1]-[17], further comprising linking the at least one nucleic acid molecule of (a) and the nucleic acid molecule of the plurality of nucleic acid molecules of (b).

[19] The method of paragraph [18], wherein linking comprises hybridizing the at least one nucleic acid molecule of (a) and the nucleic acid molecule of the plurality of nucleic acid molecules of (b).

[20] The method of paragraph [19], wherein hybridizing comprises hybridizing the connector sequence of the at least one nucleic acid molecule of (a) with the anti-connector sequence of the nucleic acid molecule of the plurality of nucleic acid molecules of (b).

[21] The method of any one of paragraphs [18]-[20], further comprising (i) extending a free 3' end of the nucleic acid molecule of the plurality of nucleic acid molecules using the at least one nucleic acid molecule of (a) as a template, and/or (ii) extending a free 3' end of the at least one nucleic acid molecule of (a) using the nucleic acid molecule of the plurality of nucleic acid molecules as a template, to generate the third nucleic acid molecule.

[22] The method of any one of paragraphs [1]-[21], further comprising ligating the at least one nucleic acid molecule of (a) and the nucleic acid molecule of the plurality of nucleic acid molecules (b).

[23] The method of any one of paragraphs [1]-[22], further comprising contacting the third nucleic acid molecule with a restriction enzyme to generate a sticky end.

[24] The method of any one of paragraphs [1]-[23], further comprising contacting the third nucleic acid molecule with an additional nucleic acid molecule.

[25] The method of paragraph [24], wherein the additional nucleic acid molecule encodes a constant region or portion thereof of a TCR chain.

[26] The method of paragraph [24] or [25], further comprising ligating the third nucleic acid molecule and the additional nucleic acid molecule.

[27] The method of any one of paragraphs [1]-[26], wherein a plurality of nucleic acid molecules, each encoding a different TCR chain or portion thereof, are generated in the same compartment.

[28] The method of paragraph [27], wherein at least five different nucleic acid molecules of the plurality of nucleic acid molecules are generated in the same compartment.

[29] The method of any one of paragraphs [1]-[26], wherein at least ten different nucleic acid molecules of the plurality of nucleic acid molecules are generated in the same compartment.

[30] The method of any one of paragraphs [1]-[29], wherein the same compartment is a well, a tube, or a droplet.

[31] The method of any one of paragraphs [1]-[30], wherein the at least one nucleic acid molecule comprises a unique barcode.

[32] The method of paragraph [31], wherein the unique barcode is a primer binding site.

[33] The method of any one of paragraphs [15]-[30], wherein the connector sequence comprises a unique barcode.

[34] The method of paragraph [33], wherein the unique barcode is a primer binding site.

[35] A composition comprising
(a) a plurality of nucleic acid molecules, wherein each nucleic acid molecule of the plurality of nucleic acid molecules comprises a sequence derived from a T-cell receptor (TCR) V gene and does not comprise a CDR3 sequence, wherein a first nucleic acid molecule of the plurality comprises a first anti-connector sequence and a second nucleic acid molecule of the plurality comprises a second anti-connector sequence, wherein the first anti-connector sequence is different from the second anti-connector sequence, and wherein the sequence derived from a TCR V gene of the first nucleic acid molecule and the second nucleic acid molecule are derived from a different TCR V gene; and
(b) at least one nucleic acid molecule comprising a sequence encoding a CDR3 of a TCR chain, wherein the at least one nucleic acid molecule further comprises a first connector sequence complementary to the first anti-connector sequence.

[36] The composition of paragraph [35], wherein the composition is a liquid composition.

[37] The composition of paragraph [35] or [36], wherein the plurality of nucleic acid molecules of (a) and the at least one nucleic acid molecule of (b) are in a same compartment.

[38] The composition of any one of paragraphs [35]-[37], wherein the sequence derived from the TCR V gene comprises at least ten nucleotides of the TCR V gene.

[39] The composition of any one of paragraphs [35]-[38], wherein the TCR V gene is a TRAV gene, a TRBV gene, a TRGV gene, or a TRDV gene.

[40] The composition of any one of paragraphs [35]-[39], wherein the sequence derived from the TCR V gene comprises a sequence encoding L-PART1, L-PART2, FR1, CDR1, FR2, CDR2, and/or FR3.

[41] The composition of any one of paragraphs [35]-[40], wherein the at least one nucleic acid molecule further comprises a J region of the TCR chain.

[42] The composition of any one of paragraphs [35]-[41], wherein the at least one nucleic acid molecule further comprises an additional sequence encoding an additional CDR3 of an additional TCR chain.

[43] The composition of paragraph [42], wherein the at least one nucleic acid molecule further comprises an additional J region of the additional TCR chain.

[44] The composition of paragraph [42] or [43], wherein the sequence encoding the CDR3 and the additional sequence encoding the CDR3 are separated by at most 100 nucleotides.

[45] The composition of any one of paragraphs [42]-[44], wherein the TCR chain and the additional TCR chain are a cognate pair of TCR chains.

[46] The composition of any one of paragraphs [35]-[45], wherein the at least one nucleic acid molecule of (b) comprises a first plurality of nucleic acid molecules, and wherein each nucleic acid molecule of the first plurality of nucleic acid molecules comprises a sequence encoding a CDR3 of a TCR chain.

[47] The composition of paragraph [46], wherein each nucleic acid molecule of the first plurality of nucleic acid molecules encodes a different CDR3 of a different TCR chain.

[48] The composition of paragraph [46] or [47], wherein each nucleic acid molecule of the first plurality of nucleic acid molecules comprises a different connector sequence, which different connector sequence is capable of specifically linking to a nucleic acid molecule of the plurality of nucleic acid molecules that comprises a sequence derived from any single given TCR V gene.

[49] The composition of any one of paragraphs [35]-[48], wherein the first anti-connector sequence or the second anti-connector sequence comprises a TCR V gene sequence.

[50] The composition of paragraph [49], wherein the TCR V gene sequence comprises at least three nucleotides of the TCR V gene adjacent to a sequence encoding a CDR3 in a rearranged gene.

[51] The composition of any one of paragraphs [35]-[50], wherein the first anti-connector sequence or the second anti-connector sequence comprises a pre-determined sequence.

[52] The composition of any one of paragraphs [35]-[51], wherein the first connector sequence hybridizes to the first anti-connector sequence.

[53] The composition of any one of paragraphs [35]-[52], wherein the at least one nucleic acid molecule of (b) comprises a unique barcode.

[54] The composition of paragraph [53], wherein the unique barcode is a primer binding site.

[55] The composition of any one of paragraphs [35]-[52], wherein the first connector sequence of the at least one nucleic acid molecule comprises a unique barcode.

[56] The composition of paragraph [55], wherein the unique barcode is a primer binding site.

[57] A method for generating a plurality of nucleic acid molecules, comprising: (a) providing a first plurality of nucleic acid molecules, wherein a nucleic acid molecule of the first plurality of nucleic acid molecules comprises a sequence encoding a first CDR3 of a first T-cell receptor (TCR) chain and a second CDR3 of a second TCR chain, wherein the first CDR3 and the second CDR3 are from a cognate pair of TCR chains; (b) providing a second plurality of nucleic acid molecules, wherein a nucleic acid molecule of the second plurality of nucleic acid molecules comprises a sequence derived from a TCR V gene, wherein the nucleic acid molecule does not comprise a sequence encoding a constant domain; and (c) contacting the first plurality of nucleic acid molecules and the second plurality of nucleic acid molecules, wherein the nucleic acid molecule of the first plurality of nucleic acid molecules links with the nucleic acid molecule of the second plurality of nucleic acid molecules to form a nucleic acid molecule comprising the sequence encoding the first CDR3 and the second CDR3 and the sequence derived from the TCR V gene, wherein the sequence encoding the first CDR3 and the second CDR3 and the TCR V gene are derived from the cognate pair of TCR chains.

[58] The method of paragraph [57], wherein each nucleic acid molecule of the first plurality of nucleic acid molecules comprises a sequence encoding a different first CDR3 of a first TCR chain and/or a different CDR3 of a second TCR chain.

[59] The method of paragraph [57] or [58], wherein each nucleic acid molecule of the second plurality of nucleic acid molecules comprises a sequence derived from a different TCR V gene.

[60] The method of any one of paragraphs [57]-[59], wherein the first plurality of nucleic acid molecules and the second plurality of nucleic acid molecules are contacted in a same compartment.

[61] The method of any one of paragraphs [57]-[60], wherein the nucleic acid molecule of the first plurality of nucleic acid molecules further comprises a connector sequence, wherein the connector sequence links the nucleic acid molecule of the first plurality of nucleic acid molecules and the nucleic acid molecule of the second plurality of nucleic acid molecules.

[62] The method of paragraph [61], wherein the nucleic acid molecule of the second plurality of nucleic acid molecules further comprises an anti-connector sequence, which anti-connector sequence is complementary to the connector sequence.

[63] The method of paragraph [62], wherein the connector sequence hybridizes to the anti-connector sequence to link the nucleic acid molecule of the first plurality of nucleic acid molecules and the nucleic acid molecule of the second plurality of nucleic acid molecules.

[64] The method of any one of paragraphs [58]-[63], wherein the connector sequence is codon-diversified such that the connector sequence of the nucleic acid molecule of the first plurality of nucleic acid molecules is different from other connector sequences of other nucleic acid molecules of the first plurality of nucleic acid molecules.

[65] The method of any one of paragraphs [57]-[64], wherein the nucleic acid molecule of the first plurality of nucleic acid molecules further comprises a first J region of the first TCR chain and/or a second J region of the second TCR chain.

[66] The method of any one of paragraphs [57]-[65], wherein (i) the first TCR chain is a TCR alpha chain and the second TCR chain is a TCR beta chain or (ii) the first TCR chain is a TCR gamma chain and the second TCR chain is a TCR delta chain.

[67] The method of any one of paragraphs [57]-[66], wherein the TCR V gene is a TRAV gene, a TRBV gene, a TRGV gene, or a TRDV gene.

[68] The method of any one of paragraphs [57]-[67], wherein the nucleic acid molecule of the second plurality of nucleic acid molecules is a double-stranded nucleic acid molecule.

[69] The method of any one of paragraphs [57]-[68], wherein the nucleic acid molecule of the second plurality of nucleic acid molecules further comprises a sequence encoding a portion of a self-cleaving peptide.

[70] The method of any one of paragraphs [62]-[69], wherein the anti-connector sequence is an overhang of the nucleic acid molecule of the second plurality of nucleic acid molecules.

[71] The method of any one of paragraphs [62]-[70], wherein the connector sequence or the anti-connector sequence is at least three nucleotides in length.

[72] The method of any one of paragraphs [63]-[71], further comprising (i) extending a 3' end of the nucleic acid molecule of the first plurality of nucleic acid molecules hybridized thereto with the nucleic acid molecule of the second plurality of nucleic acid molecules and/or (ii) extending a 3' end of the nucleic acid molecule of the second plurality of nucleic acid molecules hybridized thereto with the nucleic acid molecule of the first plurality of nucleic acid molecules.

[73] The method of any one of paragraphs [57]-[72], further comprising ligating the nucleic acid molecule of the first plurality of nucleic acid molecules with the nucleic acid molecule of the second plurality of nucleic acid molecule.

[74] The method of any one of paragraphs [57]-[73], further comprising contacting the nucleic acid molecule comprising the sequence encoding the first CDR3 and the second CDR3 and the sequence derived from the TCR V gene with a restriction enzyme to generate a sticky end.

[75] The method of any one of paragraphs [57]-[74], contacting the nucleic acid molecule comprising the sequence encoding the first CDR3 and the second CDR3 and the sequence derived from the TCR V gene with an additional nucleic acid molecule comprising a sequence encoding a constant region or portion thereof.

[76] The method of paragraph [74] or [75], further comprising ligating the nucleic acid molecule comprising the sequence encoding the first CDR3 and the second CDR3 and the sequence derived from the TCR V gene with the additional nucleic acid molecule through the sticky end.

[77] The method of any one of paragraphs [57]-[76], wherein the sequence encoding the first CDR3 and the second encoding the second CDR3 are separated by at most 100 nucleotides.

[78] The method of any one of paragraphs [57]-[77], wherein the sequence derived from the TCR V gene comprises a sequence encoding FR1, CDR1, FR2, CDR2, and FR3.

[79] The method of any one of paragraphs [57]-[77], wherein the sequence derived from the TCR V gene comprises a sequence encoding L-PART1, L-PART2, FR1, CDR1, FR2, CDR2, and FR3.

[80] A composition comprising: (a) a first plurality of nucleic acid molecules, wherein each nucleic acid molecule of the first plurality of nucleic acid molecules comprises a sequence encoding a first CDR3 of a first T-cell receptor (TCR) chain and a second CDR3 of a second TCR chain, wherein the first CDR3 and the second CDR3 are from a cognate pair of TCR chains; and (b) a second plurality of nucleic acid molecules, wherein each nucleic acid molecule of the second plurality of nucleic acid molecules comprises a sequence derived from a TCR V gene, and wherein each nucleic acid molecule of the second plurality of nucleic acid molecules does not comprise a sequence encoding the first CDR3 and the second CDR3;

wherein (i) each nucleic acid molecule of the first plurality of nucleic acid molecules comprises a sequence encoding a different first CDR3 and/or second CDR3, and/or (ii) each nucleic acid molecule of the second plurality of nucleic acid molecules comprises a sequence derived from a different TCR V gene.

[81] The composition of paragraph [80], wherein each nucleic acid molecule of the first plurality of nucleic acid molecules further comprises a connector sequence, wherein a given connector sequence is usable to link a given nucleic acid molecule of the first plurality of nucleic acid molecules and a given nucleic acid molecule of the second plurality of nucleic acid molecules.

[82] The composition of paragraph [80] or [81], wherein each nucleic acid molecule of the second plurality of nucleic acid molecules further comprises an anti-connector sequence, which anti-connector sequence is complementary to the connector sequence.
- [83] The composition of paragraph [81] or [82], wherein the connector sequence is codon-diversified such that the given connector sequence of the given nucleic acid molecule of the first plurality of nucleic acid molecules is different from other connector sequences of other nucleic acid molecules of the first plurality of nucleic acid molecules.
- [84] The composition of any one of paragraphs [81]-[83], wherein the connector sequence encodes an amino acid sequence.
- [85] The composition of paragraph [84], wherein the connector sequence is in frame with the sequence encoding the first CDR3 of the first TCR chain and the second CDR3 of the second TCR chain.
- [86] The composition of any one of paragraphs [81]-[85], wherein the connector sequence comprises at least three nucleotides.
- [87] The composition of paragraph [86], wherein the connector sequence comprises at least three nucleotides of the TCR V gene adjacent to a sequence encoding the first CDR3 of the first TCR chain or the second CDR3 of the second TCR chain in a rearranged gene.
- [88] The composition of any one of paragraphs [84]-[87], wherein a given amino acid sequence encoded by the given connector sequence is the same or substantially the same as at least one other amino acid sequence encoded by at least one other connector sequence.
- [89] The composition of any one of paragraphs [84]-[87], wherein a given amino acid sequence encoded by the given connector sequence is different from other amino acid sequences encoded by other connector sequences.
- [90] The composition of any one of paragraphs [80]-[89], wherein each nucleic acid molecule of the first plurality of nucleic acid molecules further comprises a first J region of the first TCR chain and/or a second J region of the second TCR chain.
- [91] The composition of any one of paragraphs [80]-[90], wherein the composition is a liquid composition.
- [92] The composition of any one of paragraphs [80]-[91], wherein the first plurality of nucleic acid molecules and the second plurality of nucleic acid molecules are within a same compartment.
- [93] The composition of any one of paragraphs [81]-[92], wherein the given nucleic acid molecule of the first plurality of nucleic acid molecules is linked to the given nucleic acid molecule of the second plurality of nucleic acid molecules through the given connector sequence.
- [94] The composition of paragraph [93], wherein the given nucleic acid molecule of the first plurality of nucleic acid molecules hybridizes to the given nucleic acid molecule of the second plurality of nucleic acid molecules through the given connector sequence hybridized to a given anti-connector sequence.
- [95] The composition of any one of paragraphs [80]-[94], wherein the sequence encoding the first CDR3 and the sequence encoding the second CDR3 are separated by at most 100 nucleotides.
- [96] The composition of any one of paragraphs [80]-[95], wherein the sequence derived from the TCR V gene comprises a sequence encoding FR1, CDR1, FR2, CDR2, and FR3.
- [97] The composition of any one of paragraphs [80]-[95], wherein the sequence derived from the TCR V gene comprises a sequence encoding L-PART1, L-PART2, FR1, CDR1, FR2, CDR2, and FR3.
- [98] The composition of any one of paragraphs [80]-[97], wherein each nucleic acid molecule of the first plurality of nucleic acid molecules or the second plurality of molecules is chemically synthesized.
- [99] The composition of any one of paragraphs [80]-[98], wherein each nucleic acid molecule of the first plurality of nucleic acid molecules is at most about 250 nucleotides long.
- [100] A composition comprising a plurality of nucleic acid molecules, each nucleic acid molecule of the plurality of nucleic acid molecules comprising a sequence derived from a T-cell receptor (TCR) V gene, wherein the plurality of nucleic acid molecules comprises a first nucleic acid molecule having a first connector sequence and a second nucleic acid molecule having a second connector sequence, wherein the first connector sequence is different from the second connector sequence.
- [101] The composition of paragraph [100], each nucleic acid molecule of the plurality of nucleic acid molecules comprises a sequence derived from a different TCR V gene.
- [102] The composition of paragraph [100] or [101], each nucleic acid molecule of the plurality of nucleic acid molecules comprises a different connector sequence.
- [103] The composition of any one of paragraphs [100]-[102], wherein each nucleic acid molecule of the plurality of nucleic acid molecules does not comprise a sequence encoding a CDR3 of a TCR chain.
- [104] The composition of any one of paragraphs [100]-[103], wherein each nucleic acid molecule of the plurality of nucleic acid molecules does not comprise a sequence encoding a constant domain of a TCR chain.
- [105] The composition of any one of paragraphs [100]-[104], wherein the sequence derived from the TCR V gene comprises at least ten nucleotides of the TCR V gene.
- [106] The composition of any one of paragraphs [100]-[105], wherein the TCR V gene is a TRAV gene, a TRBV gene, a TRGV gene, or a TRDV gene.
- [107] A composition comprising a plurality of nucleic acid molecules, each nucleic acid molecule of the plurality of nucleic acid molecules encoding a CDR3 of a T-cell receptor (TCR) chain, wherein a first nucleic acid molecule of the plurality comprises a first connector sequence and a second nucleic acid molecule of the plurality comprises a second connector sequence, wherein the first connector sequence is different from the second connector sequence.
- [108] The composition of paragraph [107], wherein each nucleic acid molecule of the plurality of nucleic acid molecules further comprises a J region of a TCR chain.
- [109] The composition of paragraph [107], wherein each nucleic acid molecule of the plurality of nucleic acid molecules encodes a first CDR3 of a first TCR chain and a second CDR3 of a second TCR chain.
- [110] The composition of paragraph [109], wherein each nucleic acid molecule of the plurality of nucleic acid molecules further comprises a first J region of a first TCR chain and a second J region of a second TCR chain.
- [111] The composition of any one of paragraphs [107]-[110], wherein each nucleic acid molecule of the plurality of nucleic acid molecules encodes a different CDR3 of a different TCR chain.

[112] The composition of any one of paragraphs [107]-[111], wherein each nucleic acid molecule of the plurality of nucleic acid molecules comprises a different connector sequence.

[113] The composition of any one of paragraphs [107]-[112], wherein each nucleic acid molecule of the plurality of nucleic acid molecules does not comprise greater than 200 nucleotides of a TCR V gene.

[114] The composition of any one of paragraphs [107]-[113], wherein each nucleic acid molecule of the plurality of nucleic acid molecules does not comprise a sequence encoding a constant domain of a TCR chain.

[115] The composition of any one of paragraphs [100]-[114], wherein the first connector sequence or the second connector sequence comprises a sequence derived from a TCR V gene.

[116] The composition of paragraph [115], wherein the sequence derived from the TCR V gene comprises at least three nucleotides of the TCR V gene adjacent to a sequence encoding a CDR3 in a rearranged gene.

[117] The composition of any one of paragraphs [100]-[116], wherein the first connector sequence or the second connector sequence comprises a pre-determined sequence.

[118] The composition of any one of paragraphs [107]-[114], wherein the first connector sequence or the second connector sequence comprises a sequence complementary to a TCR V gene sequence.

[119] The composition of any one of paragraphs [107]-[114] and [118], wherein the composition further comprises a second plurality of nucleic acid molecules, each nucleic acid molecule of the second plurality of nucleic acid molecules comprising a sequence derived from a TCR V gene.

[120] The composition of paragraph [119], wherein a first nucleic acid molecule of the second plurality comprises a first anti-connector sequence, which first anti-connector sequence is complementary to the first connector sequence.

[121] The composition of paragraph [119] or [120], wherein a second nucleic acid molecule of the second plurality comprises a second anti-connector sequence, which second anti-connector sequence is complementary to the second connector sequence.

[122] The composition of paragraph [120] or [121], wherein the first anti-connector sequence of the first nucleic acid molecule of the second plurality is linked to the first connector sequence of the first nucleic acid molecule of the first plurality.

[123] The composition of paragraph [121] or [122], wherein the second anti-connector sequence of the second nucleic acid molecule of the second plurality is linked to the second connector sequence of the second nucleic acid molecule of the first plurality.

[124] A composition comprising a plurality of nucleic acid molecules, each comprising a sequence encoding at least ten amino acids of a T-cell receptor (TCR) chain, wherein a first nucleic acid molecule of the plurality comprises a first connector sequence and a second nucleic acid molecule of the plurality comprises a second connector sequence, wherein the first connector sequence is different from the second connector sequence, wherein the first connector sequence or the second connector sequence encodes a portion of a TCR chain and wherein the first connector sequence or the second connector sequence is in frame with the sequence encoding at least ten amino acids of a TCR chain.

[125] The composition of paragraph [124], wherein the first connector sequence or the second connector sequence comprises at least four contiguous nucleotides of a TCR chain gene and is in frame with the sequence encoding at least ten amino acids of a TCR chain.

[126] The composition of paragraph [124] or [125], wherein the first connector sequence and the second connector sequence encodes at least two contiguous amino acids of a TCR chain.

[127] The composition of any one of paragraphs [124]-[126], wherein the TCR chain of the portion of the TCR chain and the TCR chain encoded by the sequence encoding at least ten amino acids is the same.

[128] The composition of paragraph [124], wherein each nucleic acid molecule of the plurality of nucleic acid molecules comprises a sequence derived from a TCR V gene.

[129] The composition of any one of paragraphs [124]-[128], wherein each nucleic acid molecule of the plurality of nucleic acid molecules encodes a CDR3 of the TCR chain.

[130] The composition of paragraph [129], wherein each nucleic acid molecule of the plurality of nucleic acid molecules further comprises a J region of the TCR chain.

[131] The composition of paragraph [129], wherein each nucleic acid molecule of the plurality of nucleic acid molecules encodes a first CDR3 of a first TCR chain and a second CDR3 of a second TCR chain.

[132] The composition of paragraph [131], wherein each nucleic acid molecule of the plurality of nucleic acid molecules further comprises a first J region of a first TCR chain and a second J region of a second TCR chain.

[133] The composition of paragraph [131] or [132], wherein a sequence encoding the first CDR3 and a sequence encoding the second CDR3 are separated by at most 100 nucleotides.

[134] The composition of any one of paragraphs [124]-[133], wherein the first connector sequence or the second connector sequence comprises a sequence derived from a TCR V gene.

[135] The composition of any one of paragraphs [124]-[134], wherein the first connector sequence or the second connector sequence comprises a pre-determined sequence.

[136] The composition of any one of paragraphs [100]-[135], wherein the first connector sequence comprises at least one nucleotide that is different from a nucleotide of the second connector sequence.

[137] The composition of any one of paragraphs [100]-[136], wherein the first connector sequence encodes a same amino acid sequence as the second connector sequence.

[138] The composition of any one of paragraphs [100]-[136], wherein the first connector sequence encodes a different amino acid sequence from the second connector sequence.

[139] A method for generating a plurality of nucleic acid molecules, each nucleic acid molecule of the plurality encoding a T-cell receptor (TCR) chain or region thereof, comprising: contacting a first plurality of nucleic acid molecules and a second plurality of nucleic acid molecules to generate a third plurality of nucleic acid molecules comprising at least two different nucleic acid molecules, wherein each of the at least two different nucleic acid molecules has a different sequence encoding a different TCR chain or region thereof, and wherein the at least two different nucleic acid molecules are generated in a same compartment.

[140] The method of paragraph [139], wherein each nucleic acid molecule of the first plurality of nucleic acid molecules comprises a sequence encoding a CDR3 of the TCR chain.

[141] The method of paragraph [140], wherein each nucleic acid molecule of the first plurality of nucleic acid molecules comprises a J region of the TCR chain.

[142] The method of any one of paragraphs [139]-[141], wherein each nucleic acid molecule of the second plurality of nucleic acid molecules comprises a sequence derived from a TCR V gene of the TCR chain.

[143] The method of paragraph [142], wherein the TCR V gene is a human TCR V gene.

[144] The method of paragraph [142] or [143], wherein the TCR V gene is a human TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-6, TRAV9-1, TRAV9-2, TRAV10, TRAV12-1, TRAV12-2, TRAV12-3, TRAV13-1, TRAV13-2, TRAV14, TRAV16, TRAV17, TRAV18, TRAV19, TRAV20, TRAV21, TRAV22, TRAV23, TRAV24, TRAV25, TRAV26-1, TRAV26-2, TRAV27, TRAV29, TRAV30, TRAV34, TRAV35, TRAV36, TRAV38-1, TRAV38-2, TRAV39, TRAV40, or TRAV41.

[145] The method of paragraph [142] or [143], wherein the TCR V gene is a human TRBV2, TRBV3-1, TRBV4-1, TRBV4-2, TRBV4-3, TRBV5-1, TRBV5-4, TRBV5-5, TRBV5-6, TRBV5-8, TRBV6-1, TRBV6-2, TRBV6-3, TRBV6-4, TRBV6-5, TRBV6-6, TRBV6-8, TRBV6-9, TRBV7-2, TRBV7-3, TRBV7-4, TRBV7-6, TRBV7-7, TRBV7-8, TRBV7-9, TRBV9, TRBV10-1, TRBV10-2, TRBV10-3, TRBV11-1, TRBV11-2, TRBV11-3, TRBV12-3, TRBV12-4, TRBV12-5, TRBV13, TRBV14, TRBV15, TRBV16, TRBV18, TRBV19, TRBV20-1, TRBV24-1, TRBV25-1, TRBV27, TRBV28, TRBV29-1, or TRBV30.

[146] The method of any one of paragraphs [139]-[145], wherein the sequence derived from the TCR V gene comprises a sequence encoding FR1, CDR1, FR2, CDR2, and FR3.

[147] The method of any one of paragraphs [139]-[145], wherein the sequence derived from the TCR V gene comprises a sequence encoding L-PART1, L-PART2, FR1, CDR1, FR2, CDR2, and FR3.

[148] The method of any one of paragraphs [139]-[147], wherein the TCR chain is a TCR alpha chain, a TCR beta chain, a TCR gamma chain, or a TCR delta chain.

[149] The method of any one of paragraphs [140]-[148], wherein each nucleic acid molecule of the first plurality of nucleic acid molecules further comprises an additional sequence encoding an additional CDR3 of an additional TCR chain.

[150] The method of paragraph [149], wherein each nucleic acid molecule of the first plurality of nucleic acid molecules comprises an additional J region of the additional TCR chain.

[151] The method of paragraph [149] or [150], wherein the TCR chain and the additional TCR chain are a cognate pair of TCR chains.

[152] The method of any one of paragraphs [139]-[151], wherein a nucleic acid molecule of the plurality of nucleic acid molecules encodes a different TCR or region thereof

[153] The method of any one of paragraphs [139]-[152], wherein a given nucleic acid molecule of the first plurality of nucleic acid molecules comprises a connector sequence, which connector sequence is usable for linking the given nucleic acid molecule of the first plurality of nucleic acid molecules to a given nucleic acid molecule of the second plurality of nucleic acid molecules.

[154] The method of paragraph [153], wherein the given nucleic acid molecule of the first plurality of nucleic acid molecules and the given nucleic acid molecule of the second plurality of nucleic acid molecules encodes a functional TCR chain or region thereof.

[155] The method of paragraph [153] or [154], wherein the given nucleic acid molecule of the second plurality of nucleic acid molecules comprises an anti-connector sequence, which anti-connector sequence is complementary to the connector sequence of the given nucleic acid molecule of the first plurality of nucleic acid molecules.

[156] The method of any one of paragraphs [153]-[155], further comprising linking the given nucleic acid molecule of the first plurality of nucleic acid molecules and the given nucleic acid molecule of the second plurality of nucleic acid molecules.

[157] The method of paragraph [156], wherein linking comprises hybridizing the given nucleic acid molecule of the first plurality of nucleic acid molecules and the given nucleic acid molecule of the second plurality of nucleic acid molecules.

[158] The method of paragraph [157], wherein hybridizing comprises hybridizing the connector sequence of the given nucleic acid molecule of the first plurality of nucleic acid molecules with the anti-connector sequence of the given nucleic acid molecule of the second plurality of nucleic acid molecules.

[159] The method of any one of paragraphs [156]-[158], further comprising (i) extending a free 3' end of the given nucleic acid molecule of the second plurality of nucleic acid molecules using the given nucleic acid molecule of the first plurality of nucleic acid molecules as a template, and/or (ii) extending a free 3' end of the nucleic acid molecule of the first plurality of nucleic acid molecules using the given nucleic acid molecule of the second plurality of nucleic acid molecules as a template, to generate a nucleic acid molecule of the third plurality of nucleic acid molecules.

[160] The method of any one of paragraphs [139]-[159], further comprising ligating the given nucleic acid molecule of the first plurality of nucleic acid molecules and the given nucleic acid molecule of the second plurality of nucleic acid molecules.

[161] The method of any one of paragraphs [139]-[160], further comprising contacting the nucleic acid molecule of the third plurality of nucleic acid molecules with a restriction enzyme to generate a sticky end.

[162] The method of any one of paragraphs [139]-[161], further comprising contacting the nucleic acid molecule of the third plurality of nucleic acid molecules with an additional nucleic acid molecule.

[163] The method of paragraph [162], wherein the additional nucleic acid molecule encodes a constant region or a portion thereof of a TCR chain.

[164] The method of paragraph [162] or [163], further comprising ligating the nucleic acid molecule of the third plurality of nucleic acid molecules and the additional nucleic acid molecule.

[165] The method of any one of paragraphs [139]-[164], wherein at least five different nucleic acid molecules of the third plurality of nucleic acid molecules are generated in the same compartment.

[166] The method of any one of paragraphs [139]-[165], wherein at least ten different nucleic acid molecules of the third plurality of nucleic acid molecules are generated in the same compartment.

[167] The method of any one of paragraphs [139]-[166], wherein the same compartment is a well, a tube, or a droplet.

[168] A method for generating a plurality of nucleic acid molecules, comprising: (a) providing a first plurality of nucleic acid molecules, wherein a nucleic acid molecule of the first plurality of nucleic acid molecules comprises a sequence encoding a first CDR3 of a first T-cell receptor (TCR) chain and a second CDR3 of a second TCR chain, wherein the first CDR3 and the second CDR3 are from a cognate pair of TCR chains; (b) providing a second plurality of nucleic acid molecules, wherein a nucleic acid molecule of the second plurality of nucleic acid molecules comprises a sequence derived from a TCR V gene; and (c) contacting the first plurality of nucleic acid molecules and the second plurality of nucleic acid molecules, wherein the nucleic acid molecule of the first plurality of nucleic acid molecules links with the nucleic acid molecule of the second plurality of nucleic acid molecules to form a linear nucleic acid molecule comprising the sequence encoding the first CDR3 and the second CDR3 and the sequence derived from the TCR V gene, wherein the sequence encoding the first CDR3 and the second CDR3 and the TCR V gene are derived from the cognate pair of TCR chains.

[169] A method for generating a plurality of nucleic acid molecules, comprising: (a) providing a first plurality of nucleic acid molecules, wherein a nucleic acid molecule of the first plurality of nucleic acid molecules comprises (i) a synthetic sequence encoding a first CDR3 of a first T-cell receptor (TCR) chain and a second CDR3 of a second TCR chain and (ii) a synthetic sequence encoding a third CDR3 of a third T-cell receptor (TCR) chain and a fourth CDR3 of a fourth TCR chain, wherein the first CDR3 and the second CDR3 are from a first cognate pair of TCR chains and wherein the third CDR3 and the fourth CDR3 are from a second cognate pair of TCR chains; (b) providing a second plurality of nucleic acid molecules, wherein a nucleic acid molecule of the second plurality of nucleic acid molecules comprises a sequence derived from a TCR V gene; and (c) contacting the first plurality of nucleic acid molecules and the second plurality of nucleic acid molecules, wherein the nucleic acid molecule of the first plurality of nucleic acid molecules links with the nucleic acid molecule of the second plurality of nucleic acid molecules to form a nucleic acid molecule comprising the sequence encoding the first CDR3 and the second CDR3 and the sequence derived from the TCR V gene, wherein the sequence encoding the first CDR3 and the second CDR3 and the TCR V gene are derived from the cognate pair of TCR chains.

[170] A method of identifying a sequence of a natively paired T-cell receptor (TCR) in a tissue sample from a subject, comprising: (a) identifying one or more paired sequences of one or more natively paired TCRs in a sample containing a plurality of peripheral T cells obtained from the subject, wherein each of the one or more paired sequences comprises a CDR3 sequence; and (b) identifying a tissue CDR3 sequence of a TCR chain of a TCR in the tissue sample for which the other TCR chain to which it is natively paired is unknown, wherein the tissue CDR3 sequence matches a CDR3 sequence of at least one paired sequence of the one or more paired sequences of the one or more natively paired TCRs, thereby identifying the at least one paired sequence as the sequence of the natively paired TCR in the tissue sample.

[171] The method of paragraph [170], wherein identifying in (a) comprises sequencing the one or more natively paired TCRs in the sample containing the plurality of peripheral T cells.

[172] The method of paragraph [171], wherein the sequencing comprises single cell sequencing.

[173] The method of paragraph [172], wherein the single cell sequencing comprises partitioning the plurality of peripheral T cells into a plurality of compartments, each compartment comprising an individual peripheral T cell of the plurality of peripheral T cells.

[174] The method of any one of paragraphs [170]-[173], wherein the tissue sample is not a bodily fluid sample.

[175] The method of any one of paragraphs [170]-[174], wherein the tissue sample is a solid tumor sample.

[176] The method of any one of paragraphs [170]-[175], wherein the tissue sample is a fixed or frozen sample.

[177] The method of any one of paragraphs [170]-[176], wherein the sample containing the plurality of peripheral T cells is a peripheral blood mononuclear cell (PBMC) sample.

[178] The method of any one of paragraphs [170]-[177], further comprising, prior to (a), obtaining a blood sample from the subject.

[179] The method of paragraph [178], further comprising, prior to (a), isolating peripheral blood mononuclear cells from the blood sample.

[180] The method of any one of paragraphs [170]-[179], wherein the tissue sample comprises a tumor-infiltrating T cell.

[181] A method of identifying a target-reactive T-cell receptor (TCR), comprising: (a) providing a cell comprising the TCR identified from any one of paragraphs [170]-[180]; and (b) contacting the cell with a target antigen presented by an antigen-presenting cell (APC), wherein the cell binds to the target antigen presented by the APC via the TCR, thereby identifying the TCR as the target-reactive TCR.

[182] The method of paragraph [181], wherein the target antigen is a tumor antigen.

[183] The method of paragraph [181] or [182], further comprising delivering a sequence encoding the target-reactive TCR into a host cell.

[184] The method of paragraph [183], further comprising administering the host cell into the subject.

[185] The method of paragraph [183] or [184], wherein the host cell is a T cell.

[186] The method of paragraph [185], wherein the T cell is an autologous T cell.

[187] The method of paragraph [185], wherein the T cell is an allogeneic T cell.

[188] The method of any one of paragraphs [181]-[187], wherein the cell is a reporter cell line, which reporter cell line comprises a reporter gene that is expressed upon the cell binding to the target antigen presented by the APC.

SEQUENCE LISTING

<160> NUMBER OF SEQ ID NOS: 292

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcaaagactc tgcctcatac ctct                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgagagacg cagctgtgta ttact                                         25

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggggactcag ccgtgtactt ct                                            22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggtgactccg cagcctattt ct                                            22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggggatagc gcagtctatt tct                                           23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
ccggagacag cgcagtttat tttt                                              24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggtgacagcg ccgtctattt tt                                                22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tggaggactc aggcacttac ttct                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tggaggactc tgggacatac tttt                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tggaggactc tggcacctat tttt                                              24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actcgaggat tccggtactt atttct                                            26

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 12
gaagactccg ggacctactt tt                                              22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctggaggat tccggaacct atttct                                          26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctcgaagata gcggcacata ttttt                                           25

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcctggtgat agcgcaatat acttct                                          26

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tggcgactct gcaatgtact tct                                             23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cccggagact ctgctatgta ttttt                                           25

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 18
ggaatccgat agcgcagtct attact                                        26

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tccgacagcg ctgtctacta ct                                            22

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagagattga tagcgctgtt tactact                                       27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aggaatctga ttccgcagtc tattttt                                       27

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agaatctgat agcgccgttt attatt                                        26

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtccgactcc gcagtctact act                                           23

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aggagtctga ttctgcagtc tactatt				27

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccaagaaata gattccgcag tctactact				29

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtctgacagc gcagtctact tct				23

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aggaaagcga ttctgcagtc tattact				27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aagagtctga ctccgcagtt tattatt				27

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agaatccgac tctgcagttt actatt				26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gagtctgata gcgctgtgta ctact                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gaatctgact ctgccgttta ctatt                                          25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agtccgactc tgctgtgtac tact                                           24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccatctgatt ccgcactgta tttct                                          25

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
accttctgat agcgctctct attttt                                         26

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccttctgatt ctgcactgta cctgt                                          25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccaagcgatt ctgcactgta ttttt                                          25

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctctgactc tgcagtctac ctct                                           24

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cccagcgact ctgcagttta tctct                                          25

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccgacagcgc actctacctg t                                              21

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttccgactct gcactgtatc tgt                                            23

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tccgatagcg ccctgtattt ct                                             22

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctccgattcc gcactctatc tct                                            23

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cctccgatag cgctgtttat ctct                                          24

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcgacagcgc cctgtacttt t                                             21

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccctctgata gcgcactgta tctct                                         25

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cttctgacag cgctgtgtat ctgt                                          24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcgaggacac agctgtttac tttt                                          24

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agtgcgaaga tacagcagtt tacttct                                       27

```
<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cggtgtgagg atactgctgt ttatttct                                        28

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cgaagatacc gccgtctact ttt                                             23

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggcaactgac acagcagtct actttt                                          26

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gagcgattct gccgtttact tct                                             23

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tccgattccg ccgtgtattt tt                                              22

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttggtctgat tctgcagttt actttt                                          26

<210> SEQ ID NO 55
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtctgattc cgctgtctac tttt                                               24

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctggtctgac tctgctgttt attttt                                             26

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggtccgactg ggcagtctat tttt                                               24

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tggtctgatt ctgccgtcta tttct                                              25

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agcgactctg ccgtgtattt ct                                                 22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gagcgattgg gcagtctact ttt                                                23

<210> SEQ ID NO 61
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tggtccgatt ctgctgtcta ttttt                                             25

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agcctgaaga ttcagccatc tacttct                                           27

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cccgaggact ctgctattta cttct                                             25

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acagccagaa gattctgcaa tatacttct                                         29

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gctcgatgac acagctacat acatct                                            26

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcctggatga tactgcaaca tacatat                                           27

<210> SEQ ID NO 67
<211> LENGTH: 25
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 67
ctctctgact ctgcactgta ctact        25

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
actgtctgac tctgcactct attact        26

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ctgtccgatt ctgcactcta ctact        25

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aactgtctga ttctgctctg tactatt        27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tccgactccg ctctgtattt tt        22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
agcgactctg ccctctacta ct        22

<210> SEQ ID NO 73
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 73
tctctgactc cgctctctac tact                                              24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tctctgattc tgccctctac tttt                                              24

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gctctccgat tctgctctgt attatt                                            26

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gacaacagac tcaggcactt atctct                                            26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aacaactgac tctggcacat attttt                                            26

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cactgatagc ggaacctacc tct                                               23

<210> SEQ ID NO 79
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 79
tgacagcggc acctacctgt                                                   20

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
actacagatt ccggcactta cttct                                             25

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gccagataac tgattctggt acttacctgt                                        30

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
acaactgaca gcggaacata tctct                                             25

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aaataacaga tagcggtaca tacctgt                                           27

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ccacagattc tggcacctac ttct                                              24

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 85
actgactccg gaacctacct ct                                          22

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
accgactctg gcacttacct gt                                          22

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aatcacagac tctggaacct atctgt                                      26

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccaaattacc gattctggta catacctct                                   29

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cggagatagc gccacatact ttt                                         23

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aacctggaga ttctgcaaca tatttct                                     27

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctggggactc tgcaacttac ttct                                                24

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cctggagact cagctaccta cttct                                               25

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccggggatag cgctacttat tttt                                                24

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cctggagatt ccgcaactta ctttt                                               25

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95 ccagggatt ctgctaccta ttttt                                                25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cccggagatt ctgccactta tttct                                               25

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctggcgacag cgctacttat ttct                                          24

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aaccagacga ttcgggaaag tatttct                                       27

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cagaggattc agggacgtac ttct                                          24

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccagacgact ccggaaagta ctttt                                         25

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccgaggactc cggtacatac ttct                                          24

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aacccgatga ctctggtaag tattttt                                       27

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gccagaagac tccggtacat attttt                                  26

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tcaaattgaa gattctgcag tctactttt                               29

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gattgaggac tcggcagtat atttct                                  26

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aaatcgaaga ctctgcagtt tactttt                                 27

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gagcgactca gccaagtact tct                                     23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aggggatgct gggatctact ttt                                     23

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cccgaagata cagctgtcta cctgt                                             25

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
agggacgcag cagtctatca tt                                                22

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gccactctgc catctacttc tgt                                               23

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggcgcacact gtactgcaca t                                                 21

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tgatgactcg gccacatact tct                                               23

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tggaggactc agctgtgtac ttct                                              24

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
accagaagat agcgcagttt atctgt                                            26

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 116
atccagaaga ctcagctgtc tattttt                                27

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 117
tcgaagatag cgccatgtac tttt                                   24

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 118
actggaagat agcgctgtgt atttct                                 26

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 119
aagccagacc agcctctatt ttt                                    23

<210> SEQ ID NO 120
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 120
cccctctcag acatcagtgt acttct                                 26

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 121
gccagaccgc cgtgtatttc t                                      21

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ggcgacacag ccacctatct ct                                              22

<210> SEQ ID NO 123
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gcctaaagac agcgctgttt atctct                                          26

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ccaggactca gcggtgtatc ttt                                             23

<210> SEQ ID NO 125
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gcctagagta ttctgccatg tacctct                                         27

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aaaaatgaga tggcagtctt cctct                                           25

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cgaggatagg ggcctgtatc tct                                             23

```
<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcagaagact cagcactgta cttgt                                              25

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gacgactcag cactgtacct ct                                                 22

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggggactccg cactctatct ct                                                 22

<210> SEQ ID NO 131
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aaacaaacca gacatctgtg tacttct                                            27

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggcctggaga cagcagtatc tatttct                                            27

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tcagccatag cggtttttac ctct                                               24

<210> SEQ ID NO 134
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccgggatttt gtgactcatc                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gaggatcgta tgtttcgcac                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cttgtgtgca cttaccgtac                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tgatgcatct ccagtacagg                                              20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cttctgtgtg tacctcgaca                                              20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cttgcaatcc tttaccgtgc                                              20

<210> SEQ ID NO 140
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gcaagtgtgg aaaatgaccc                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gagtctagtc tcacaaccca                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gaaatgttga ggactccacg                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cctaacagat gctacgtgga                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gtaggtccac acagattcca                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gccagtcaca gcaaatacac                                              20

<210> SEQ ID NO 146
<211> LENGTH: 20
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 146
ccgctaccag tatgtacctt							20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
actgtgttcc ttgtcttccg							20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
tgaatgcatc tacggtaccg							20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149
gcgcttatca atcttgctcg							20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
cggtcaattc agtagccact							20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
ggacacatgt acactagcca							20

<210> SEQ ID NO 152
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 152
tgggagctct acgaaaatcc                                                    20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gttctcgaga tcgtcacaca                                                    20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cttctgcatt cgatccttgc                                                    20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gcagagttgt gtgattggag                                                    20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cccatcaatt cggaaccatc                                                    20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
atcgtaaccc aagtctgtgg                                                    20

<210> SEQ ID NO 158
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 158
ggcgaaatga tccctgaatg                                                     20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
agtgctcaga actttcaggc                                                     20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gatcgttaac tctttgggcg                                                     20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
acacgaggat tgctgtagag                                                     20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ttctaccaca ttgtctcggg                                                     20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gaatggctaa actgtgtccc                                                     20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 164
cggactgtac gagaaactga                                        20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cttgcgacaa actactcctg                                        20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ccgttttact ttgtcgccac                                        20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tggatgatat cacttcggcg                                        20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ccaacctcta tatgtgccca                                        20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgaacaggta tgctccagag                                        20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ttgtggatat cgtctggtcc                                          20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ctgtggaact cgactcttgt                                          20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ctccaggatg cacaaattcg                                          20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggctcatgac aaaacacagg                                          20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ccgaatccga aaacaacacg                                          20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
agacctaaca ctgtgatgcg                                          20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cctgggtgag cataaacttc                                           20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gagtcttgga cgaacaaagg                                           20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cacgtaccca tcatgttctg                                           20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ccgtgttagt caagtgtgtg                                           20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ctggtggcat aaatggaacg                                           20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tggatgtggg tatcaatggg                                           20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgtggctaac gtaggacaag                                               20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ccctcgttgt gaaaatgtgc                                               20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcgtcatagg tcagcttacg                                               20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cctgatgacc tctatgccaa                                               20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cggcaagaat gaatagggtg                                               20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gtgctattgg tgggaaatgg                                               20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gccatgtttg cttactgacg                                        20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cgttgtggca ttcattagcg                                        20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gcggtaggat tggatctcat                                        20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cctcgcaaag ctgttatgac                                        20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gccttcatgt tattggacgc                                        20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
agctgtagtg ttcttgaggc                                        20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ggtagtgttc gtgtgacatg                                        20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cgcggcatat gttcatatcc                                               20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gagactggat catgcaacag                                               20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cacaacttct ctggactcca                                               20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cgaccatgat ctgtatgcgt                                               20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggtgtgactc ttgtttccgt                                               20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
acgtacatac aagtctggcg                                               20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cctcaaggat tcactcgcaa                                               20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ctgtatagga tgtccacgca                                               20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gcctgtgatt ggtaaatgcg                                               20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
cgcactcgta gcatctagaa                                               20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
cgatttgttg tccctagctg                                               20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cccacttcat ctgactctga                                               20

```
<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cggcattgta caggtgttac                                                     20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tctcctattt ccctgaacgg                                                     20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cttgtccact aaacgcaacg                                                     20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cgggtatcac tgggtaatga                                                     20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggaacagaga ccaatccagt                                                     20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gtgggcatcc gaaatttcag                                                     20

<210> SEQ ID NO 213
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cgcgacgaca ttaccaatag                                                   20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cgtcggaata tgctctcaga                                                   20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gatgcagatc aatgagtggc                                                   20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
actgcttaca agtgtccacg                                                   20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
actgtatgca agctagtccc                                                   20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
agatctccca aaagtgtccg                                                   20

<210> SEQ ID NO 219
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ttccagaacc atgtgatccc                                              20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gccttgtctt tcaacctctg                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gatacggatc ttcacatgcg                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cgctcatcta ggttggacta                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cgcgttcaga ttccaaacag                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gcctggttac acatgctatc                                              20

<210> SEQ ID NO 225
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 225
gcaaaggtcc tacaggtttc                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ggctttccat gtctatgctc                                              20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gcgacattag cagagtaggt                                              20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ctcgccatac tatctgcatg                                              20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ctactgaaca cttggcaagc                                              20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ctgttcaatt cctgtgcgag                                              20

<210> SEQ ID NO 231
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 231
cactgagatg gaatttggcg                                                    20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gtccatcaca acttccactg                                                    20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ggctcagtct actttgcttc                                                    20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gttagcttcc gacacaatgg                                                    20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccgtgacaca ctttcatctc                                                    20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ccgggatgtc attatgagca                                                    20

<210> SEQ ID NO 237
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 237
gagtgtccta cgagatcaga                                                    20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
taacgtctct ctgagtgtgg                                                    20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
accctagaca agagacacct                                                    20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tgctcagtac tcttcatcgc                                                    20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
agctcaatca tggctatcgg                                                    20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ctacacattg catccaaccc                                                    20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 243
acttgtcgaa tagctcaggc                                         20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gtctaccctg agaaccagtt                                         20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cagcaacaac ctaccttagc                                         20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
cgatttgttg gtacgtgtcc                                         20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gccatttcct ttgtacctgc                                         20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ggccaataga gagaccacaa                                         20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
cggagtcaca tgggtagaat                                          20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cccagtacat ttgtcggttg                                          20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
cccactagct gctactcaaa                                          20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ggtgttgcgt caaagtagac                                          20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tactccagct cttactgtgc                                          20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggatgagcag tcaacagttc                                          20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 255
tcaggatcga tcagttgtcc                                            20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cctctctttt gtgcggaaac                                            20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tgcctaggat ttcgagaacg                                            20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ggcattgtcc ttaacttcgc                                            20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tgcatctaac tacgatgggc                                            20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ccctagtagc cacacaacat                                            20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
```
gtgccatgaa tcatcgtctc                                         20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
cgctctgatg aaagctccat                                         20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccagccatag tgcatatcct                                         20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gagattgtca tgtggtcgac                                         20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ccgcagtcta acaggaaatc                                         20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cgcttcgact gaaccttatg                                         20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267

```
cgatgcgacc aatagaagtg                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gcccttggta cgacatattg                                               20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
cagtgattta ggtgacgcag                                               20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ggcatggaag aggtagtttc                                               20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ccgatcgtat tctgtgtcca                                               20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctaagtcaag cacatgggac                                               20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gatccacact caatctcctg                                               20
```

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ccttgtcaca tgctggtatc                                          20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
cgcgattgtg gttaataggc                                          20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gtaggcaaag ttcaccacac                                          20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gccacgaatc gaacaagtac                                          20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ttgagatctc gatgagcacg                                          20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gggccaagat ctattcgtca                                          20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gtggctatag gtatgtccga                                                 20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccacactttc tgcattcgac                                                 20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
cggcatctca aagcacatac                                                 20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
cgtccacaaa tttactgccc                                                 20

<210> SEQ ID NO 284
<211> LENGTH: 19
<212> TYPE: PRT
<213> ORGANISM: Porcine teschovirus

<400> SEQUENCE: 284

Ala Thr Asn Phe Ser Leu Leu Lys Gln Ala Gly Asp Val Glu Glu Asn
1               5                   10                  15

Pro Gly Pro

<210> SEQ ID NO 285
<211> LENGTH: 20
<212> TYPE: PRT
<213> ORGANISM: Equine rhinitis A virus

<400> SEQUENCE: 285

Gln Cys Thr Asn Tyr Ala Leu Leu Lys Leu Ala Gly Asp Val Glu Ser
1               5                   10                  15

Asn Pro Gly Pro
            20

```
<210> SEQ ID NO 286
<211> LENGTH: 22
<212> TYPE: PRT
<213> ORGANISM: Foot-and-mouth disease virus

<400> SEQUENCE: 286

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 287
<211> LENGTH: 18
<212> TYPE: PRT
<213> ORGANISM: Thosea asigna virus

<400> SEQUENCE: 287

Glu Gly Arg Gly Ser Leu Leu Thr Cys Gly Asp Val Glu Glu Asn Pro
1               5                   10                  15

Gly Pro

<210> SEQ ID NO 288
<211> LENGTH: 5
<212> TYPE: PRT
<213> ORGANISM: Unknown
<220> FEATURE:
<223> OTHER INFORMATION: Description of Unknown:
      Enterokinase cleavage site

<400> SEQUENCE: 288

Asp Asp Asp Asp Lys
1               5

<210> SEQ ID NO 289
<211> LENGTH: 4
<212> TYPE: PRT
<213> ORGANISM: Unknown
<220> FEATURE:
<223> OTHER INFORMATION: Description of Unknown:
      Factor Xa cleavage site

<400> SEQUENCE: 289

Ile Glu Gly Arg
1

<210> SEQ ID NO 290
<211> LENGTH: 6
<212> TYPE: PRT
<213> ORGANISM: Unknown
<220> FEATURE:
<223> OTHER INFORMATION: Description of Unknown:
      Thrombin cleavage site

<400> SEQUENCE: 290

Leu Val Pro Arg Gly Ser
1               5

<210> SEQ ID NO 291
<211> LENGTH: 8
<212> TYPE: PRT
<213> ORGANISM: Unknown
<220> FEATURE:
<223> OTHER INFORMATION: Description of Unknown:
      Renin cleavage site

<400> SEQUENCE: 291
```

```
His Pro Phe His Leu Val Ile His
1               5

<210> SEQ ID NO 292
<211> LENGTH: 4
<212> TYPE: PRT
<213> ORGANISM: Unknown
<220> FEATURE:
<223> OTHER INFORMATION: Description of Unknown:
      Caspase protease cleavage site

<400> SEQUENCE: 292

Asp Glu Val Asp
1
```

What is claimed is:

1. A method for generating a plurality of at least 100 nucleic acid molecules encoding a plurality of at least 100 different native T-cell receptor (TCR) alpha chains or portions thereof from a mixed population of cells in a single compartment, the method comprising:
   (a) providing a first plurality of at least 100 nucleic acid molecules in a single compartment, each nucleic acid molecule of the first plurality of at least 100 nucleic acid molecules comprising a sequence encoding a CDR3 alpha (CDR3a) of a different TCR alpha chain and a unique connector sequence;
   (b) providing a second plurality of nucleic acid molecules in the same single compartment containing the first plurality of at least 100 nucleic acid molecules of (a), thereby contacting the first plurality of at least 100 nucleic acid molecules of (a) to the second plurality of nucleic acid molecules in the same single compartment, wherein each nucleic acid molecule of the second plurality of nucleic acid molecules comprises a sequence from a TCR alpha variable (TRAV) gene and a unique anti-connector sequence, and wherein the second plurality of nucleic acid molecules comprises at least five different sequences from at least five different TRAV genes; and
   (c) generating within the same single compartment a third plurality of at least 100 nucleic acid molecules, each nucleic acid molecule of the third plurality comprising a sequence from one of the sequences encoding a CDR3a from the first plurality of at least 100 nucleic acid molecules of (a) and a sequence from one of the at least five different TRAV genes of the second plurality of nucleic acid molecules of (b), wherein generating comprises specifically linking the unique connector sequence of a nucleic acid molecule of the first plurality of at least 100 nucleic acid molecules of (a) to the unique anti-connector sequence of a nucleic acid molecule of the second plurality of nucleic acid molecules of (b) that comprises a sequence from a single given TRAV gene of the at least five different TRAV genes, thereby generating the plurality of at least 100 nucleic acid molecules encoding the plurality of at least 100 different native TCR alpha chains or portions thereof from the mixed population of cells, wherein the unique anti-connector sequence of the sequence from the single given TRAV gene is complementary to the unique connector sequence of the nucleic acid molecule of the first plurality of at least 100 nucleic acid molecules, and wherein the single given TRAV gene is cognate to the CDR3a to which it is linked.

2. The method of claim 1, wherein the sequence encoding the CDR3a and the at least five different sequences from at least five different TRAV genes are from a sample from a subject.

3. The method of claim 2, wherein the sequence from the single given TRAV gene and the sequence encoding the CDR3α to which it is specifically linked in (c) are from a same TCR alpha chain expressed in a tumor-infiltrating T cell of the sample from the subject.

4. The method of claim 1, wherein the sequence from the single given TRAV gene and the sequence encoding the CDR3α to which it is specifically linked form a sequence that encodes a native sequence of a TCR alpha chain.

5. The method of claim 1, wherein each nucleic acid molecule of the first plurality of at least 100 nucleic acid molecules of (a) further comprises a J region of a TCR alpha chain.

6. The method of claim 5, wherein the J region and the sequence encoding the CDR3α are from a same TCR alpha chain.

7. The method of claim 1, wherein the at least five different TRAV genes are human TRAV genes or mouse TRAV genes.

8. The method of claim 1, wherein each nucleic acid molecule of the second plurality of nucleic acid molecules of (b) comprises a sequence encoding a first part of a leader peptide (L-PART1), a second part of the leader peptide (L-PART2), a framework 1 (FR1), a complementarity determining region 1 (CDR1), a framework 2 (FR2), a complementarity determining region 2 (CDR2), and a framework 3 (FR3).

9. The method of claim 1, wherein the plurality of at least 100 nucleic acid molecules generated in (c) further encodes a plurality of at least 100 different native TCR beta chains or portion thereof, and wherein each nucleic acid molecule of the first plurality of at least 100 nucleic acid molecules of (a) further comprises an additional sequence encoding a CDR3 beta (CDR3β) of a TCR beta chain.

10. The method of claim 9, wherein each nucleic acid molecule of the first plurality of at least 100 nucleic acid molecules of (a) comprises an additional J region of the TCR beta chain.

11. The method of claim 9, wherein the sequence encoding the CDR3α and the additional sequence encoding the CDR3β are separated by at most 100 nucleotides.

12. The method of claim 9, wherein the TCR alpha chain and the TCR beta chain is a cognate pair of TCR chains expressed in a sample from a subject.

13. The method of claim 1, wherein the unique connector sequence encodes at least 5 amino acids of a TRAV gene adjacent to a sequence encoding a CDR3α in a rearranged gene.

14. The method of claim 1, wherein each unique connector sequence is complementary to a unique anti-connector sequence, and wherein each unique connector sequence (i) has a nucleic acid sequence that is codon-diversified such that it comprises a mutation relative to a sequence that is conserved in a TRAV gene adjacent to a sequence encoding a CDR3α in a rearranged gene, and (ii) encodes a same amino acid sequence that is conserved in the TRAV gene adjacent to the sequence encoding the CDR3α in the rearranged gene.

15. The method of claim 1, wherein linking comprises hybridizing the unique connector sequence with the unique anti-connector sequence.

16. The method of claim 15, further comprising (i) extending a free 3' end of the nucleic acid molecule of the second plurality of nucleic acid molecules of (b) using the nucleic acid molecule of the first plurality of at least 100 nucleic acid molecules of (a) as a template, or (ii) extending a free 3' end of the nucleic acid molecule of the first plurality of at least 100 nucleic acid molecules of (a) using the nucleic acid molecule of the second plurality of nucleic acid molecules of (b) as a template, to generate a third nucleic acid molecule of the third plurality of at least 100 nucleic acid molecules.

17. The method of claim 1, further comprising ligating the nucleic acid molecule of the first plurality of at least 100 nucleic acid molecules of (a) and the nucleic acid molecule of the second plurality of nucleic acid molecules (b).

18. The method of claim 17, further comprising contacting the third plurality of at least 100 nucleic acid molecules with a restriction enzyme to generate a sticky end.

19. The method of claim 18, further comprising contacting the third plurality of at least 100 nucleic acid molecules with a fourth plurality of nucleic acid molecules encoding a constant region or portion thereof of a TCR chain, wherein a nucleic acid molecule of the third plurality of at least 100 nucleic acid molecules of (c) hybridizes with a nucleic acid molecule of the fourth plurality of nucleic acid molecules via the sticky end.

20. The method of claim 19, wherein the fourth plurality of nucleic acid molecules encodes a constant region of a TCR beta chain.

21. The method of claim 19, further comprising ligating a nucleic acid molecule of the third plurality of at least 100 nucleic acid molecules of (c) and a nucleic acid molecule of the fourth plurality of nucleic acid molecules to generate a fifth plurality of nucleic acid molecules.

22. The method of claim 21, further comprising circularizing each nucleic acid molecule of the fifth plurality of nucleic acid molecules.

23. The method of claim 22, wherein circularizing comprises joining two ends of each nucleic acid molecule of the fifth plurality of nucleic acid molecules by ligation or overlapping polymerase chain reaction (PCR).

24. The method of claim 1, wherein at least 500 nucleic acid molecules, each encoding a different native TCR alpha chain or portion thereof, are generated in the same single compartment.

25. The method of claim 1, wherein each nucleic acid molecule of the third plurality of at least 100 nucleic acid molecules generated in (c) is a linear nucleic acid molecule.

26. The method of claim 1, wherein each nucleic acid molecule of the first plurality of at least 100 nucleic acid molecules of (a) comprises a unique barcode.

27. The method of claim 26, subsequent to (c), further comprising selectively amplifying a nucleic acid molecule from the third plurality of at least 100 nucleic acid molecules using a primer targeting the unique barcode.

28. The method of claim 1, further comprising, prior to (a), sequencing a sample from a subject to obtain sequences of cognate pairs of TCRs expressed in the subject.

29. The method of claim 1, further comprising expressing a sequence of at least one nucleic acid molecule of the plurality of at least 100 nucleic acid molecules encoding the plurality of at least 100 different native TCR alpha chains or portion thereof generated in (c) in a cell.

30. A method for generating a plurality of at least 100 nucleic acid molecules encoding a plurality of at least 100 different native T-cell receptor (TCR) beta chains or portions thereof from a mixed population of cells in a single compartment, the method comprising:
(a) providing a first plurality of at least 100 nucleic acid molecules in a single compartment, each nucleic acid molecule of the first plurality of at least 100 nucleic acid molecules comprising a sequence encoding a CDR3 beta (CDR3β) of a different TCR beta chain and a unique connector sequence;
(b) providing a second plurality of nucleic acid molecules in the same single compartment containing the first plurality of at least 100 nucleic acid molecules of (a), thereby contacting the first plurality of at least 100 nucleic acid molecules of (a) to the second plurality of nucleic acid molecules in the same single compartment, wherein each nucleic acid molecule of the second plurality of nucleic acid molecules comprises a sequence from a TCR beta variable (TRBV) gene and a unique anti-connector sequence, and wherein the second plurality of nucleic acid molecules comprises at least five different sequences from at least five different TRBV genes; and
(c) generating within the same single compartment a third plurality of at least 100 nucleic acid molecules, each nucleic acid molecule of the third plurality comprising a sequence from one of the sequences encoding a CDR3β from the first plurality of at least 100 nucleic acid molecules of (a) and a sequence from one of the at least five different TRBV genes of the second plurality of nucleic acid molecules of (b), wherein generating comprises specifically linking the unique connector sequence of a nucleic acid molecule of the first plurality of at least 100 nucleic acid molecules of (a) to the unique anti-connector sequence of a nucleic acid molecule of the second plurality of nucleic acid molecules of (b) that comprises a sequence from a single given TRBV gene of the at least five different TRBV genes, thereby generating the plurality of at least 100 nucleic acid molecules encoding the plurality of at least 100 different native TCR beta chains or portions thereof from the mixed population of cells, wherein the unique anti-connector sequence of the sequence from the single given TRBV gene is complementary to the unique connector sequence of the nucleic acid molecule of the first plurality of at least 100 nucleic acid molecules, and wherein the single given TRBV gene is cognate to the CDR3β to which it is linked.

* * * * *